US007305331B2

(12) United States Patent
Allen et al.

(10) Patent No.: US 7,305,331 B2
(45) Date of Patent: Dec. 4, 2007

(54) SYSTEM AND METHOD FOR SIMULATING CELLULAR BIOCHEMICAL PATHWAYS

(75) Inventors: Eric B. Allen, Olney, MD (US); Gilberto Fragoso, Germantown, MD (US); John Armstrong, Rockville, MD (US); Sandra Allen, Silver Spring, MD (US)

(73) Assignee: New World Science & Technology, Inc., Silver Spring, MD (US)

( * ) Notice: Subject to any disclaimer, the term of this patent is extended or adjusted under 35 U.S.C. 154(b) by 512 days.

(21) Appl. No.: 10/360,796

(22) Filed: Feb. 10, 2003

(65) Prior Publication Data
US 2003/0176978 A1 Sep. 18, 2003

(51) Int. Cl.
G06N 3/00 (2006.01)
G06G 7/58 (2006.01)

(52) U.S. Cl. ........................................... 703/11; 702/19
(58) Field of Classification Search ...................... None
See application file for complete search history.

(56) References Cited

U.S. PATENT DOCUMENTS

| | | | |
|---|---|---|---|
| 4,518,866 A | 5/1985 | Clymer | |
| 4,736,322 A | 4/1988 | Clifford | |
| 5,136,687 A | 8/1992 | Edelman et al. | |
| 5,273,038 A | 12/1993 | Beavin | |
| 5,526,281 A | 6/1996 | Chapman et al. | |
| 5,553,004 A | 9/1996 | Gronbech-Jensen et al. | |
| 5,621,671 A | 4/1997 | Bodnar | |
| 5,657,255 A | 8/1997 | Fink et al. | |
| 5,680,331 A | 10/1997 | Blaney et al. | |
| 5,680,590 A | 10/1997 | Parti | |
| 5,699,268 A | 12/1997 | Schmidt | |
| 5,751,928 A | 5/1998 | Bakalash | |
| 5,808,918 A | 9/1998 | Fink et al. | |
| 5,914,891 A | 6/1999 | McAdams et al. | |
| 5,930,154 A | 7/1999 | Thalhammer-Reyero | |
| 5,963,212 A | 10/1999 | Bakalash | |
| 5,980,096 A | 11/1999 | Thalhammer-Reyero | |
| 6,051,029 A | 4/2000 | Paterson et al. | |

OTHER PUBLICATIONS

Scott et al., Cell Communication: The Inside Story, Scientific American, vol. 282 No. 6, pp. 72-79 Jun. 2000.
Karp, P.D., Computer Corner: Metabolic databases, TIBS, vol. 23, pp. 114-116 (Mar. 1998).
Clancey, W.J., From Guidon to Neomycin and Heracles in Twenty Short Lessons: ORN Final Report 1979-1985, The AI Magazine, Aug. 1986, pp. 40-60.
Bourne, J.R., Critical Reviews In Biomedical Engineering, 19(4): 261-292 (1992), pp. 261-292.
Karp et al., EcoCyc: Encyclopedia of *Escherichia coli* Genes and Metabolism; Nucleic Acids Research, 1997, vol. 25, No. 1, pp. 43-50.
Karp, P.D., Bioinformatics: Database links are a foundation for interoperability, TIBTECH, Aug. 1996 (vol. 14), pp. 273-279.
Paley, et al., Gene-Combis: Adapting EcoCyc for use on the World Wide Web, Gene 172 (1996) GC43-GC50.
Karp, P.D., Journal Of Computational Biology, A Strategy for Database Interoperation, vol. 2, No. 4, 1995, pp. 573-586.
Karp, P.D., Representation of Metabolic Pathways, ISMB-94, pp. 204-211, 1994.
Karp et al., The EcoCyc and MetaCyc databases, Nucleic Acids Research 2000, vol. 28, No. 1, pp. 56-59.
Karp, P.D., Hypothesis Formation and Qualitative Reasoning in Molecular Biology, AI Magazine, pp. 9-11 (Winter 1990).
Ouzounis et al., Resource: Global Properties of the Metabolic Map of *Escherichia coli*, Genome Research, 10: 568-576, 2000.
Karp et al., Representations of Metabolic Knowledge, ISMB-93, pp. 207-215, 1993.
Karp et al., HinCyc: A Knowledge Base of the Complete Genome and Metabolic Pathways of *H. influenzae*, ISMB-96, pp. 116-124, 1996.
Karp et al., Focus: Integrated pathway-genome database and their role in drug discovery, TIBTECH, Jul. 1999 (vol. 17), pp. 275-281.
The WWW Virtual Library of Cell Biology: Signal Transduction, pp. 1-3, printed from http://vl.bwh.harvard.edu/signal_transduction.shtml, Jun. 15, 2000.
Cell Signaling Networks Database, pp. 1-2, [retrieved on Jun. 15, 2000] Retrieved from <http://geo.nihs.go.jp/cgi-bin/display_tissue/MAP-kinase>.
Kohn, K.W., "Functional capabilities of molecular network components controlling the mammalian GI/S cell cycle phase transition", Oncogene (1998), vol. 16, pp. 1065-1075.
Abouhamad, et al., "Computer-Aided Resolution of an Experimental Paradox in Bacterial Chemotaxis", Journal Of Bacteriology, Aug. 1998, vol. 180, No. 15, pp. 3757-3764.
PCT International Preliminary Examination Report, PCT/US01/07794, mailed Sep. 4, 2003.
Ogata et al., "KEGG: Kyoto Encyclopedia of Genes and Genomes", Nuc. Acids Res. (Jan. 1999), vol. 27, No. 1, pp. 29-34.

*Primary Examiner*—Marjorie A Moran
(74) *Attorney, Agent, or Firm*—Blackwell Sanders LLP; David H. Milligan

(57) ABSTRACT

The present invention relates to a system and method for examining pathways. In particular, the present invention provides a system and method for examining pathways that underlie cellular functions, specifically signal transduction pathways. One aspect of the invention relates to the prediction of (a) functional properties of a protein, (b) potential interaction partners of the protein, and/or (c) potential target biochemical pathways within which the protein may interact. Thus, according to the invention, the influence of a given stimulus on a biochemical pathway can be assessed.

21 Claims, 40 Drawing Sheets

Fig. 16

```
CellTek - [CellTek - Textual Path...]
File
Initial Conditions
    User Name:     CellTekUser
    Pathway Type:  Forward Pathway
    Context:       Immunology Test Cell
    Stimulus:      CD154
    Exclusions:    None
    EndPoint:      None 0   CD154 Binds To CD40
0   Inactive JNK1 Binds To Elk1
0   Inactive JNK2 Binds to Elk1

1   CD154/CD40 Binds To TRAF6
1   CD154/CD40 Binds To TRAF3
1   CD154/CD40 Binds To TRAF2
1   CD154/CD40 Binds To TRAF5
1   CD154/CD40 Leadst to Lck Activation 2   TRAF6 Activates TANK
2   TRAF6 Binds To RIP2
2   TRAF2 Binds To TANK
2   TRAF2 Binds To ASK1
2   TRAF2 Binds To RIP
2   TRAF6 Binds TAK1/TAB1
2   TRAF3 Leads To Activated JNK1
2   TRAF2 Binds To MEKK1
2   TRAF5 Activates ASK1
2   TRAF5 Binds To TANK
2   TRAF6 Binds to ECSIT
2   TRAF6 Leads to Raf-1[+]
2   TRAF6 Binds to ASK1
2   TRAF6 Binds to NIK
2   TRAF2 Binds To GCK
```

```
CellTek - [CellTek - Textual Pathway]
File
Initial Conditions
    User Name:     CellTekUser
    Pathway Type:  Forward Pathway
    Context:       Immunology Test Cell
    Stimulus:      CD154
    Exclusions:    None
    EndPoint:      None CD154 Binds To CD40
CD154/CD40 Binds To TRAF6
TRAF6 Activates TANK
TANK Interacts With TBK1
TBK1 Leads To NIK Activation
NIK Binds to IKK-A and IKK-B
NIK Phosphoporylates IKK-A
Phosphorylation of IkB-A
Ubiquitination of IkB-A CD154 Binds To CD40
CD154/CD40 Binds To TRAF6
TRAF6 Activates TANK
TANK Interacts With GCKR
GCKR Activates MEKK1
MEKK1 Activates IKK-B
IKK-B Phosphorylates IkB-A/NFkB
Ubiquitination of IkB-A CD154 Binds To CD40
CD154/CD40 Binds To TRAF6
TRAF6 Activates TANK
TANK Interacts With GCKR
GCKR Activates MEKK1
MEKK1 Phosphorylates MKK4
```

5130

5320

Fig. 31
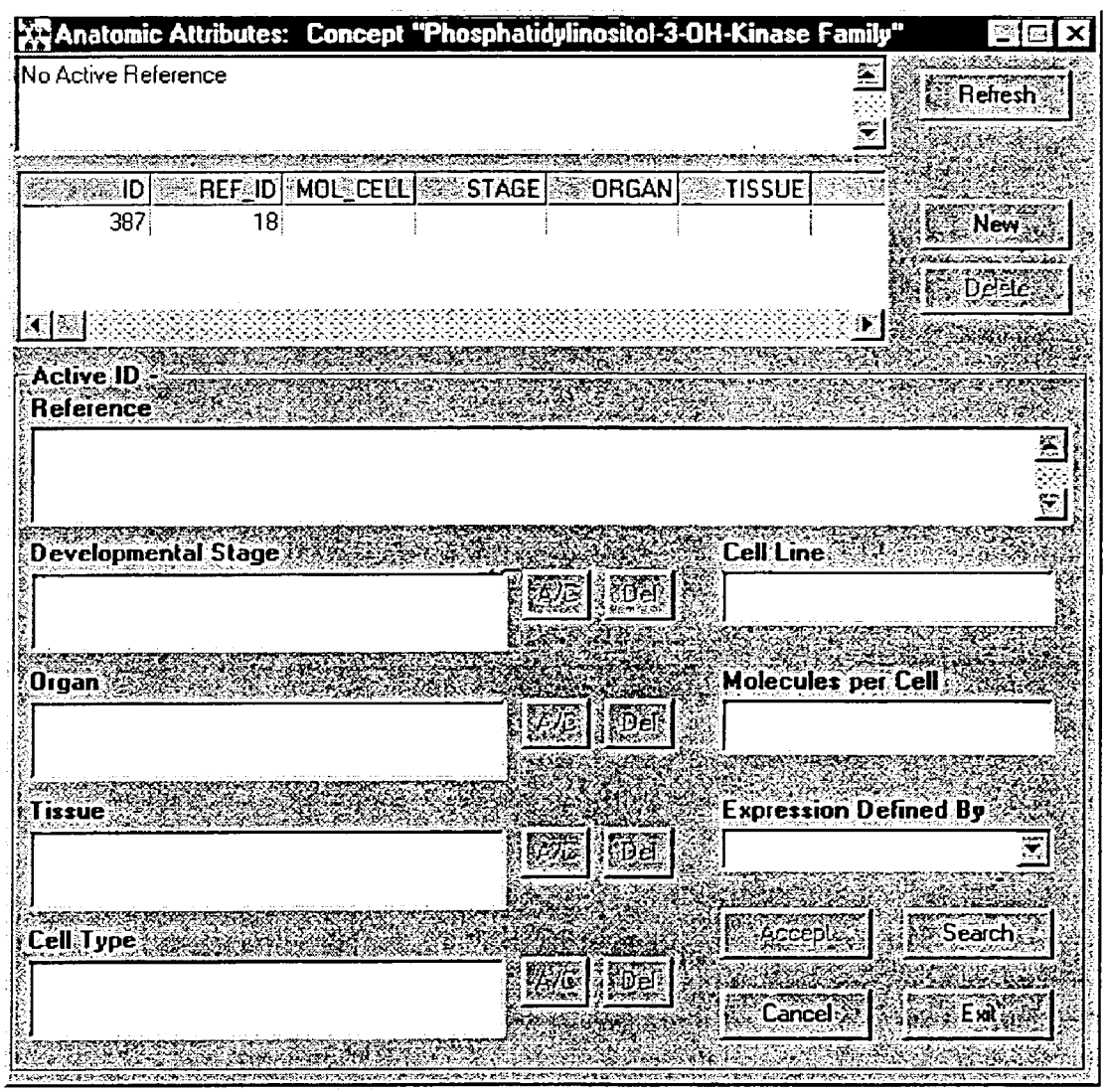
5330

5405        5400

5410

5420

SYSTEM AND METHOD FOR SIMULATING CELLULAR BIOCHEMICAL PATHWAYS

RELATED APPLICATIONS

Priority is claimed to U.S. Provisional Application No. 60/188,168, filed Mar. 10, 2000, and U.S. Provisional Application No. 60/244,694, filed Oct. 31, 2000, both of which are hereby incorporated by reference in their entirety.

FIELD OF THE INVENTION

The present invention relates to a system and method for examining pathways. In particular, the present invention provides a system and method for examining pathways that underlie cellular functions, specifically signal transduction pathways.

BACKGROUND OF THE INVENTION

DNA sequence analysis and recombinant DNA technology are powerful tools in biologic research. With advances in cellular biology, genetics, and computational methods, a deeper understanding of cell function and disease is emerging. A bulk of current research activity involves efforts to understand the molecular basis of cellular biochemical pathways, i.e., the ordered series of biochemical interactions (typically among proteins) that underlie diverse cellular functions. Greater understanding of these processes will foster more rational and effective design of medicinal therapies.

The recent completion of initial phases of several genome sequencing projects has provided important new resources for understanding cellular biochemical pathways and functions, but more detail is needed to fully understand many cellular functions. For instance, analysis of biochemical pathways, as well as gene and protein functions, are typically performed with complete knowledge of all the players known to be involved in the relevant cellular biochemical pathways. Thus, the ability to simulate cellular biochemical pathways and probable interaction partners for a protein under investigation would be desirable.

SUMMARY OF THE INVENTION

One aspect of the invention relates to the prediction of (a) functional properties of a protein, (b) potential interaction partners of the protein, and/or (c) potential target biochemical pathways within which the protein may interact. Thus, according to the invention, the influence of a given stimulus on a biochemical pathway can be assessed.

Another aspect of the invention relates to a system and method for simulating cellular biochemical pathways. The invention integrates the vast information available on cellular biochemical pathways to evaluate and predict the effect of given stimuli on cellular biochemical pathways. As such, the invention enables investigators working on poorly defined cellular biochemical pathways to simulate the biochemical pathway and predict potential protein interaction partners, in order to gain further insight into possible cellular biochemical pathways in which a target protein may function.

Another aspect of the invention is a system and method for demonstrating the signal cascades that occur in certain cells when certain stimuli are introduced. In an embodiment of the present invention, an inference engine linked to a database of known cellular components and reactions generates the signal cascades.

A further aspect is the incorporation into the system and method of the present invention of DNA sequence analysis of domains, motifs, and sites in new proteins of interest to enable a User to predict the most likely types of upstream and downstream proteins (or other biomolecules) with which a new protein might interact and, subsequently, the potential biochemical pathways within which a new protein might act. This aspect provides new advantages of significantly greater efficiency, confidence, and focus for a User in deciding on potential new avenues of research to pursue.

Another aspect of the system and method of the present invention is the incorporation of data regarding how the primary sequence of functional sites in biomolecules (eg., proteins) effects the specificity and efficacy of physical interactions with binding partners. Further, binding constants, rate equations, and reactant concentrations may be incorporated into the system and method of the present invention, in order to determine reaction events, pathway activities, and cell function outcomes.

The system and method of the present invention may also be used for molecular examination of the relationship between the structure of functional sites and partner interactions and their relation to the effects of molecular interventions by genetic variation, pharmaceutical compounds or toxic substances on the physical interactions of binding partners. Further, the present invention may be used to examine the functional consequences of such molecular interventions to biochemical pathways and cellular events. Examination, with the present invention, of the relationship between sequence variation (molecular genotype) within domains and functional profile within pathways creates new advantages for the design and selection of appropriate pharmaceutical compounds that are unlikely to produce adverse side effects, predicted by the subject genotypic profile.

In a preferred embodiment, the system and method of the present invention simulate signal cascades of cellular biochemical pathways that occur when certain stimuli or endpoints are introduced. Instead of using pre-generated biochemical pathways, the system and method of the present invention dynamically generate their results using a simulation module that includes an inference engine linked to at least one dynamic database of definitions relating to cellular concepts, components, and reactions.

In one embodiment of the present invention, a method for simulating at least one aspect of a cellular biochemical pathway is provided comprising the steps of: providing information regarding a target cellular environment and a stimulus event; simulating at least one aspect of a cellular biochemical pathway based on the stimulus event and target cellular environment information provided; and textually and/or graphically displaying at least one aspect of a cellular biochemical pathway. A method of the invention can further comprise the steps of predicting target protein functions and/or predicting potential target protein interaction partners.

In an embodiment of the present invention, a method for simulating at least one aspect of a cellular biochemical pathway is provided comprising the steps of: providing information regarding a target cellular environment and an endpoint; simulating at least one aspect of a cellular biochemical pathway based on the endpoint event and the target cellular environment information provided; and textually and/or graphically displaying at least one aspect of a cellular biochemical pathway.

In another aspect of the invention, a system for simulating at least one aspect of a cellular biochemical pathway is provided, comprising: a data input interface; a simulation module; and a display module. Based on cellular environment and input information provided to the data input interface, the simulation module simulates at least one aspect of a cellular biochemical pathway by determining the order of cellular events which occur within the defined cellular environment, and the display module can display textual and/or graphical representations of the simulated pathway. Input information may comprise information regarding cellular context, stimuli, knockouts and/or endpoints. The system of the present invention may optionally comprise a prediction module for predicting likely biological outcomes (e.g., apoptosis, lymphocyte activation, etc.), as well as protein interaction partners or gene interaction sites (for transcription factors) based on the simulated pathway(s).

In an embodiment of the present invention, the system and method of the present invention are adapted to be used as an aid in teaching, as educational tools, and/or as a complement to academic textbooks.

In another embodiment, the system and method of the present invention are adapted to be utilized by persons conducting genomic and proteomics research.

BRIEF DESCRIPTION OF THE DRAWINGS

FIGS. 3-43 are examples of various graphical displays that can be generated by the graphical user interface of FIG. 1B.

DETAILED DESCRIPTION OF THE PREFERRED EMBODIMENTS

Figure 1A:
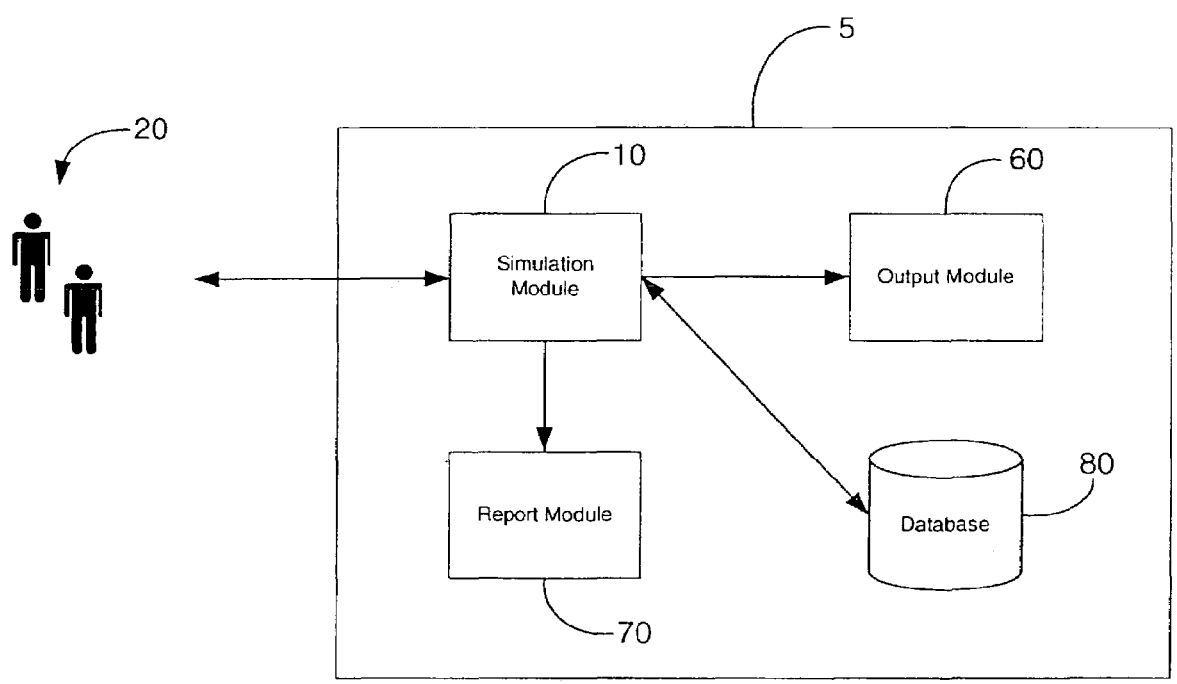
FIG. 1A is a block diagram of a system for simulating cellular biochemical pathways, in accordance with one embodiment of the present invention.

Cellular pathways involve molecular physical interactions between elements in series (typically, though not exclusively, proteins) leading to an outcome in a cellular process. Thus, a molecular understanding of these physical interactions, of pathway interconnections, and of pathway architectures would foster a more rational and effective design of pharmaceutical therapies when intervention is needed. Unfortunately, the identity of all the elements and all the interconnections in cellular pathways are not yet established. Gaps exist with respect to many of the elements and their functions. Thus, a major goal of research is to identify all elements of cellular pathways and to understand the molecular functions and interactions of these elements.

Central to this effort is the determination of the DNA sequence of genes that encode these proteins of interest. Examination and comparison of new DNA sequences with known gene DNA sequences stored in public databases routinely provides powerful predictive ability concerning the likely function of a new protein. Deeper examination of sequence data of new proteins can reveal the presence of various functional sites (e.g., domains, motifs, catalytic sites, and sites of biochemical modification), which typically constitute regions of physical interaction (e.g., protein-protein) between biomolecules. Many protein domains, motifs and sites have now been identified and the character of their involvement in diverse molecular interactions are known.

As used herein, the term "cellular biochemical pathway" generally refers to an ordered series of physical interactions between successive cellular elements leading to an outcome (e.g., signal transduction) in a cellular biochemical process.

Cellular environment information and input information can be provided to the data input interface in any manner known in the art, such as by manual data input through a keyboard or automated data importation.

Protein type information can be derived in any manner known in the art. For instance, a sequence similarity search can b performed, using public or commercial software programs, on a gene or protein sequence of interest. Typical similarity search platforms include the BLAST family of routines. Search routines such as BLOCKS, MoST, Pfam, PROSITE, or PROBE that detect conserved protein motifs can them be used if desired. Additional analysis of target protein structure, composition, and function can e done with a variety of web-based platforms.

As used herein, the term "cellular environment" generally refers to the sum total of all the substances and components within a cell under consideration. The provided cellular environment information, according to the present invention, represents at least a portion of the total cellular environment. Such cellular environment information is generally provided as cellular concepts and attributes, which are defined and described in more detail below. Cellular environment information may comprise, but is not limited to, cell type; protein type information, e.g., cell surface transmembrane receptor; sub-cellular location; identity of motifs; modification sites; and modification effects, e.g., activation, inhibition, etc. Input information may comprise information regarding stimuli, knockouts and endpoints.

A cellular "concept", as used herein, is an abstraction of anything that can be said to exist in space or occur over time with regard to a cellular environment. For instance, all cellular substances, cellular processes, and cellular components are "concepts". For example, in the statement "adenosine binds to an adenosine receptor in a liver cell, which leads to transcription", the concepts are "adenosine", "binds to", "adenosine receptor", "liver cell", "leads to" and "transcription". In grammatical terms, concepts usually represent nouns and verbs.

Figure 1B:
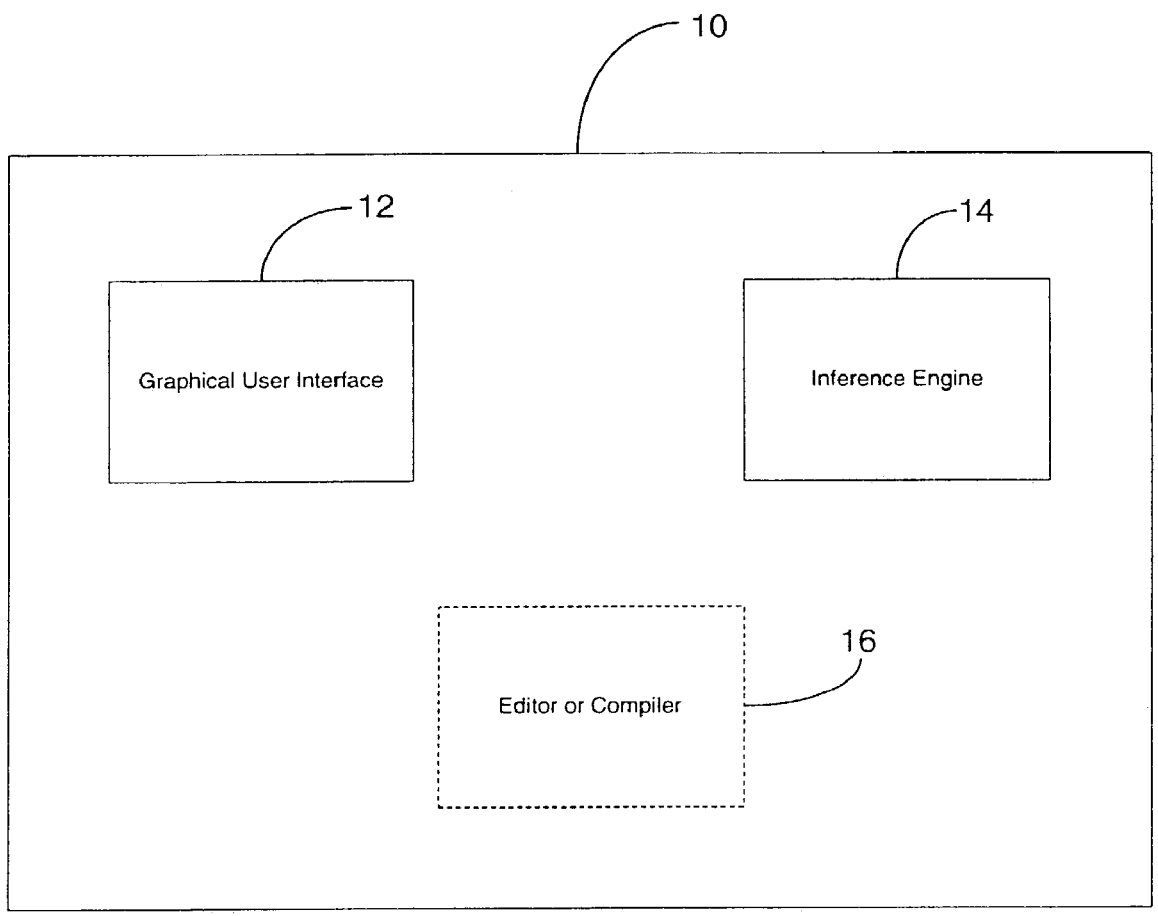
FIG. 1B is a block diagram of the simulation module of FIG. 1A, in accordance with one embodiment of the present invention.

FIGS. 1A and 1B are block diagrams of a system 5 for simulating cellular biochemical pathways, in accordance with one embodiment of the present invention. As shown in FIG. 1A, the system 5 comprises a Simulation Module 10, an Output Module 60, a Report Module 70 and a Database 80. The Simulation Module 10 is in communication with one or more Users 20, an Output Module 60, the Report Module 70, and the Database 80. The Simulation Module 10 contains all the processing logic for the system 5.

The system 5 of the present invention is preferably implemented on a server, which may be or include, for instance, a work station running the Microsoft Windows™ NT™, Windows™ 2000, UNIX, LINUX, XENIX, IBM, AIX, Hewlett-Packard UX™, Novel™, Sun Micro Systems Solaris™, OS/2™, BeOS™, Mach, Apache Open Step™, or other operating system or platform. However, the system 5 of the present invention could also be implemented on a programmed general purpose computer, a special purpose computer, a programmed microprocessor or microcontroller and peripheral integrated circuit elements, an ASIC or other integrated circuit, a hardwired electronic or logic circuit such as a discrete element circuit, a programmable logic device such as a FPGA, PLD, PLA, or PAL, or the like. In general, any device on which a finite state machine capable of implementing the modules and control routines discussed herein can be used to implement the present invention.

As shown in FIG. 1B, the Simulation Module 10 preferably comprises a Graphical User Interface 12 and an Inference Engine 14 and, optionally, an Editor or Compiler 16. In an embodiment of the present invention, the Graphical User Interface 12 of the Simulation Module 10 may gather input information from a User 20. A User 20 may provide several types of input to the Simulation Module 10 using any data input method known in the art. For example, a User 20 may provide pathway generation parameters to the Simulation Module 10. Further, new data requests may be entered by a User 20 through the Graphical User Interface 12 to the database 80. A User 20 may also input requests for information. Such a request may be entered using a dynamic display. The Simulation Module 10 may also receive input information from the Database 80.

The Inference Engine 14, working with the Database 80, evaluates a sequence of logic statements to determine which cellular events should be triggered based on the cellular environment present at the decision making moment.

As discussed above, the Simulation Module 10 may further comprise an Editor or Compiler 16. The Editor or Compiler 16 may be used by a User 20 to enter new definitions of attributes, concepts and events, to edit existing definitions and/or compile all changes to the Database 80. In a preferred embodiment, a User 20 may open the Database 80 for viewing. In a further embodiment, the User 20 may edit and/or compile attributes so that the results of the edited attributes may be used by the Inference Engine 14 of the Simulation Module 10. The User 20 may also edit and/or compile concepts so that the results of the edited concepts may be used by the Inference Engine 14 of the Simulation Module 10. Additionally, the User 20 may edit and/or compile events so that the results of the edited events may be used by the Inference Engine 14 of the Simulation Module 10. Optionally, a User 20 may be able to save files to the Database 80 using the Editor or Compiler 16 of the Simulation Module 10.

Several outputs may be generated by the Simulation Module 10. For example, requests for data by a User 20 may be sent to the Database 80 by the Inference Engine 14 of the Simulation Module 10. The Simulation Module 10 may generate a static graphical display via the Graphical User Interface 12. The static graphical display may be a display which shows the pathways created with the input information. For example, the static graphical display may be a "step down" or a "mass-action" diagram. This static graphical display or map may then be exported to the Output Module 60 and saved as a separate graphics format file. This graphics file format may be used as a visual aid by a User 20 conducting a presentation.

The Simulation Module 10 may also generate a dynamic graphical display of a "virtual cell" with the pathways that are created with the input information. This dynamic graphical display may be for forward pathway generation. The dynamic graphical display may also be a "virtual" three-dimensional cell. A User 20 may utilize the dynamic graphical display to navigate through the virtual three-dimensional cell. In this manner, the User 20 may look at different substances in the virtual three-dimensional cell as reactions occur. The User 20 may also zoom in and out of the cell and view the cell from different vantage points and perspectives.

The dynamic graphical display may also utilize pictures of cells, cell organelles and other pieces of the cell. These pictures may be, for example, from an image created with an electron microscope. In this manner, the dynamic graphical display provides a User 20 with a realistic presentation of the cell.

The Simulation Module 10 may additionally generate a written or textual display of the pathway interactions. Such a display may be generated in a display window. The Simulation Module 10 may also communicate information to the Output Module 60 to be used to generate further types of output or results. In a preferred embodiment of the present invention, the Output Module 60 creates a written display of the pathway interactions in a text file. Further, the Simulation Module 10 may communicate information to the Report Module 70 to be used to generate output reports.

The Database 80 preferably stores signal transduction information, which may originate from an operator of the System 5. The information may also originate from the input of a User 20. In a further embodiment, the information may originate from an outside database (not shown) which communicates information to the Database 80. The Database 80 also preferably stores the definitions of specific attributes, concepts, and events. Alternatively, the definitions of specific attributes, concepts, and events may be stored in a separate dynamic definitions database (not shown) that is either a stand-alone database or that is an integrated component of the Simulation Module 10. As an additional alternative, a base definitions database (nor shown) may be incorporated into the Simulation Module 10, and an extended definitions database (not shown) may be compiled and stored externally from the Simulation Module 10.

A User 20 may add new attributes to the Database 80. The Database 80 may also contain information regarding pathologies. This information may comprise signal transduction pathways, as well as different patterns of expression of all the components of the pathways (e.g., protein and DNA level information). For example, a User 20 of the Simulation Module 10 makes a query with a protein differentially expressed. In response, information, not only of the possible associated diseases, but also of the stage of a certain disease is preferably provided by the Simulation Module 10. Conversely, a search for a pathology or drug will preferably result in molecular information about that pathology or drug.

The Database 80 may also be coded with information specific to chemical areas which focus on signal transduction within plant or animal cellular environments. For example, the Database 80 may be coded with information specific to pesticides, herbicides, or fertilizers.

As discussed above, a concept is an abstraction of anything that can be said to exist in space or occur over time with regard to a cellular environment. A concept can "inherit" from other concepts, and they can contain other concepts. For example, a User 20 may create a concept of a "protein" and assign certain properties to a "protein" concept. If the User 20 wishes to create an instance of a protein (e.g., "TNF"), the User 20 may define the instance of the protein as a specific type of "protein" and that instance of the protein can inherit all the special properties of a "protein" without having to redefine all these properties a second time. In another example, a User 20 may define all the substances normally contained within mitochondria, and define a "mitochondria" concept that contains all these substance concepts. The User 20 may similarly define other cellular structures with their attending substances and then define a "cell" type to contain all these structures. In this manner, both a hierarchy of types and a hierarchy of structures may be established.

A User 20 may add new concepts to the Database 80. These concepts may be associated with various attributes. In an embodiment of the present invention, these attributes are necessary for efficient processing. For example, the attributes may provide information regarding the shape, color, size or location of a graphic. In a further embodiment, the attributes may be informational in nature. For example, the attributes may provide information regarding reference and species. These references may also be tracked by the Simulation Module 10 and exported to the Output Module 60 to facilitate the creation of footnotes, endnotes, articles or reports.

Concepts of the present invention are capable of being inherited from other concepts (e.g., a breast cancer cell inheriting from a generic cell). Concepts may also be capable of containing other concepts (e.g., generic cells containing a nucleus, mitochondria, etc.). Concepts may additionally be capable of excluding other concepts. Further, concepts may be capable of joining other concepts. In a preferred embodiment of the present invention, user input and editing of concept functions is facilitated through a concept wizard. A concept may also be selected by a User 20 to provide details as to the properties of the concept. For example, a User 20 may select a protein to provide the protein sequence with active sites, motifs, signal peptides, etc.

An event is a formal specification of a chemical reaction or process, in terms of (a) the reactants (i.e., what is required for the reaction to occur), (b) the products (i.e., what is produced by the reaction), (c) the inhibitors (i.e., what cannot be present for the reaction to occur), and (d) the context within which the reaction may or may not occur. In this manner, a process defined as a concept (e.g., "gene transcription") is distinguished from one defined as an event, as the event definition requires the pre-conditions and post-conditions of the process to be defined. For example, in the statement, "adenosine binds to an adenosine receptor in a liver cell which leads to transcription", the event is the entire statement, "adenosine" and "adenosine receptor" are the reactants, "gene transcription" is the product and "liver cell" is the context.

A User 20 may add new events to the Database 80 with specific concepts. Events may be associated with various attributes. These various attributes may be necessary for efficient processing (e.g., mobility) or may be informational in nature (e.g., reference and experimental conditions). Events may be capable of requiring the presence of certain concepts in the cellular environment before the event proceeds. Events may also be capable of applying certain concepts to events (e.g., binds, trimerizes, activates, etc.). Further, events may be capable of producing previously defined concepts. Events may additionally be capable of being inhibited by user-defined concepts. Events may also be able to specify within which mediums (e.g., cell types) the event may occur and may not occur. For example, the event could specify that the event occurs when contained in a breast cancer cell but not when contained in a liver cell. In a preferred embodiment of the present invention, user input and editing of event functions is facilitated through an event wizard, as will be explained in more detail below.

An attribute is a property of a concept or event. For example, an attribute of a concept may determine what color the Simulation Module 10 should draw the concept if it is represented on a computer screen. In another example, an attribute of an event may provide the Simulation Module 10 with information regarding the length of time the event requires to proceed. In an embodiment of the present invention, a User 20 may add new attributes to the Database 80. The attributes may comprise a decimal, enumeration (e.g., list), integer or text. Further, an attribute comprising a decimal or integer may further comprise upper and lower bounds. An attribute comprising an enumeration may further comprise user entered values.

The system may be used by one or more Users 20. In one embodiment of the present invention, the system is of a client-server nature capable of having multiple Users 20 simultaneously. In a further embodiment, Users 20 may enter data or input information into the Database 80 and allow the Simulation Module 10 to use that data or input information when generating simulations of various pathways.

In another embodiment of the present invention, a User 20 must supply a predefined user identification code and a corresponding password in order to access the system. The predefined user identification code may be used by the system during the interaction with the database by the User 20. In this embodiment, the User 20 may only be provided access to certain predefined areas of the Database 80 which correspond to the access level assigned to the User 20. The predefined user identification code may also be assigned to a group identification code that corresponds to another predefined access level. In addition, to access to certain predefined areas of the Database 80, the user or group identification code may also provide access to a second database (not shown). In this manner, the User 20 may have access to at least one database of information with the amount of access corresponding to a user or group identification code.

The Simulation Module 10 may generate a forward cell pathway. The forward cell pathway may be generated by prompting a User 20 to specify (a) the cell type where the simulation will be conducted and/or (b) the stimulus/stimuli (i.e., initiating event) for the event. The User 20 may also exclude certain events from or designate reaction endpoints for the forward cell pathway. These user inputs may be facilitated by an input interface. For example, the system may utilize a graphics user interface from which a User 20 may select from highlighted cell types, stimuli, reaction endpoints, or events for exclusion. The Inference Engine 14 of the Simulation Module 10 may process events to compare certain concepts of two or more different concepts to determine if an event should proceed.

As illustrated in FIG. 1A, the Simulation Module 10 utilizes information provided by the Database 80 and by Users 20. The Inference Engine 14 of the Simulation Module 10 then processes the information to predict pathways. In one embodiment of the present invention, the Inference Engine 14 may predict a biochemical signal transduction pathway, a small molecule metabolic pathway, a detoxification enzyme pathway (e.g., a P450 enzyme-mediated biotransformation to various metabolites), toxicology, acute phase reactions, or complement cascades (e.g., classical, alternate, and MBL). In another preferred embodiment of the present invention, the system of the present invention may generate diagrams, assist in interpreting the outcome of gene expression (i.e., functional genomics), and/or facilitate drug target identification or validation.

In another preferred embodiment, the system and method of the present invention may interface with microarrays to predict changes in the activity of biochemical pathways in response to diverse conditions. In this embodiment, the activities of biochemical pathways vary in response to altered conditions. For example, a common response to variation in the activity of biochemical pathways is a change in the expression of many target genes. In another example, variation in the amount of mRNA and the resultant effect on proteins made from the target genes contribute to changes in cell function.

In a further preferred embodiment, microarray chips provide an efficient means to rapidly survey quantitative changes in the expression of a large set of genes that result in response to changes in the activity of biochemical pathways. For example, the top proteins translated from the mRNAs expressed by the target genes in a given cell type under differing conditions could be rapidly detected on a chip. Further, a change in the amount of protein made by a gene would likely change the activity of the biochemical pathway in which the protein product functioned. In this manner, the information obtained from microarray chips may be imported to the Simulation Module 10 to evaluate how changes in the expression of large gene sets might change the activity of diverse biochemical pathways in response to varied conditions. Further, the Simulation Module 10 may be used to examine responses to many conditions such as response to presentation of pharmaceutical or toxic substances or the character of cell function under pathologic versus normal conditions (e.g., in a B lymphoma cell line verses a normal B cell).

Transcriptional (microarray) and translational (protein chip) data may be directly uploaded into the Database 80. The Inference Engine 14 of the Simulation Module 10 may infer potential signal transduction pathways at the global level and model the pathways. In a further embodiment of the present invention, the Simulation Module 10 contains sufficient data to not only reconstruct normal cellular pathways but also pathways associated with disease states. Expression data on gene products in biochemical pathways may also be input into the pathways generated by the Simulation Module 10. The pathways and interactions of drugs may be subsequently modeled and additional simulations may be generated regarding drug action on normal and diseased cells and/or organs. The Simulation Module 10 may also simulate signal transduction pathways at the cell level to provide output information regarding the role and physiological importance of new gene products or gene products with altered expression. Further, the present invention may identify intermediate signal transduction components as potential drug targets. In this embodiment, the list of possible or potential drug targets may also be expanded and reprocessed by the Simulation Module 10. In another preferred embodiment, the present invention simulates signal transduction pathways which are subsequently used to examine the therapeutic value and possible toxicities of drug candidates.

The system and method of the present invention may further comprise a high throughput screening system (not shown) or other automated assay testing device (not shown). This automated assay testing device would provide a User 20 with an automated method to perform simulated pathways in a laboratory.

The system and method of the present invention may also incorporate the co-joining of multiple cell types to form multi-functional tissues, the co-joining of tissues to form organs, and the co-joining of multiple organs to form organ systems. In this manner, the Inference Engine 14 of the Simulation Module 10 may predict whole body responses, via signal transduction modeling, to individual and multiple stimuli.

The system and method of the present invention may be used as an aid in teaching or educational tools, or as complement to academic text books. Academic institutions offering course work in the life sciences could benefit from using the system and method of the present invention as a powerful teaching and research tool. Students often comprehend difficult concepts better when they are presented in an interactive and visual manner. The system and method of the present invention provides static and dynamic pathway displays that can be used by educators to teach students about the complexities of the intracellular environment, including the interrelationships of multiple components and pathways. In addition, the present inventions' ability to incorporate new concepts and events can facilitate learning about the maturation of cells to fully differentiated states, the progression of disease processes like cancer in cells, and the interaction of pharmaceutical products with each other and cellular components.

In addition, the system and method of the present invention can easily be adapted to incorporate the specific concepts and events associated with other types of cellular-based organisms. Thus, for example, the system and method of the present invention can be used in the agricultural industry. The U.S. Department of Agricultural has initiated several national programs related to plant and animal production, product value, and safety through its Agricultural Research Service (ARS). ARS researchers in many of these national programs could benefit from using the system and method of the present invention, because their work also focuses on achieving a better understanding of intracellular interactions.

In an embodiment of the present invention, a User 20 may simulate assays using the systems and methods of the present invention. In a further embodiment of the present invention, the Database 80 and Inference Engine 14 may be accessed via an internet website. A User 20 may generate forward and reverse pathways through the internet website. Should a User 20 wish to physically run the simulated assays, the User 20 may obtain the necessary tools via hyperlinks corresponding to materials utilized in the simulation. For example, a User 20 may select a hyperlink corresponding to a concept or event and information may be presented regarding purchase information for assay kits or reagents. In a further embodiment, a User 20 may select a hyperlink corresponding to materials utilized in the simulation and the User 20 would be presented with a method of directly ordering the materials. For example, a User 20 may select a hyperlink corresponding to a concept or event and the User 20 may be presented with a transaction window from which the User 20 may purchase the assay kit or reagent.

Figure 2A:
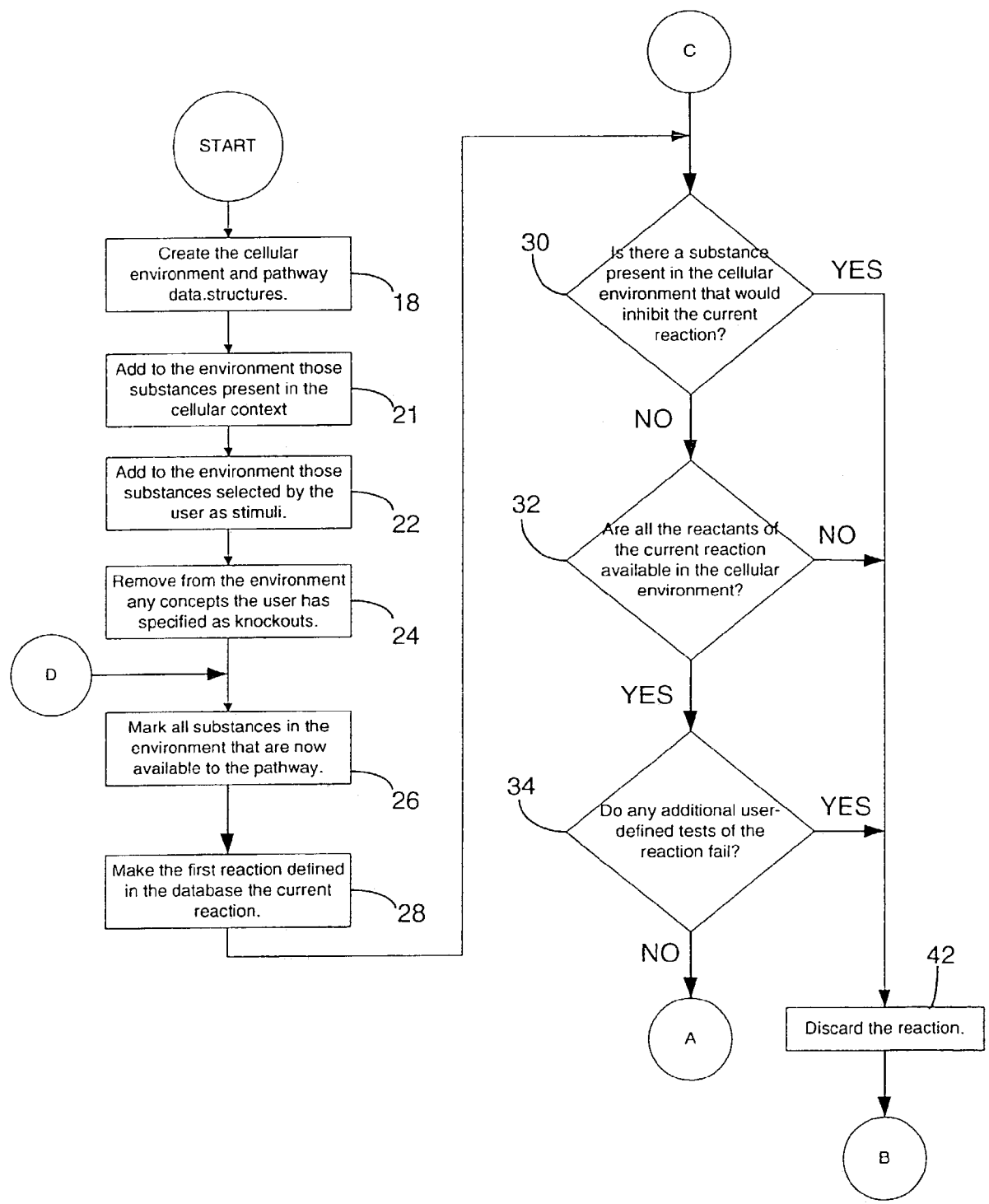
FIGS. 2A and 2B are a flow chart of a preferred control routine for a forward pathway generation function of the inference engine of FIG. 1B.

FIG. 2A is a flowchart of a preferred control routine for a forward pathway generation function of the Inference Engine 14 of FIG. 1B. The control routine begins at step 18, where the Inference Engine 14 accesses the Database 80 to create the cellular environment and pathway data structures. For example, the Inference Engine 14 may retrieve values and indicia corresponding to data implicated by the environment and pathway.

Control then continues to step 21, where those substances present in the cellular context are added to the environment. These substances may be determined based upon information stored in the Database 80. Then, at step 22, the substances selected by a User 20 as stimuli are added to the cellular environment and pathway data structures. Control then continues to step 24.

At step 24, any concepts that a User 20 has specified as "knockouts" are removed from the cellular environment and pathway data structures. Control then continues to step 26, where all substances in the cellular environment that are determined to be currently available to the pathway are marked.

Next, at step 28, the first reaction defined in the database is designated as the current reaction. Control then continues to step 30, where it is determined whether there is a substance present in the cellular environment that would inhibit the current reaction. If there is, control jumps to step 42, where the reaction is discarded and control continues to step 46. Otherwise, control continues to step 32.

At step 32, it is determined whether all the reactants of the current reaction are available in the cellular environment. If not all the reactants are available, control jumps to step 42. Otherwise, control continues to step 34.

At step 34, it is determined whether any additional user-defined tests of the reaction fail. If so, control jumps to step 42. Otherwise, control continues to step 36, where the Inference Engine 14 adds the reaction to the sequence of events that make up one, or more, of each cellular pathway.

Next, at step 38, the Inference Engine 14 adds the products of the reaction to the environment and uses the reaction duration to show relative process time of the products. Control then continues to step 46, where the Inference Engine 14 determines if all the reactions have been tested. If not, control jumps to step 44. Otherwise, control continues to step 50.

At step 50, the Inference Engine 14 identifies whether any endpoints defined by the User 20 have been reached. If so, the control routine ends. Otherwise, control continues to step 52.

At step 52, the Inference Engine 14 determines whether all the substances in the cellular environment have been activated. If so, the control routine ends. Otherwise, control jumps to step 26.

At step 44, the next reaction defined in the Database 80 is designated as the current reaction. Control then jumps to step 28.

Figure 2B:
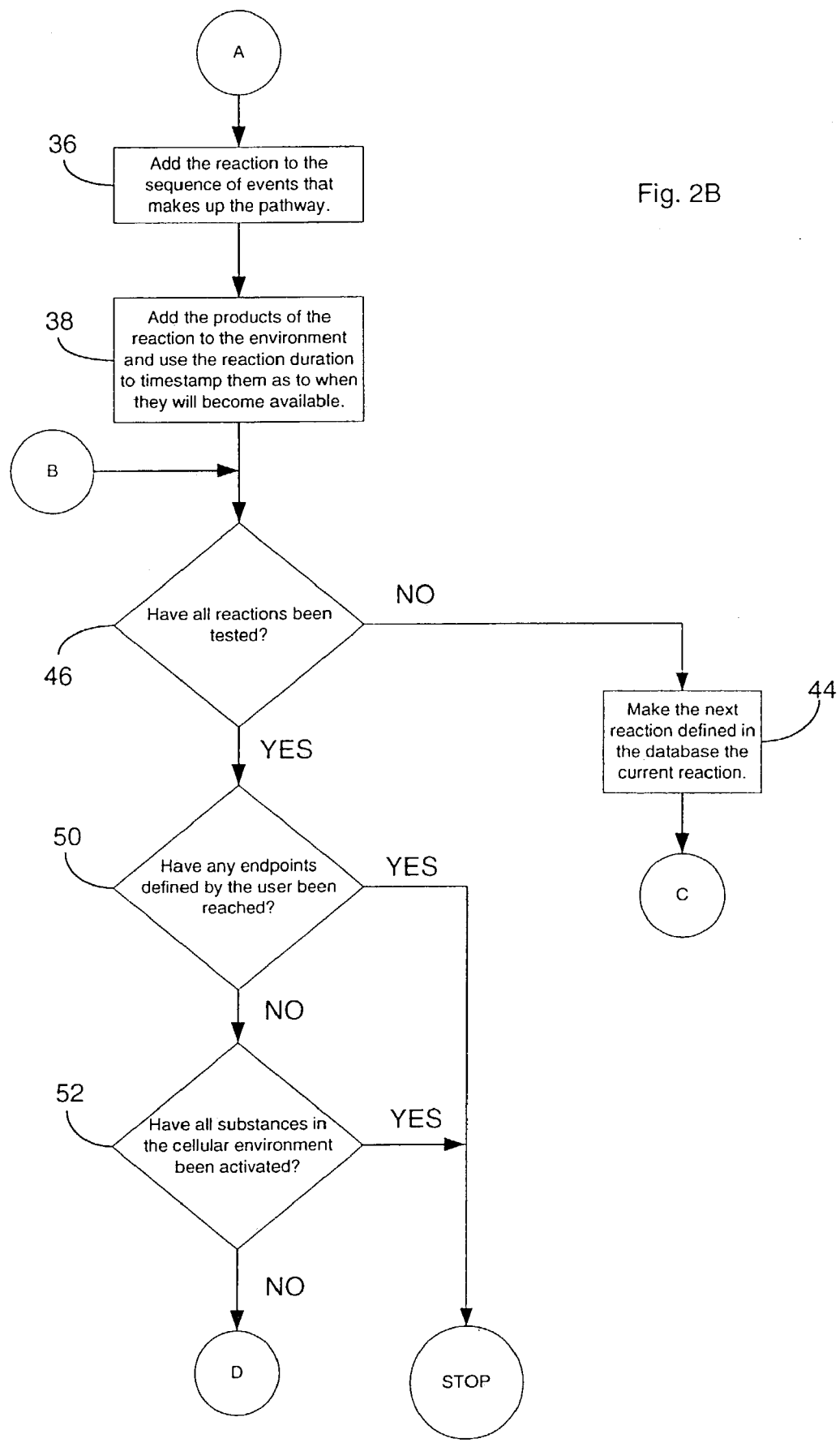
Figure 2C:
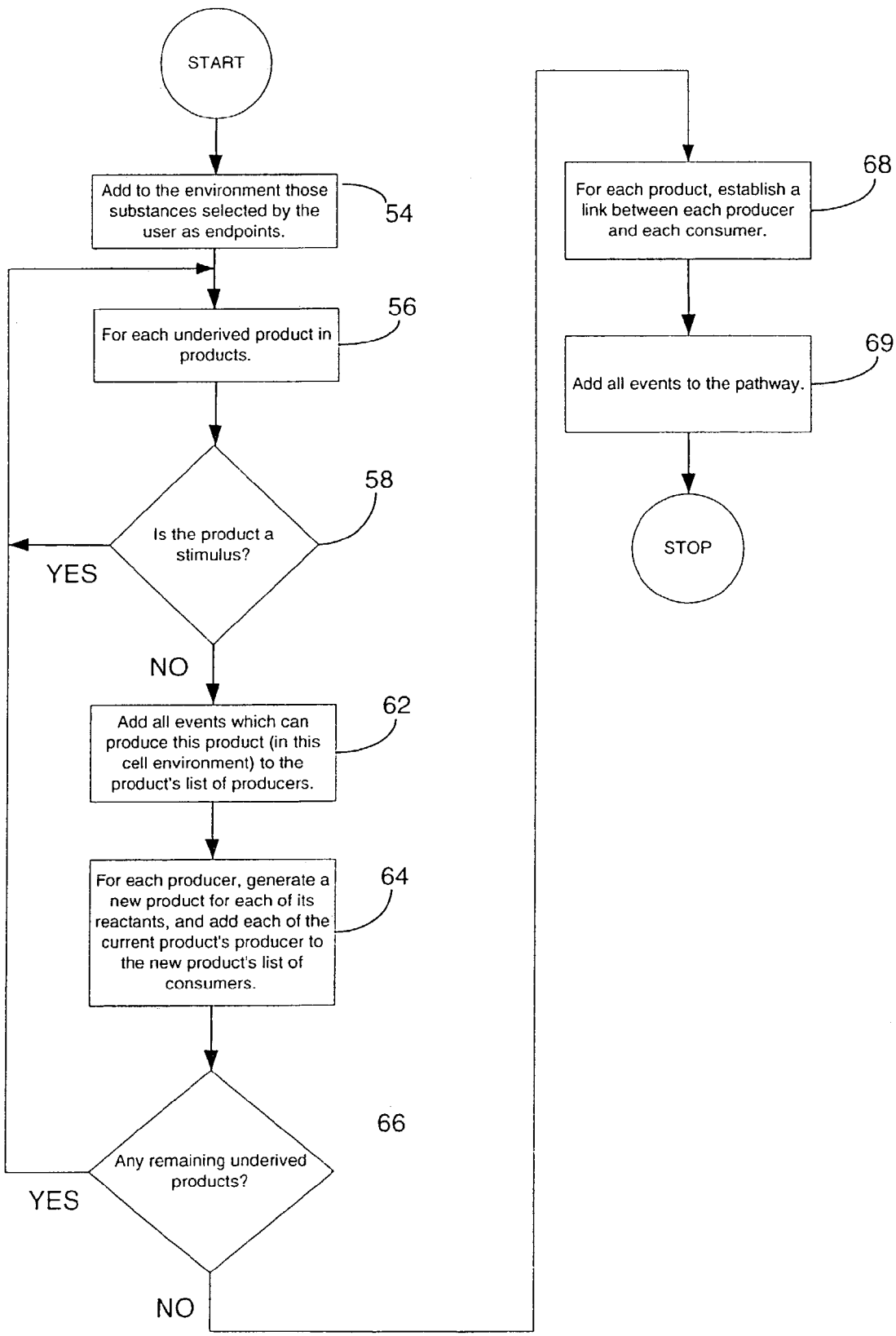
FIG. 2C is a flow chart of a preferred control routine for a reverse pathway generation function of the inference engine of FIG. 1B.

FIG. 2B is a flowchart of a preferred control routine for a reverse pathway generation function of the Inference Engine 14 of FIG. 1B. The method begins at step 54, where the Inference Engine 14 accesses the Database 80 to add to the environment those substances selected by the user as endpoints. Control then continues to step 56, where the Inference Engine 14 identifies each underived product in the products.

Next, at step 58, for each underived product identified in step 56, the Inference Engine 14 determines whether the product is a stimulus. If so, control returns to step 56. Otherwise, control continues to step 62.

At step 62, all events in the particular cellular environment which may produce the identified stimulus product are added to the product's list of producers. Control then continues to step 64, where, for each producer, a new product is generated for each of the corresponding reactants. Each of the current product's producers is subsequently added to the new product's list of consumers. Control then continues to step 66.

At step 66, it is determined whether there are any remaining underived products. If so, control jumps back to step 56. Otherwise, control continues to step 68.

At step 68, a link between each producer and each consumer is established for each product. Control then continues to step 69, where all events are added to the pathway. The control routine then ends.

In one embodiment of the invention, the definitions are stored in the Database 80 in a binary format, an editable textual format, or a combination of both. The editable textual format preferably comprises a descriptive computer language called Signal Transduction Language ("STL"), which is one aspect of the present invention. The definitions may be generated using STL, and/or compiled into a binary format in any manner known in the art. In a preferred embodiment of the invention, definitions of attributes, concepts, and events are created, and cellular biochemical pathways are simulated using a set of graphics-based forms (i.e., instructive, step-by-step screens) generated by the Simulation Module 10. In an alternate preferred embodiment, a set of graphics-based forms are generated by the Output Module 60. Alternatively, definitions and simulations may be created through a direct, text-based interface using an STL shell.

Figure 3:
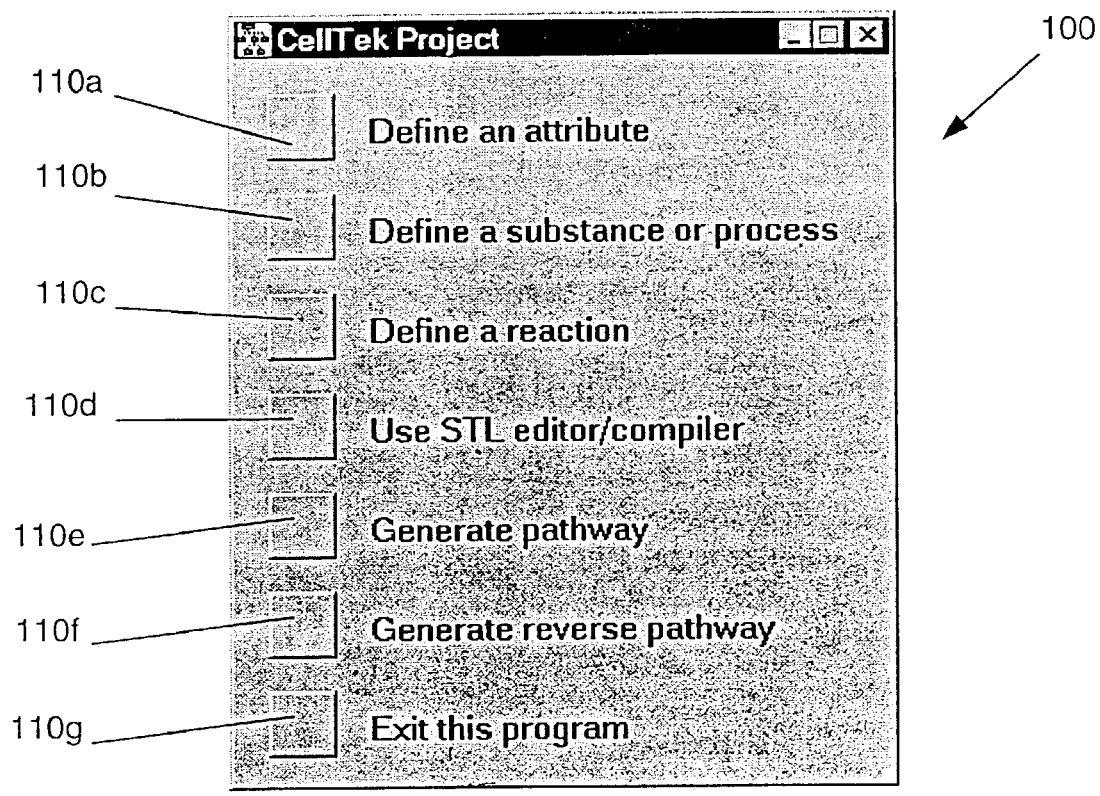

As described above, in one embodiment of the present invention, the Graphical User Interface 12 may be implemented with graphics-based forms. In this embodiment, upon initiating the Simulation Module 10, a User 20 may be presented with a main menu 100, an example of which is shown in FIG. 3. To perform an action, the User 20 may select one of a plurality of user action buttons 110a-112g. Each of the user action buttons 110a-110g may be associated with one of a plurality of Simulation Module functions. In the main menu 100 shown in FIG. 3, user action buttons 110a-112g may be associated with the Simulation Module functions Define an Attribute; Define a Substance or Process; Define a Reaction; Use STL Editor/Compiler; Generate Pathway; Generate Reverse Pathway; and Exit Program, respectively.

Selecting the Define an Attribute button 110a initiates an Attribute Forms series, which is a series of screens that allows the User 20 to define a new attribute. Selecting the Define a Substance or Process button 110b initiates a Concept Forms series, which is a series of screens that allows the User 20 to define a new concept. Selecting the Define a Reaction button 110c initiates an Event Forms series, which is a series of screens that allows the User 20 to define a new event. Selecting the Use STL Editor/Compiler button 110d initiates an STL shell, which allows the User 20 to directly edit and compile the textual definitions. Selecting the Generate Pathway button 110e or Generate Reverse Pathway button 110f initiates a Pathway Forms series, which is a series of screens that allows the User 20 to initiate the Inference Engine 14 and simulate at least one aspect of a cellular biochemical pathway. Finally, selecting the Exit this Program button 110g shuts down the Simulation Module.

Attribute Forms Series

Figure 4A:
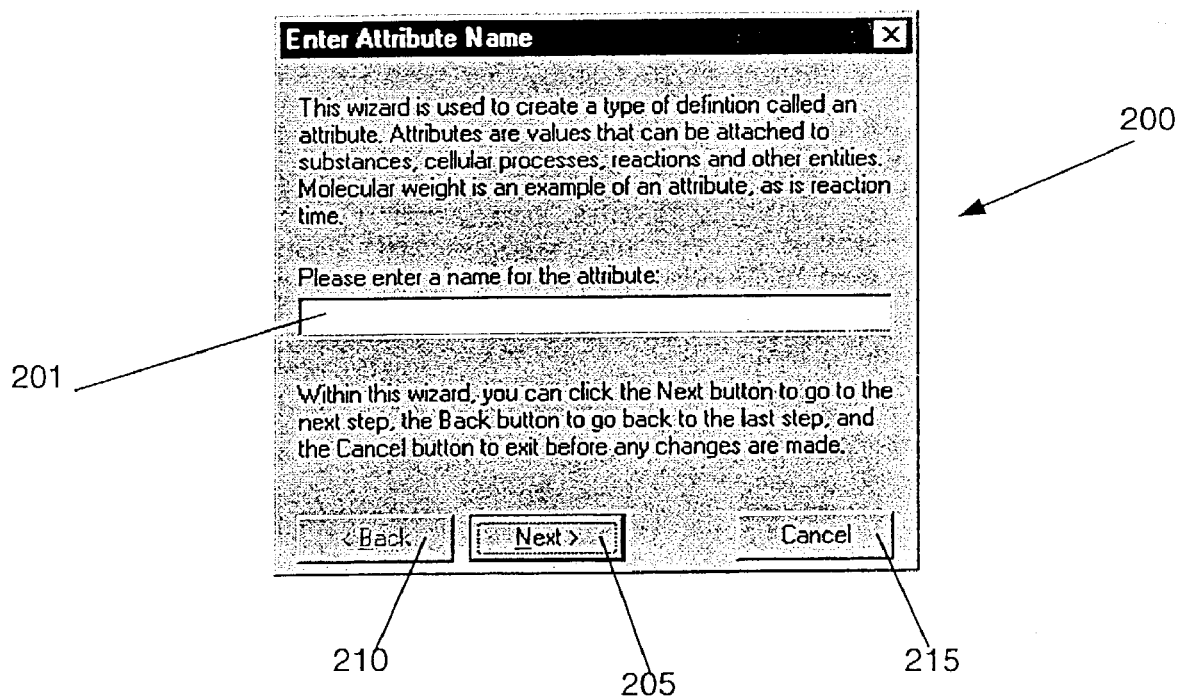

When a User 20 initiates the Attribute Forms series from the main menu 100 by selecting the Define an Attribute button 110a, an Attribute Name screen 200, an example of which is shown in FIG. 4A, may be displayed. As shown in FIG. 4A, a User 20 may have the option of entering an attribute name in field 201 and then selecting the Next button 205 to proceed to the next step in the Attribute Forms series. Alternatively, a User 20 may select the Cancel button 215 to exit the Attribute Forms series. It should be noted that user input in field 201 may determine the step that comes "next" in the Attribute Forms series.

Figure 4B:
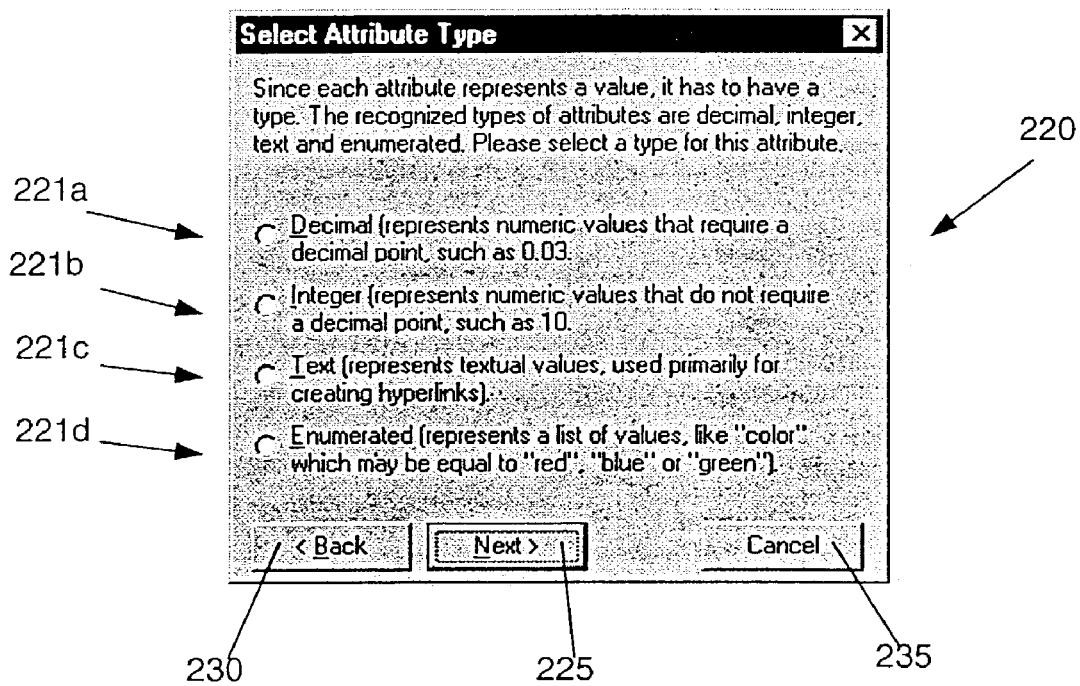

Entering an attribute name in field 201 and clicking the Next button 205 may initiate a Select Attribute Type screen 220, an example of which is shown in FIG. 4B. As shown in FIG. 4B, the Select Attribute Type screen 220 may allow a User 20 to select one of four types of attributes: Decimal 221a; Integer 221b; Text 221c; or Enumerated 221d. A User 20 may select one of the attribute types and then select the Next button 225 to proceed to the next step of the Attribute Forms series. Alternatively, a User 20 may select the Back button 230 to return to the previous screen or the Cancel button 235 to exit the Attribute Forms series.

Figure 4C:
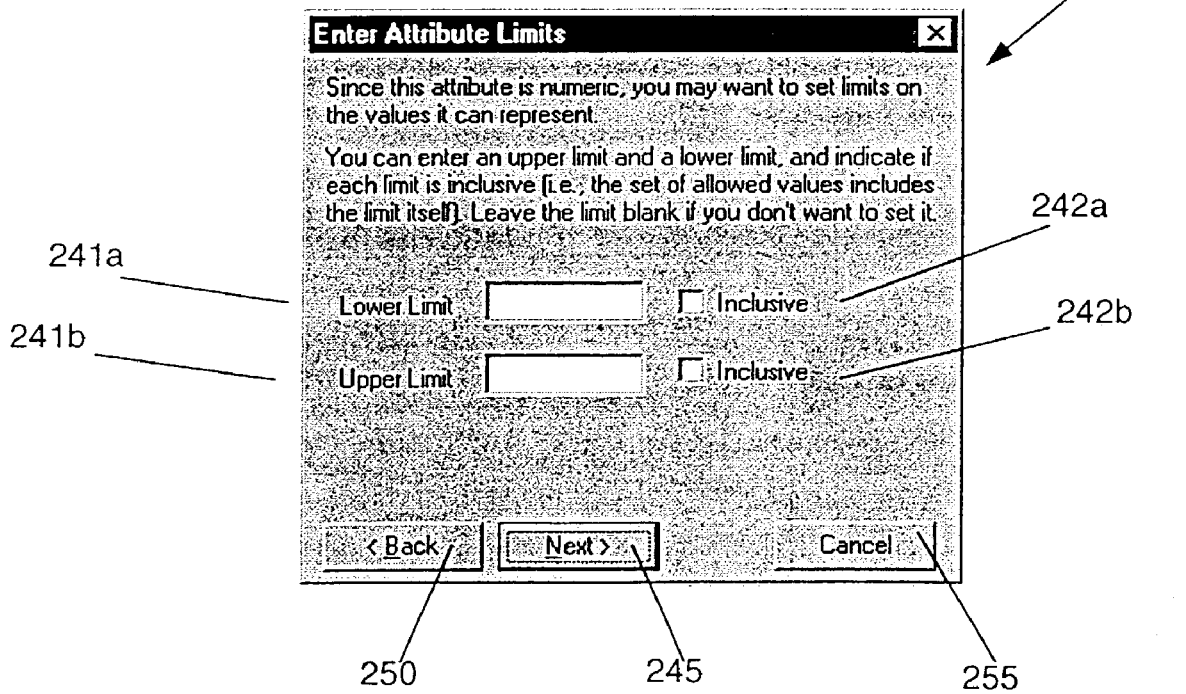

If a User 20 selects Decimal 221a or Integer 221b, followed by the Next button 225, the Enter Attribute Limits screen 240, an example of which is shown in FIG. 4C, may be displayed. As shown in FIG. 4C, a User 20 may enter numeric attribute values, through the Enter Attribute Limits screen 240, that represent an upper limit 241b and a lower limit 241a for this attribute. Each of the numeric attribute limits may be made inclusive by selecting a respective Inclusive indicator 242a and 242b. A User 20 may select the Next button 245 to proceed to the next step of the Attribute Forms series, the Back button 250 to return to the previous screen, or the Cancel button 255 to exit the Attribute Forms series.

Figure 4D:
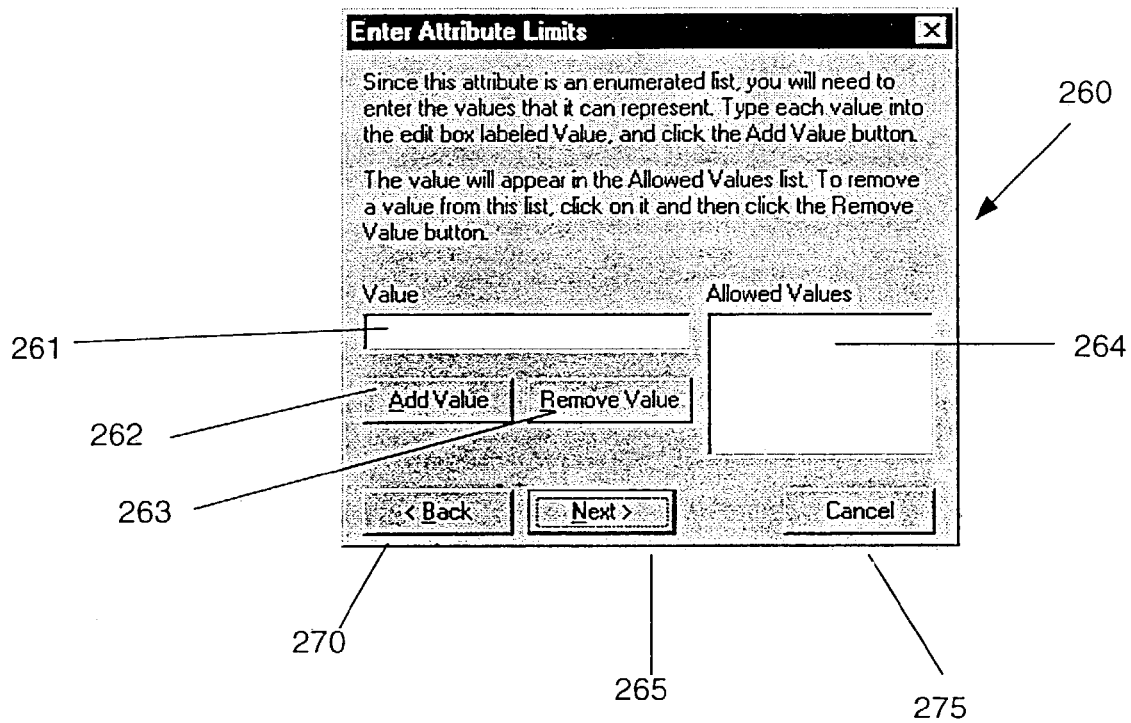

Referring back to FIG. 4B, if a User 20 selects Enumerated 221d from the Select Attribute Type screen 220, followed by the Next button 225, the Enumerated Enter Attribute Limits screen 260, an example of which is shown in FIG. 4D, may be displayed. As shown in FIG. 4D, a User 20 may enter all possible values of an enumerated list. For example, the values represented by a "cellular location" type of attribute may be entered by typing the text "membrane bound" into the Value field 261, clicking the Add Value button 262, then repeating the process for any other values represented by the attribute, e.g., "extracellular", "nuclear", etc. Values that have been added may appear in the Allowed Values list 264. From the Enumerated Enter Attribute Limits screen 260, a User 20 may also remove a value from the Allowed Values list 264 by selecting the value from the Allowed Values list 264 and then selecting the Remove Value button 263. A User 20 may select the Next button 265 to proceed to the next step of the Attribute Forms series, the Back button 270 to return to the previous screen, or the Cancel button 275 to exit the Attribute Forms series.

Figure 4E:
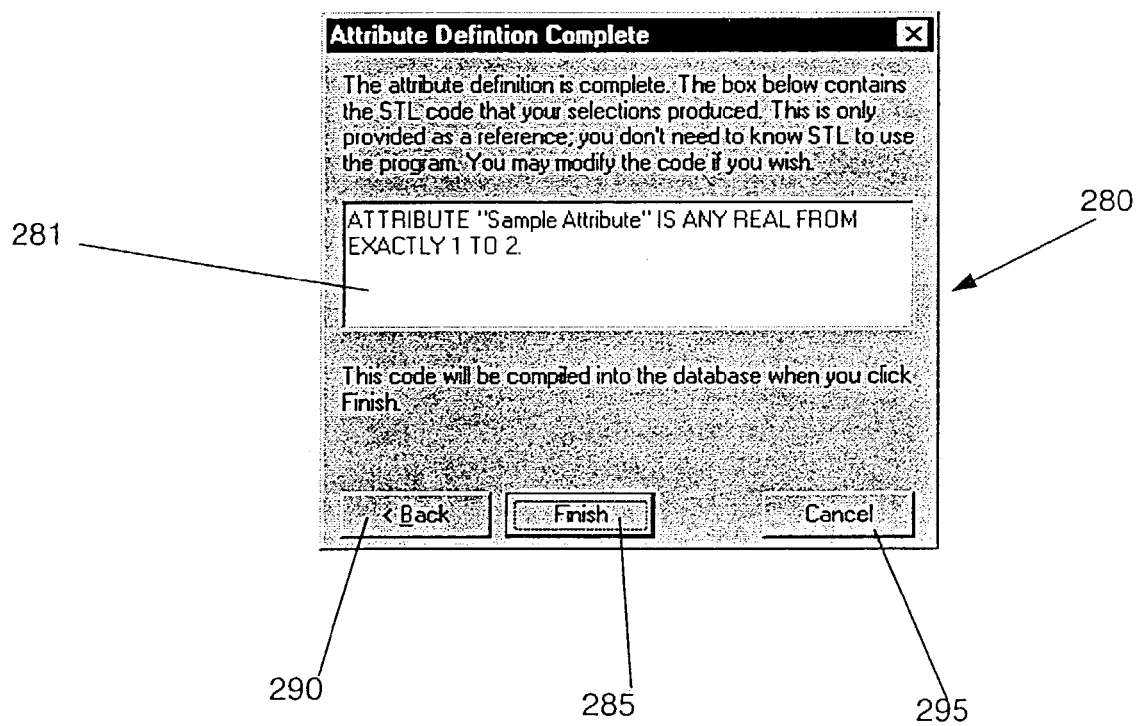

Upon selecting the Next button 265 from the Enumerated Enter Attribute Limits screen 260 (FIG. 4D), the Next button 245 from the Numeric Enter Attribute Limits screen 240 (FIG. 4C), or Text 221c from the Select Attribute Type screen 220 (FIG. 4B), the Attribute Definition Complete screen 280, an example of which is shown in FIG. 4E, may be displayed. As shown in FIG. 4E, the Attribute Definition Complete screen 280 may show, in field 281, the STL code that was produced from user selections within the Attribute Forms series. In the example shown in FIG. 4E, "Sample Attribute" was entered as an attribute name in field 201 (FIG. 4A), the type selected was Decimal 221a (FIG. 4B), a value "1" was entered as the lower limit 241a, and a value of "2" was entered as the upper limit 241b (with the inclusive indicators 241a and 242b checked). As shown in FIG. 4E, from the Attribute Definition Complete screen 280, a User 20 may select the Finish button 285 to enter the attribute definition into at least one dynamic database of definitions. A User 20 may optionally select the Back button 290 to return to the previous screen, or may select the Cancel button 295 to exit the Attribute Forms series.

Concept Forms Series

Figure 5A:
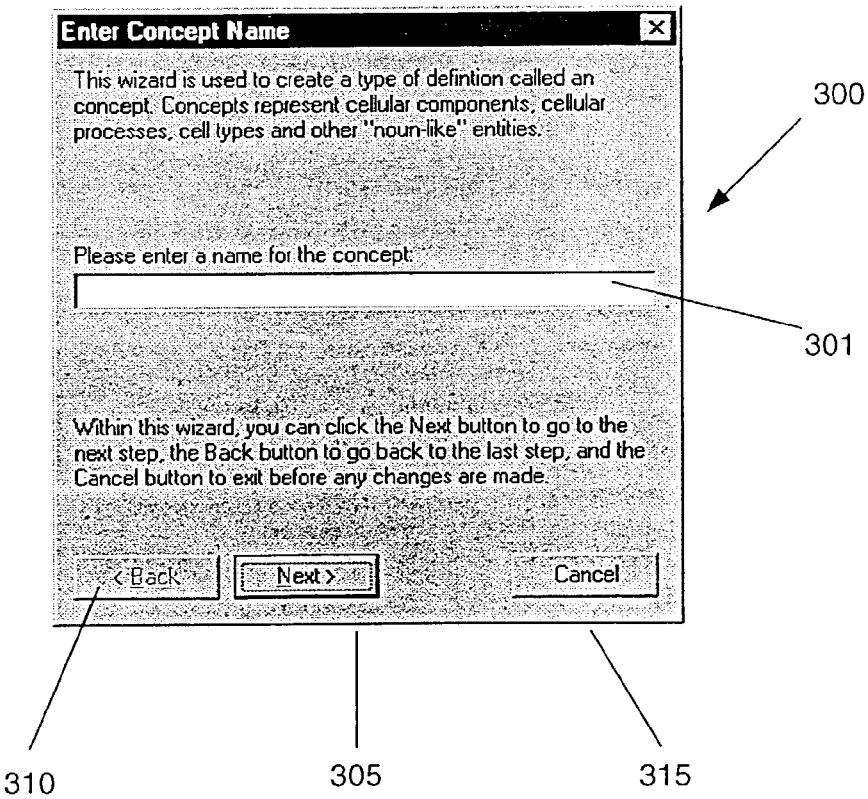

When a User 20 initiates the Concept Forms series from the main menu 100 by selecting the Define a Substance or Process button 110b (FIG. 3), a Concept Name screen 300, an example of which is shown in FIG. 5A, may be displayed. As shown in FIG. 5A, a User 20 has the option of entering a concept name in field 301, and then selecting the Next button 305 to proceed to the next step of the Concept Forms series. Alternatively, a User 20 may select the Cancel button 315 to exit the Concept Forms series. It should be noted that user input in field 301 may determine the subsequent step in the Concept Forms series.

Entering a concept name in field 301 and clicking the Next button 305 may initiate the Select a Base Concept screen 320, an example of which is shown in FIG. 5A. The Select a Base Concept screen 320 may allow a User 20 to select a base concept from which a newly named concept will inherit attributes. This is especially useful in defining reactants and products of reactions. For example, in the reaction "A phosphorylates B", the User 20 may define "A" and "B" using "protein" as the base concept. The concept "phosphorylated B" can then be defined using "B" as the base concept. A concept does not require a base concept. However, a User 20 may select one or more base concepts and then select the Next button 325 to proceed to the next step of the Concept Forms series. Alternatively, a User 20 may select the Back button 330 to return to the previous screen or the Cancel button 335 to exit the Concept Forms series.

Figure 5B:
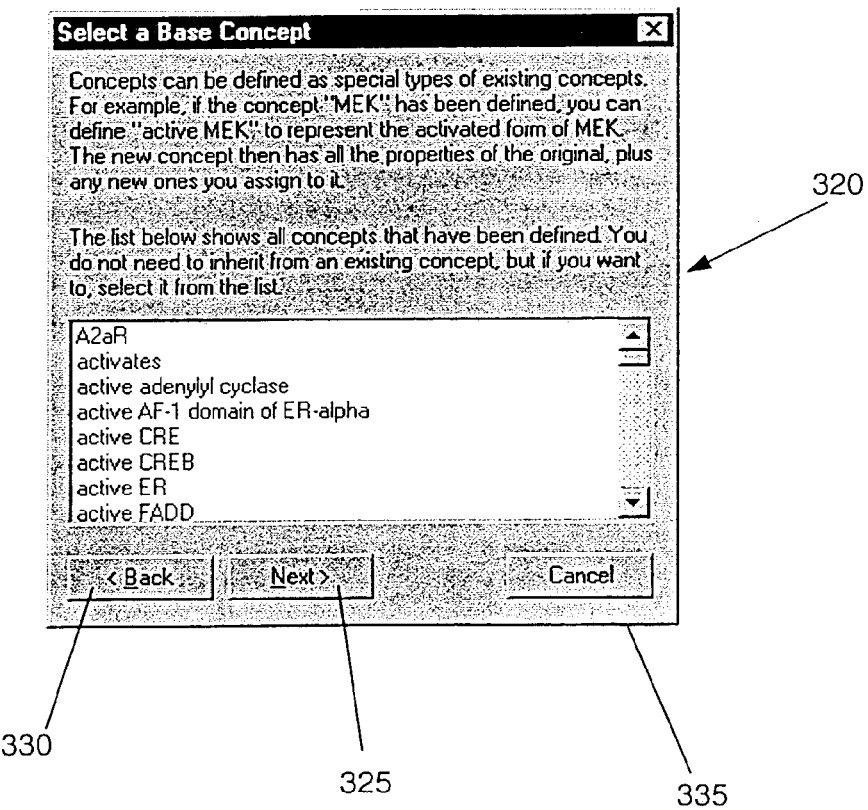
Figure 5C:
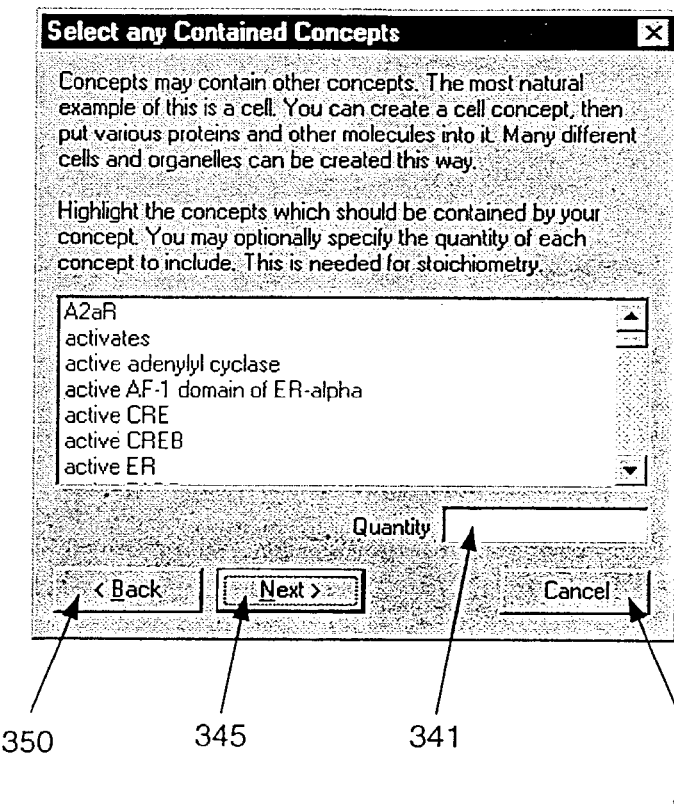

Upon selecting the Next button 325, the Select Any Contained Concepts screen 340 may be displayed, an example of which is shown in FIG. 5C. The Select Any Contained Concepts screen 340 allows a User 20 to select one or more concepts which the concept named in the Select a Base Concept screen 320 (FIG. 5B) is to contain. This feature may be used to create a "cell" or some other general cellular environment. As defined and described in more detail below, the concepts that are contained in a given cellular environment are assumed to be "available" to any biochemical pathway that involves the contained concepts.

Referring to FIG. 5C, if more than one of a selected contained concept is present within a given cellular environment, upon selecting the concept, the number present may be entered in Quantity field 341. For example, a cell which includes a TNFR receptor complex may be defined as containing three TNFR concepts. A User 20 may select one or more contained concepts, enter the number of individual concepts contained in Quantity field 341, and then select the Next button 345 to proceed to the next step of the Concept Forms series. Alternatively, a User 20 may select the Back button 350 to return to the previous screen or the Cancel button 355 to exit the Concept Forms series.

Figure 5D:
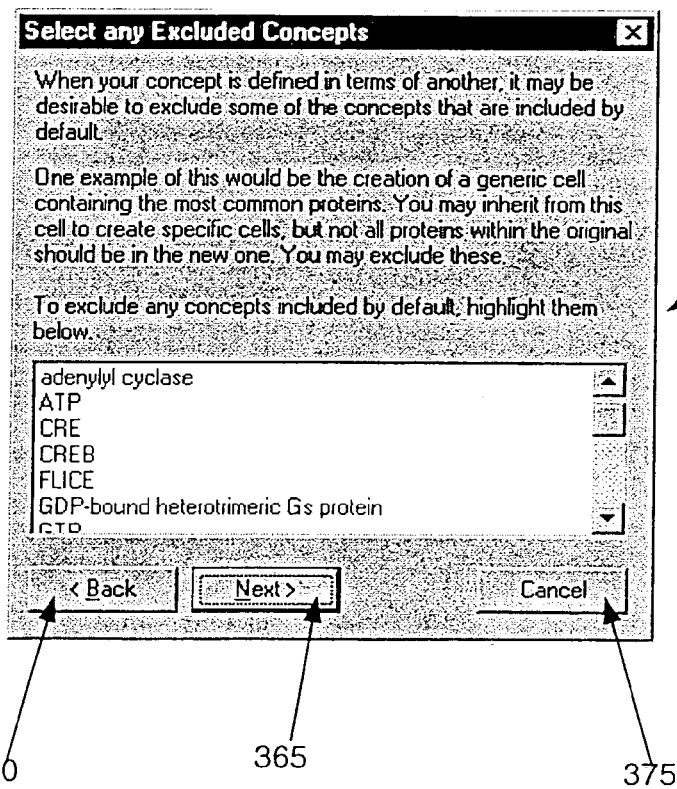

Upon selecting the Next button 345 (FIG. 5C), the Select any Excluded Concepts screen 360 may be displayed, an example of which is shown in FIG. 5D. The Select any Excluded Concepts screen 360 displays all concepts contained by the base concept, and thus is only utilized when a newly named concept inherits features from existing concepts. This Select any Extended Concept screen 360 is used to exclude specific concepts from the overall cellular environment. Again, a User 20 may select the Next button 365 to proceed to the next step of the Concept Forms series, the Back button 370 to return to the previous screen, or the Cancel button 375 to exit the Concept Forms series.

Figure 5E:
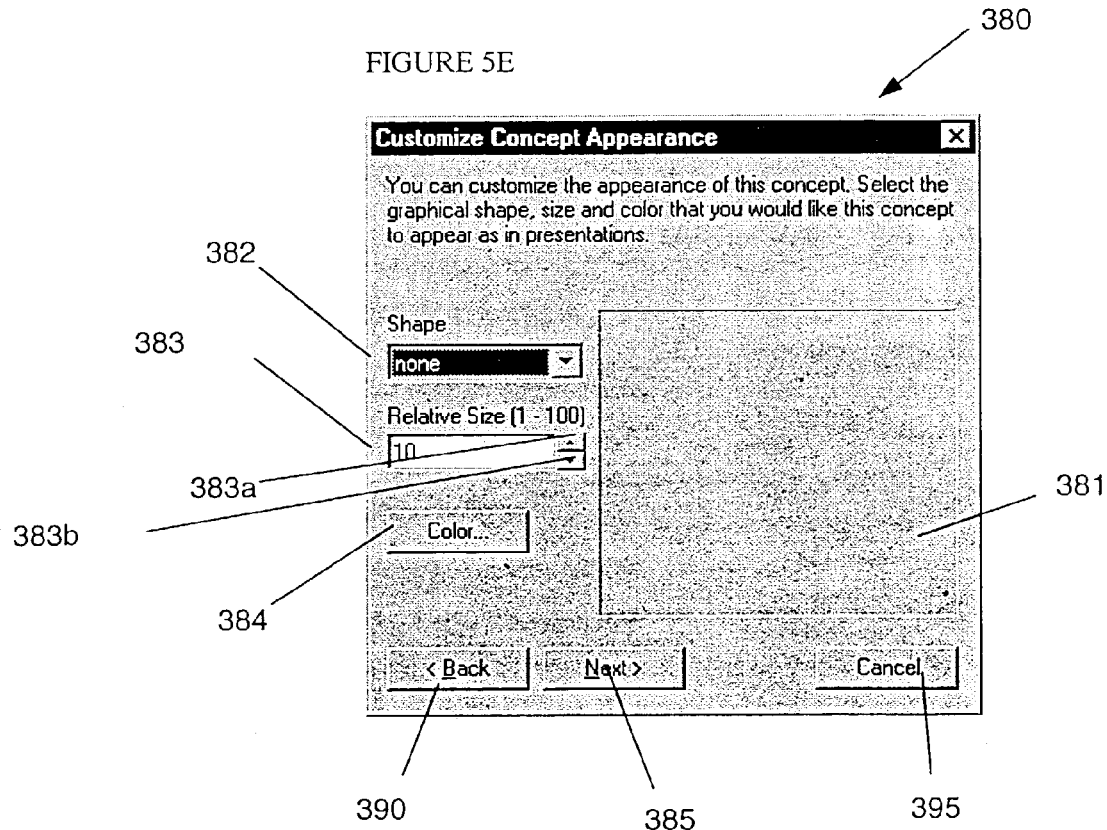

Upon selecting the Next button 365, if the newly named concept includes the "substance" attribute (which is true for the "substance" concept or any of its inherited concepts, like "protein"), the Customize Concept Appearance screen 380 may be displayed, an example of which is shown in FIG. 5E. The appearance of the concept's graphical presentation may be customized in the Customize Concept Appearance screen 380. The shape of the concept graphic may be selected from the Shape Box 382. The relative size of the concept graphic can be selected in the Relative Size Box 383, or the up and down buttons 383a and 383b may be used to increase or decrease the relative size incrementally. The color of the concept graphic may be selected by selecting the Color button 384. View Box 381 may show the concept as it will appear, and may be updated after ever, change. A User 20 may select the Next button 385 to proceed to the next step of the Concept Forms series, the Back button 390 to return to the previous screen, or the Cancel button 395 to exit the Concept Forms series.

Figure 5F:
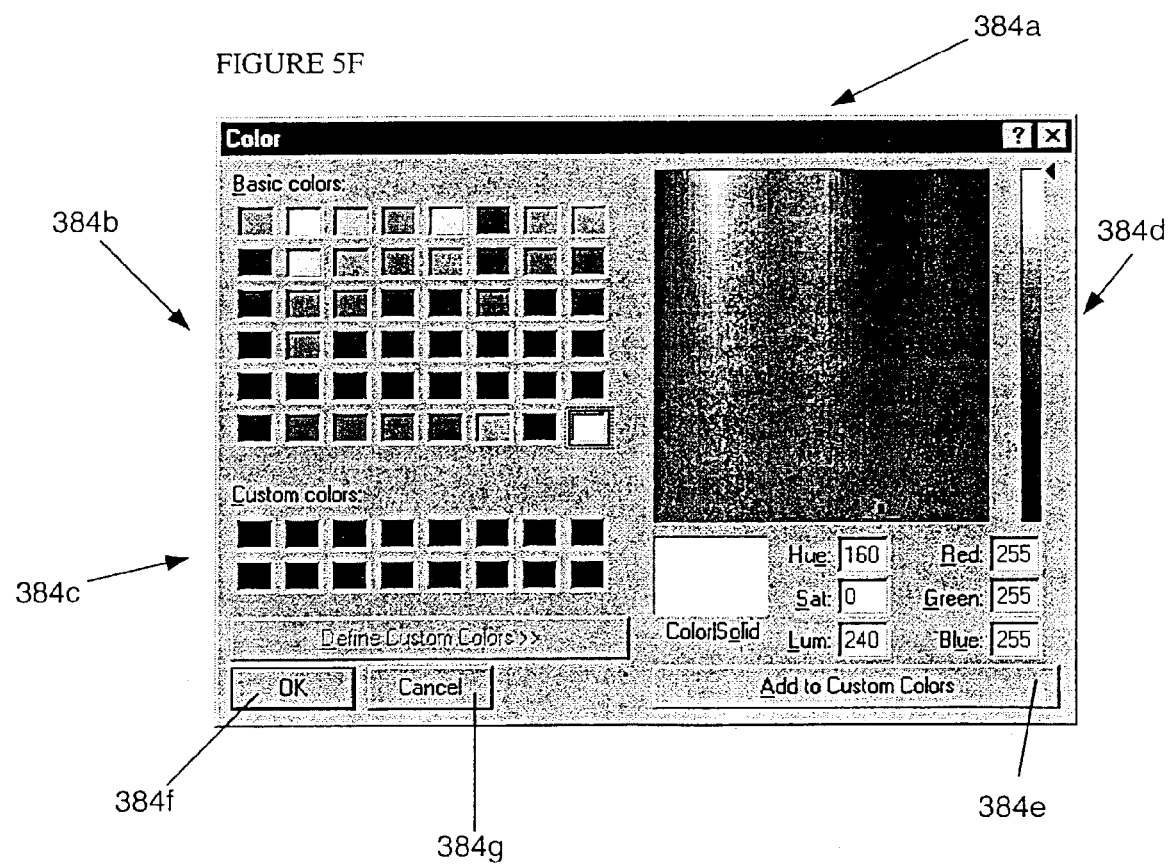

When the Color button 384 is selected, a standard Windows® color palette screen 384a may be displayed, an example of which is shown in FIG. 5F. A basic color may be selected from the Basic Colors palette 384b, or a custom color may be defined in the Custom Colors palette 384c by manipulating parameters of Color Diagram 384d and selecting the Add button 384e. Once the color is selected, the OK button 384f may be selected to return to the Customize Concept Appearance screen 380 of the Concept Forms series. Alternatively, the Cancel button 384g may be selected to return to the Customize Concepts Appearance screen 380 without defining a color.

Figure 5G:
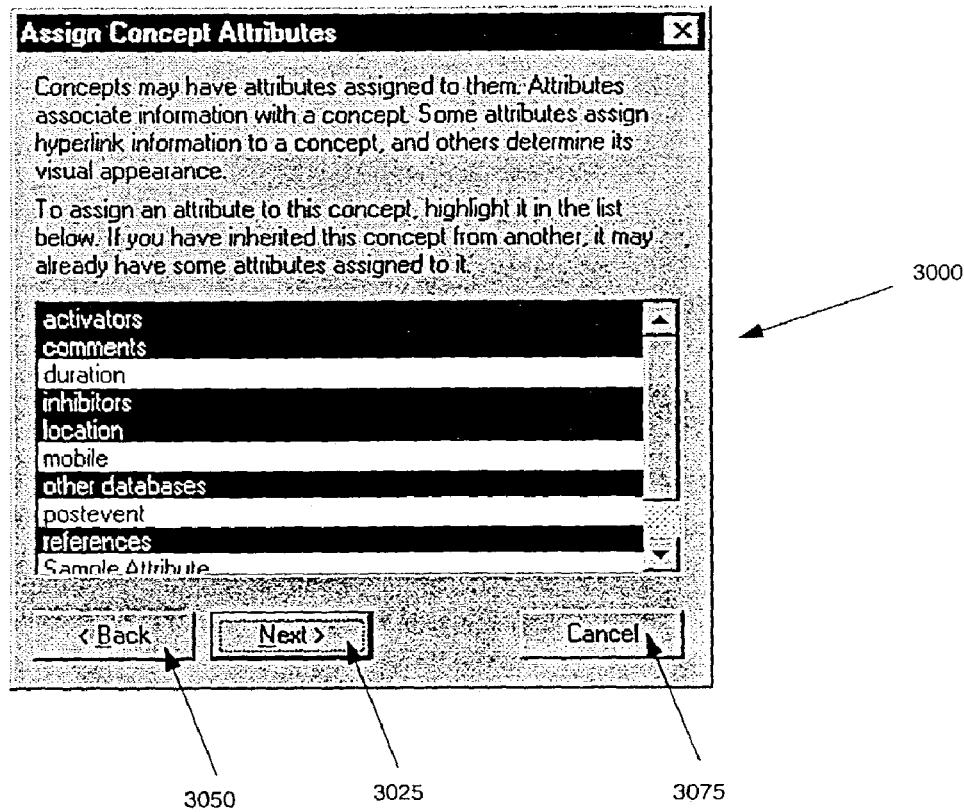

Upon selecting the Next button 385, the Assign Concept Attributes screen 3000 may be displayed, an example of which is shown in FIG. 5G. Attributes associated with the newly named concept can be selected from the Assign Concept Attributes screen 3000. If the newly named concept inherits concepts from a base concept, the inherited attributes may already be selected. Again, a User 20 may select the Next button 3025 to proceed to the next step of the Concept Forms series, the Back button 3050 to return to the previous screen, or the Cancel button 3075 to exit the Concept Forms series.

Figure 5H:
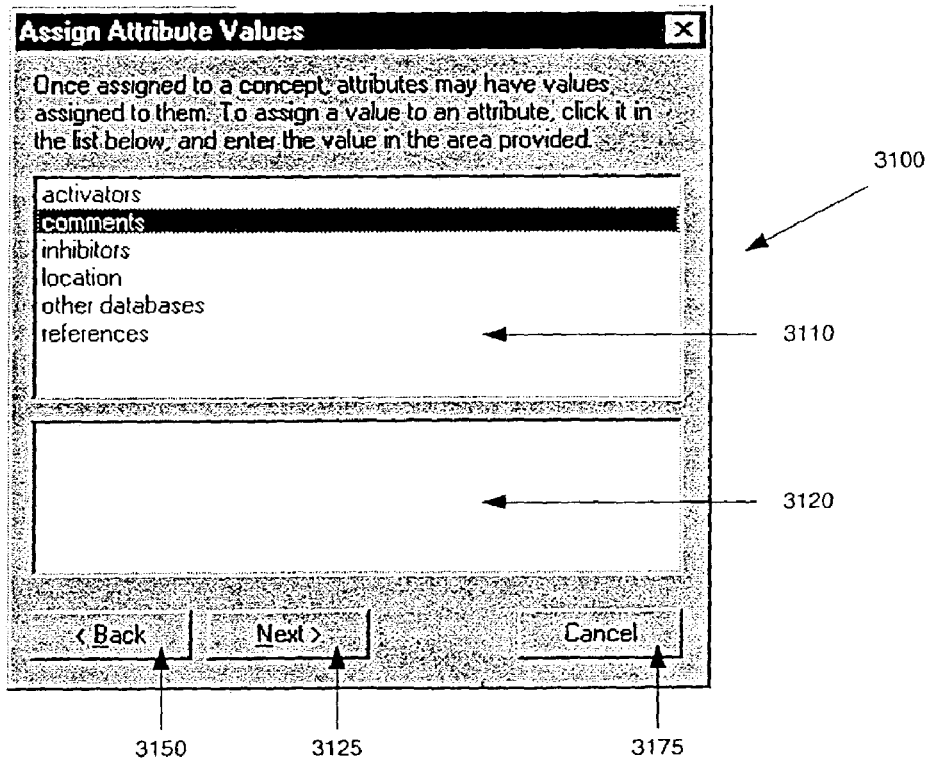

Upon selecting the Next button 3025, the Assign Attribute Values screen 3100 may be displayed, an example of which is shown in FIG. 5H. An attribute value may be defined by selecting an attribute from the Attribute Box 3110, and entering a desired value in the Value Box 3120. For example, selecting "comments" in the Attribute Box 3110 may allow textual comments to be entered in the Value Box 3120. If the attribute is an enumerated list, a list of allowed values for that attribute may be displayed in the Value Box 3120 for selection. A User 20 may select the Next button 3125 to proceed to the next step of the Concept Forms series, the Back button 3150 to return to the previous screen, or the Cancel button 3175 to exit the Concept Forms series.

Figure 5I:
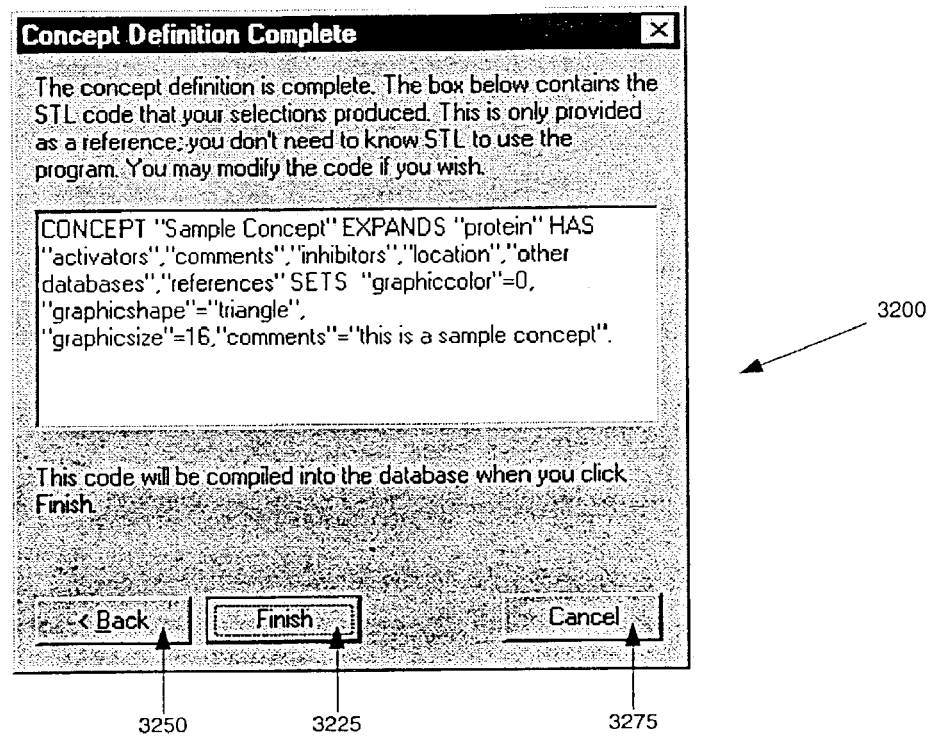

Upon selecting the Next button 3125, the Concept Definition Complete screen 3200 may be displayed, an example of which is shown in FIG. 5I. The Concept Definition Complete screen 3200 may show the STL code that may be produced from the User 20 selections. In the example shown in FIG. 5I, the following selections were made: "Sample Concept" was entered as the name (using the screen shown in FIG. 5A); "protein" was selected as the base concept (using the screen shown in FIG. 5B); "activators", "comments", "inhibitors", "location", "other databases" and "references" were selected as attributes (using the screen shown in FIG. 5G); values were assigned to "graphiccolor", "graphicshape", and "graphicsize" (using the screen shown in FIG. 5E); and the text string "this is a sample concept" was assigned to "comments" (using the screen shown in FIG. 5H). Once the concept definition is complete, the STL code may be compiled into the definitions database by selecting the Finish button 3225. Alternatively, the Back button 3250 may be selected to return to the previous screen, or the Cancel button 3275 can be selected to exit the Concept Forms series without compiling the concept definition into the definitions database.

Event Forms Series

Figure 6A:
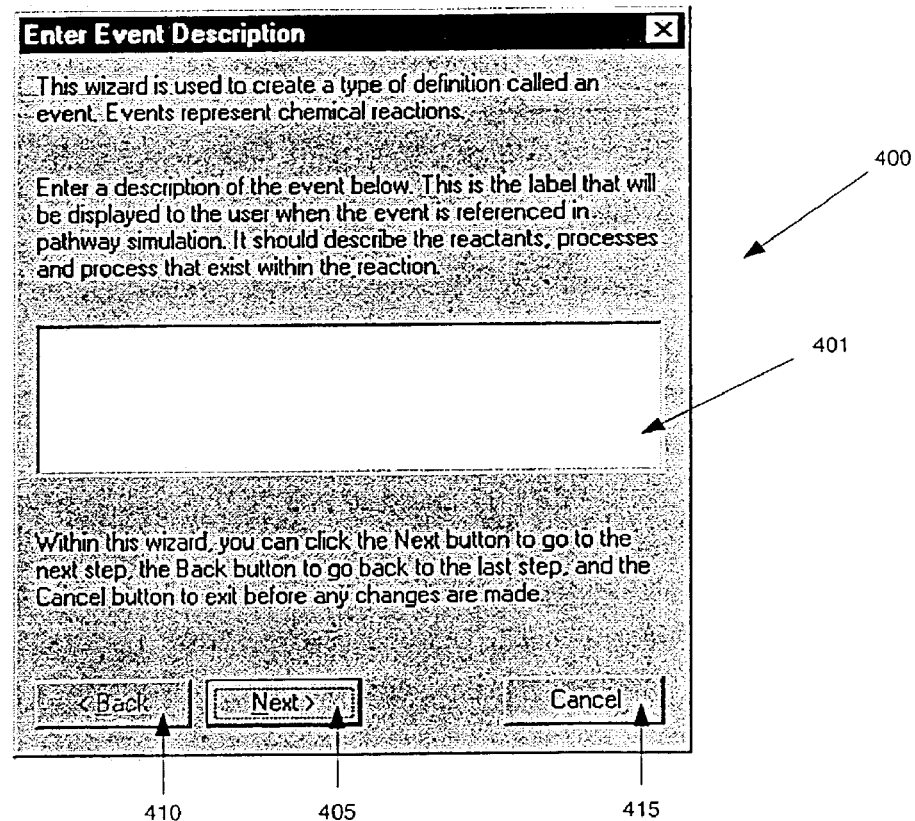

When a User 20 selects Define a Reaction 110c from the main menu 100 (FIG. 3), the Event Forms series may initiate to display an Enter Event Description screen 400, an example of which is shown in FIG. 6A. The Event Forms series may be used to define a new chemical reaction or relationship. As shown in FIG. 6A, a User 20 may have the option of entering an event description in field 401, and then selecting the Next button 405 to proceed to the next step of the Event Forms series. The event description is used for display only and is not parsed or translated by the Event Forms series. Alternatively, a User 20 may select the Cancel button 415 to exit the Event Forms series. It should be noted that user input in field 401 may determine the next step in the Event Forms series.

Figure 6B:
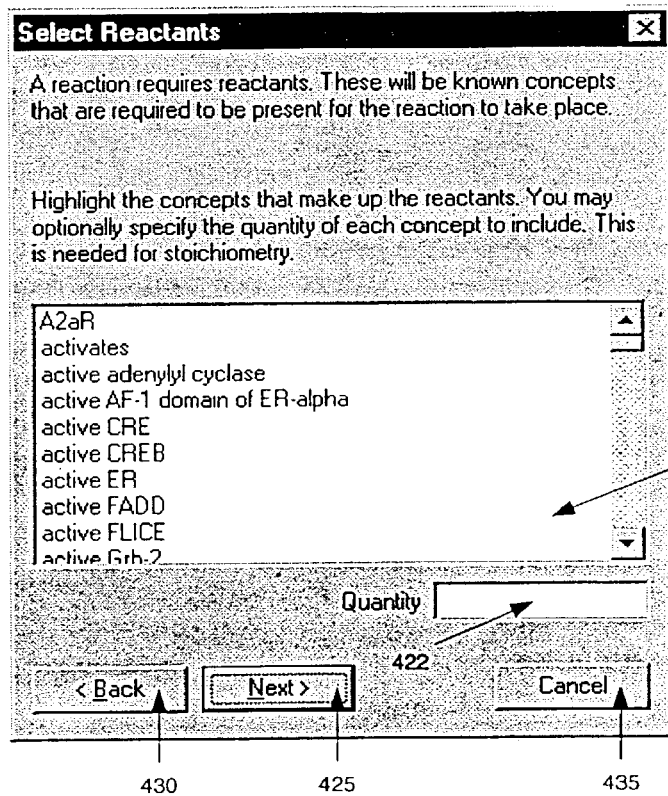

Upon selecting the Next button 405, the Select Reactants screen 420 may be displayed, an example of which is shown in FIG. 6B. One or more reactants for the event may be selected from the Selection Box 421. According to the present invention, reactants may be any concept required for a cellular reaction or biochemical pathway to proceed. In the case of a molecule binding to a receptor, for example, both the stimulus molecule and the receptor molecule are reactants and must be selected. If more than one of a given concept must be present for a reaction to proceed, that number may be entered in the Quantity Box 422 after the concept is selected from the Selection Box 421. A User 20 may select the Next button 425 to proceed to the next step of the Event Forms series, the Back button 430 to return to the previous screen, or the Cancel button 435 to exit the Event Forms series.

Figure 6C:
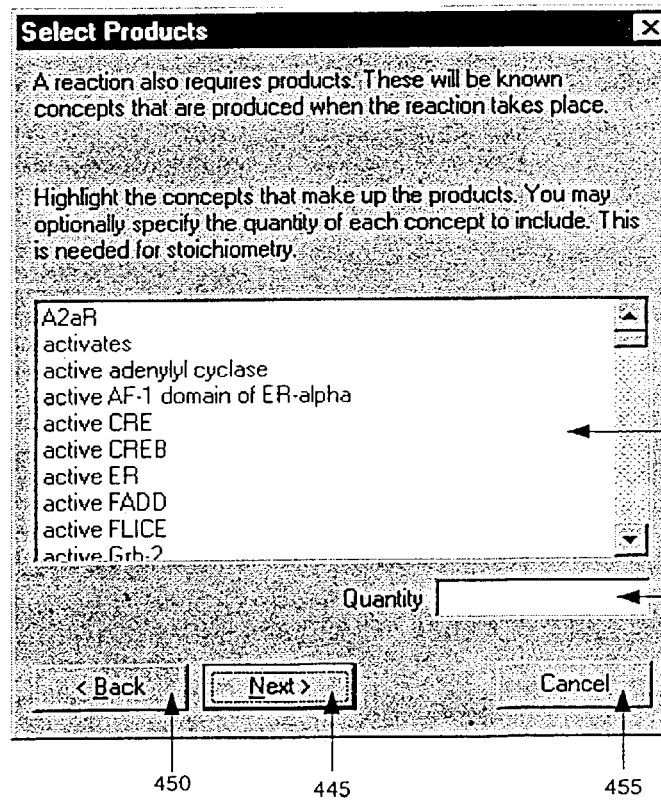

Upon selecting the required reactants in Selected Box 421, optionally entering a reactant quantity in Quantity Box 422, and selecting the Next button 425, the Select Products screen 440 may be displayed, an example of which is shown in FIG. 6C. One or more products from the reaction may be selected from the Selection Box 441. The products are concepts produced by the process of the reaction. According to the present invention, processes (e.g., apoptosis and gene transcription) may be products. For example, when the process of the reaction is a molecule binding to a receptor, the product might be a bound or activated receptor. If the reaction produces more than one instance of a concept, that number can be entered into the Quantity Box 442 after the product is selected. A User 20 may select the Next button 445 to proceed to the next step of the Event Forms series, the Back button 450 to return to the previous screen, or the Cancel button 455 to exit the Event Forms series.

Figure 6D:
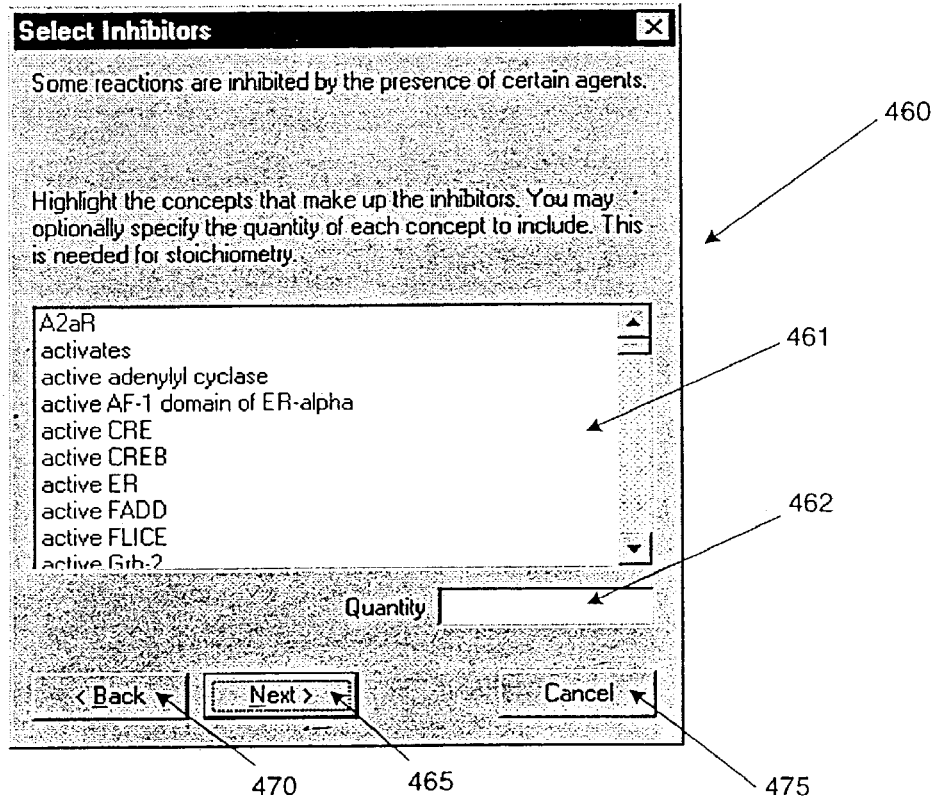

Selecting the Next button 445 may initiate the Select Inhibitors screen 460, an example of which is shown in FIG. 6D. One or more inhibitors for the reaction may optionally be selected from the Selection Box 461. Inhibitors may be concepts whose presence in the cellular environment means that the reaction cannot proceed. If the reaction is inhibited by more than one instance of a concept, the quantity of concepts may be entered into the Quantity Box 462 after the inhibitor is selected in the Selection Box 461. A User 20 may select the Next button 465 to proceed to the next step of the Event Forms series, the Back button 470 to return to the previous screen, or the Cancel button 475 to exit the Event Forms series.

Figure 6E:
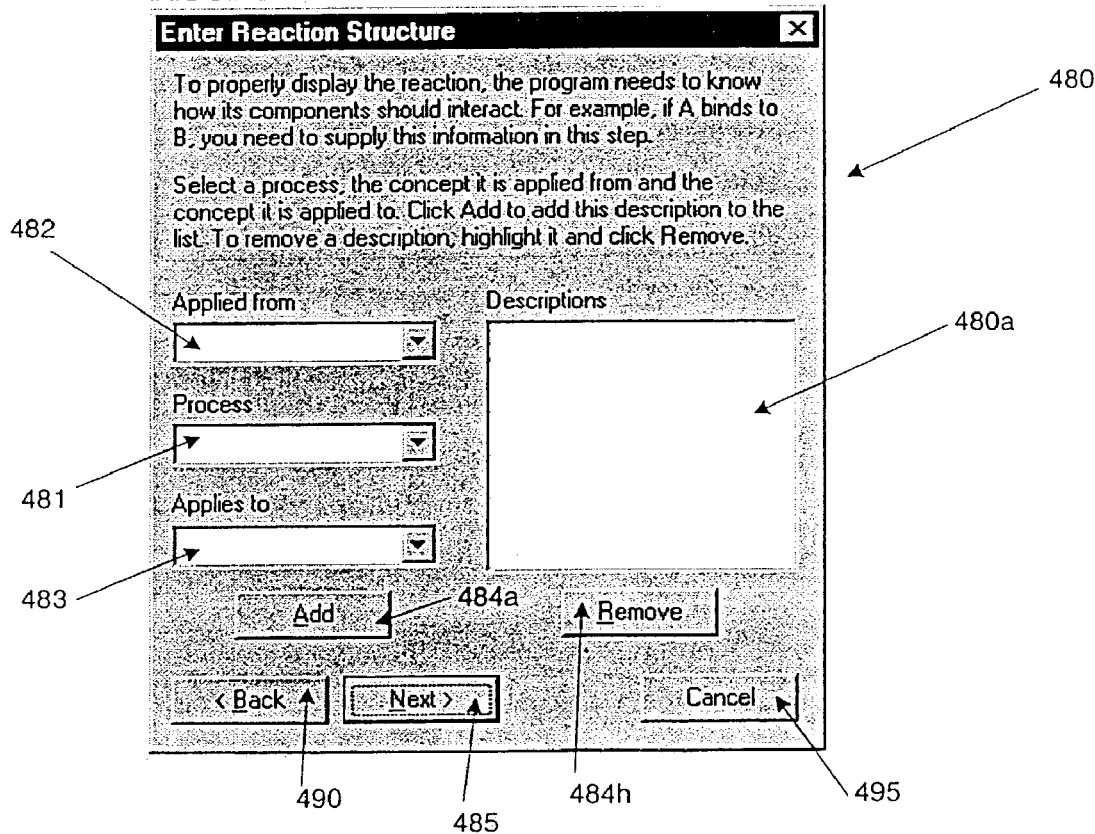

Upon selecting the Next button 465, the Enter Reaction Structure screen 480 may be displayed, an example of which is shown in FIG. 6E. The structure of the reaction, i.e., how the reaction components should interact, may optionally be defined from this screen. Reaction structure definitions are not required for the simulation of the reaction or cellular biochemical pathways in general, but instead may be utilized, for example, to define how the reactions will be textually and/or graphically displayed. To define a reaction structure, a process may be selected from the Process Box 481, the concept from which the process is applied may be selected from the Applied From Box 482, and the concept to which the process applies may be selected from the Applied To Box 483. For example, when the process of the reaction is a molecule "A" binding to a receptor "B", a User 20 may define the relationship "A binds to B" by selecting "A" in the Applied From Box 482, "binds to" in the Process Box 481, and "B" in the Applies To Box 483. The Add button 484*a* may then be selected to add the reaction structure to the Descriptions List Box 480*a*. Alternatively, a reaction structure definition may be removed from the Descriptions List Box 480*a* by selecting the definition from the Descriptions List Box 480*a* and clicking the Remove button 484*b*. A User 20 may select the Next button 485 to proceed to the next step of the Event Forms series, the Back button 490 to return to the previous screen, or the Cancel button 495 to exit the Event Forms series.

Figure 6F:
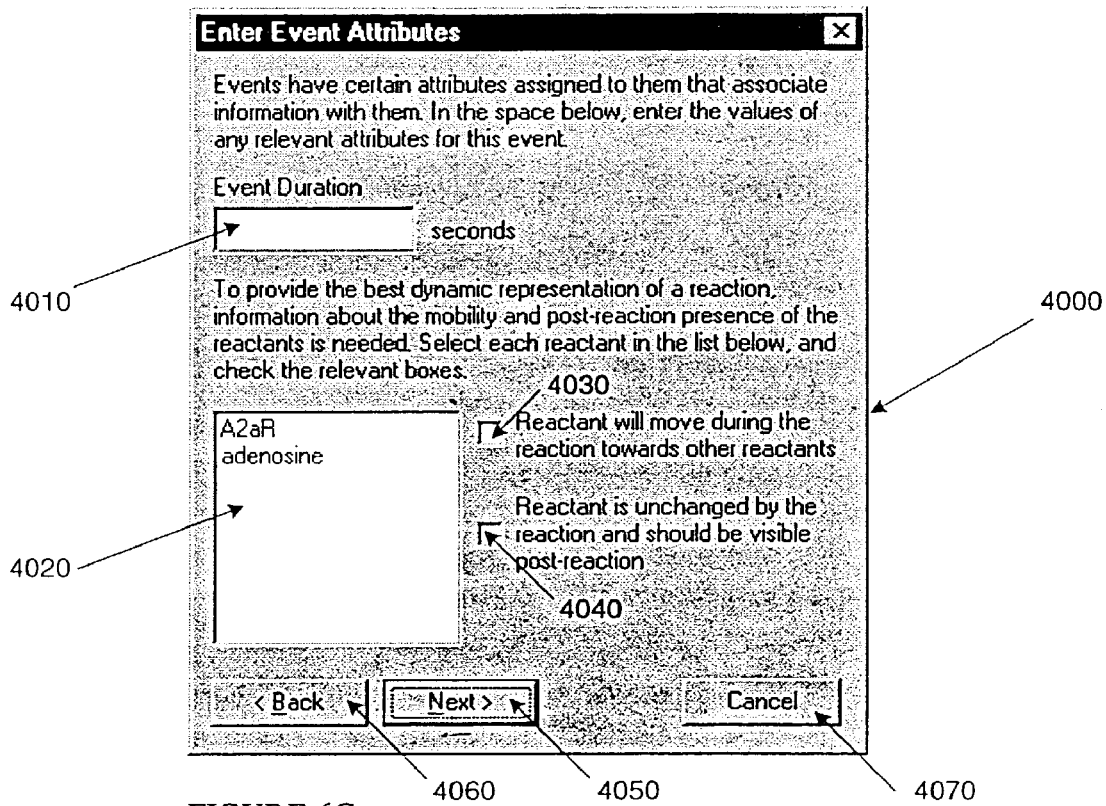

Upon selecting the Next button 485 from the Enter Reaction Structure screen 480 (FIG. 6E), the Enter Event Attributes screen 4000 may be displayed, an example of which is shown in FIG. 6F. Certain event attributes may optionally be assigned from this screen if relevant. For example, the event duration (i.e., the amount of time required for the event to proceed) may be entered in the Event Duration Box 4010. Reactant mobility characteristics and post-reaction presence may also be assigned by selecting the reactant from the Reactants List Box 4020 and checking Mobility Box 4030 and/or Post-Reaction Presence Box 4040. Preferably, checking the Mobility Box 4030 communicates that the corresponding reactant will move toward another reactant or reactants when the reaction is simulated. Likewise, checking the Post-Reaction Presence Box 4040 communicates that the corresponding reactant will be present after the reaction has occurred. A User 20 may select the Next button 4050 to proceed to the next step of the Event Forms series, the Back button 4060 to return to the previous screen, or the Cancel button 4070 to exit the Event Forms series.

Figure 6G:
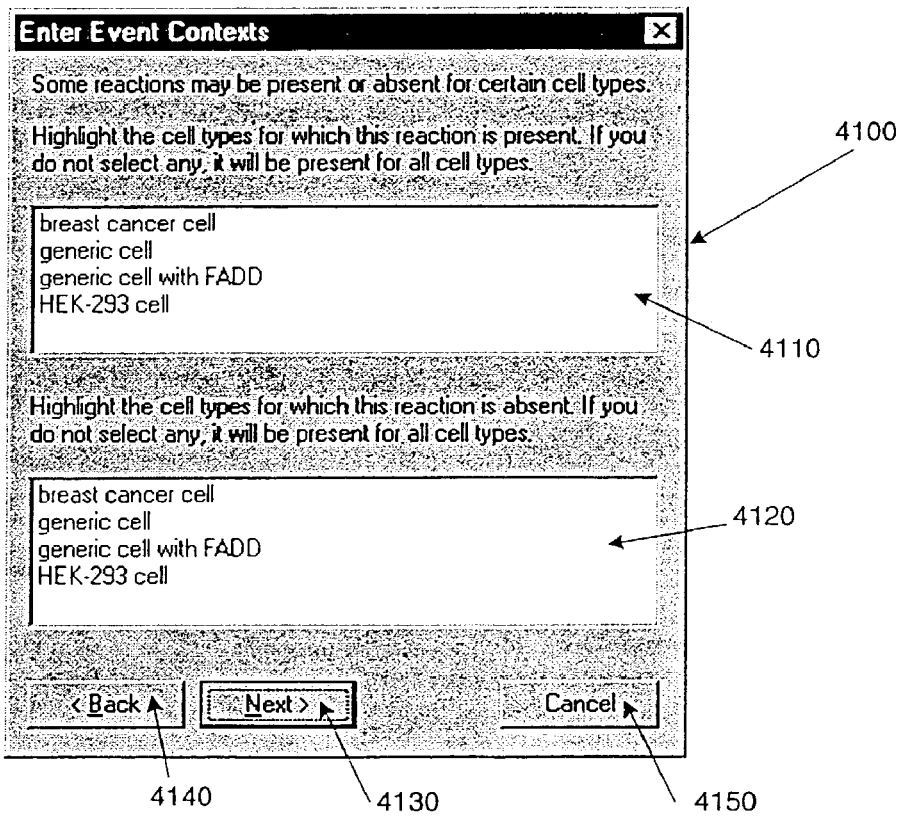

Selecting the Next button 4050 from the Enter Event Attributes screen 4000 (FIG. 6F) may initiate the Enter Event Contexts screen 4100, an example of which is shown in FIG. 6G. Cellular environments may be specified from the Enter Event Contexts screen 4100. Applicable cellular environments may comprise: (1) selecting, in Present Box 4110, cell types in which the reaction is present; or (2) selecting, in the Absent Box 4120, cell types in which the reaction is not present. If no cell types are selected in Present Box 4110 or Absent Box 4120, the reaction will be applied to all cellular environments. A User 20 may select the Next button 4130 to proceed to the next step of the Event Forms series, the Back button 4140 to return to the previous screen, or the Cancel button 4150 to exit the Event Forms series.

Figure 6H:
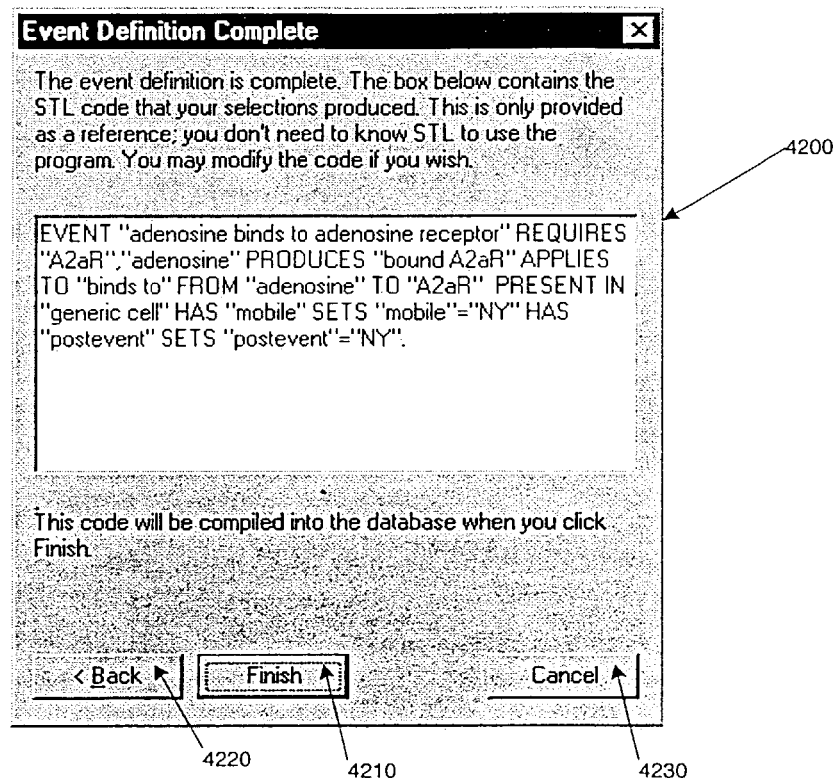

Upon selecting the Next button 4130, the Event Definition Complete screen 4200 may be displayed, an example of which is shown in FIG. 6H. Preferably, the Event Definition Complete screen 4200 shows the STL code that is produced from the user selections throughout the Event Forms series. Referring to FIG. 6H, for example, "adenosine binds to adenosine receptor" was entered as the description (using the screen shown in FIG. 6A), "adenosine" and "A2aR" were selected as reactants (using the screen shown in FIG. 6B), and "bound A2aR" was selected as the product (using the screen shown in FIG. 6C). A reaction description was entered with process "binds to" being applied from "adenosine" to "A2aR" (using the screen shown in FIG. 6E), "generic cell" was selected as the event context (using the screen shown in FIG. 6G) and the Mobility Box 4030 and Post-Reaction Presence Box 4040 were checked (using the screen shown in FIG. 6F). When a User 20 selects the Finish Button 4210, the STL code is preferably compiled into the definitions database. The Back button 4220 may be selected to return to the previous screen or the Cancel button 4230 may be selected to exit the Event Forms series without compiling the concept definition into the definitions database.

STL Editor/Compiler

Figure 7:
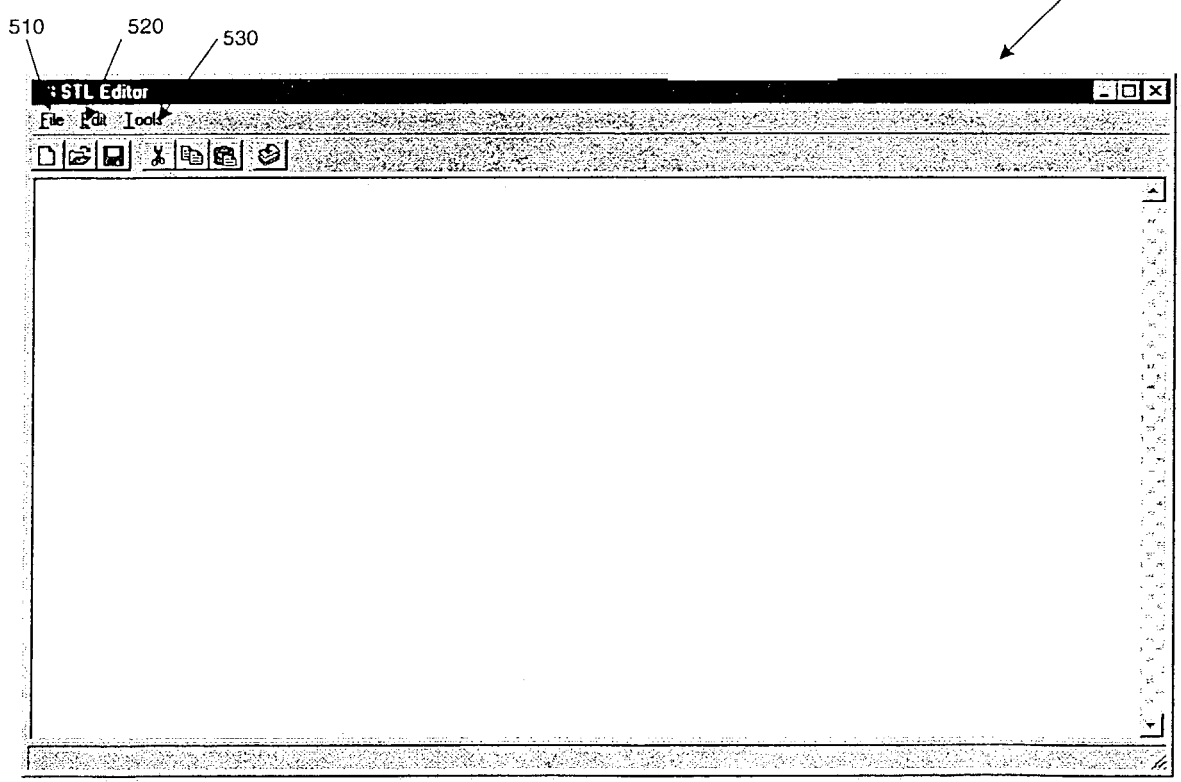

When Use STL Editor/Compiler 110*d* is selected from the main menu 100 (FIG. 3), the STL Editor/Compiler screen 500 may be displayed, an example of which is shown in FIG. 7. The STL Editor/Compiler screen 500 may be used to enter new definitions of attributes, concepts and events, to edit existing definitions, and compile changes to the definitions database. The STL Editor/Compiler may also be used to open a script file, enter new definitions or edit existing ones, compile the script to place the changes into the definitions database, and save the script changes. The script files represent an editable, user-readable representation of the definitions contained in the definitions database.

As shown in FIG. 7, in one embodiment of the invention, the menu options available from the STL Editor/Compiler may include File menu 510, Edit menu 520, and Tools menu 530. Action options within the File menu 510 may include New, Open, Save, Save As, and Exit using standard Windows dialogs or any other mechanism known in the art. Action options within the Edit menu 520 may include Cut, Copy, and Paste functions. Such Edit menu 520 options may be accomplished using any mechanism known in the art. Action options within the Tools menu 530 include Compile Script and Compile Incrementally functions.

The Compile Script function may compile the current script into the definitions database and replaces the previous entries in the definitions database. The Compile Incrementally function may compile the current script into the definitions database without replacing the previous entries in the definitions database. In a preferred embodiment, if script errors are detected, an error message may be displayed specifying the error that was found, and highlighting the area in the script where the error occurred. In this embodiment, a User 20 may rebuild the complete definitions database by executing the Compile Script function to destroy the old database and add in basic definitions. Alternatively, a User 20 may execute the Compile Incrementally function to add user-defined definitions. A more detailed description of STL is printed below.

Pathway Forms Series

Figure 8A:
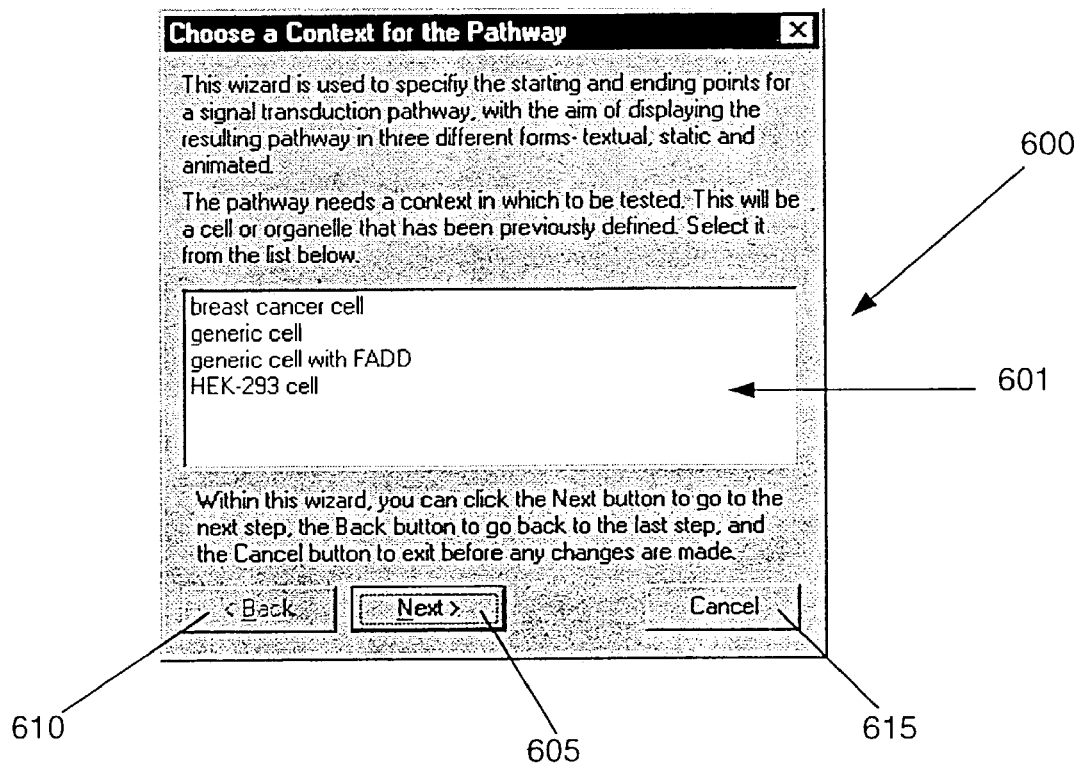

The Pathway Forms series may be used to specify the stimulus and context of a potential pathway. This process may start the Inference Engine 14 and generate all possible pathways, applying all known reactions, until no new intermediate products are produced. The program may then display three views of the pathway: textual, static and dynamic. When a User 20 initiates the Pathway Forms series from the main menu 100 by selecting the Generate pathway button 110*e* (FIG. 3), a Choose a Context for the Pathway screen 600 may be displayed, an example of which is shown in FIG. 8A. As shown in FIG. 8A, the Next button 605 will take you to the next step of the Pathway Forms series, the Back button 610 will take you to the previous step, and the Cancel button 615 will exit the Pathway Forms series.

Figure 8B:
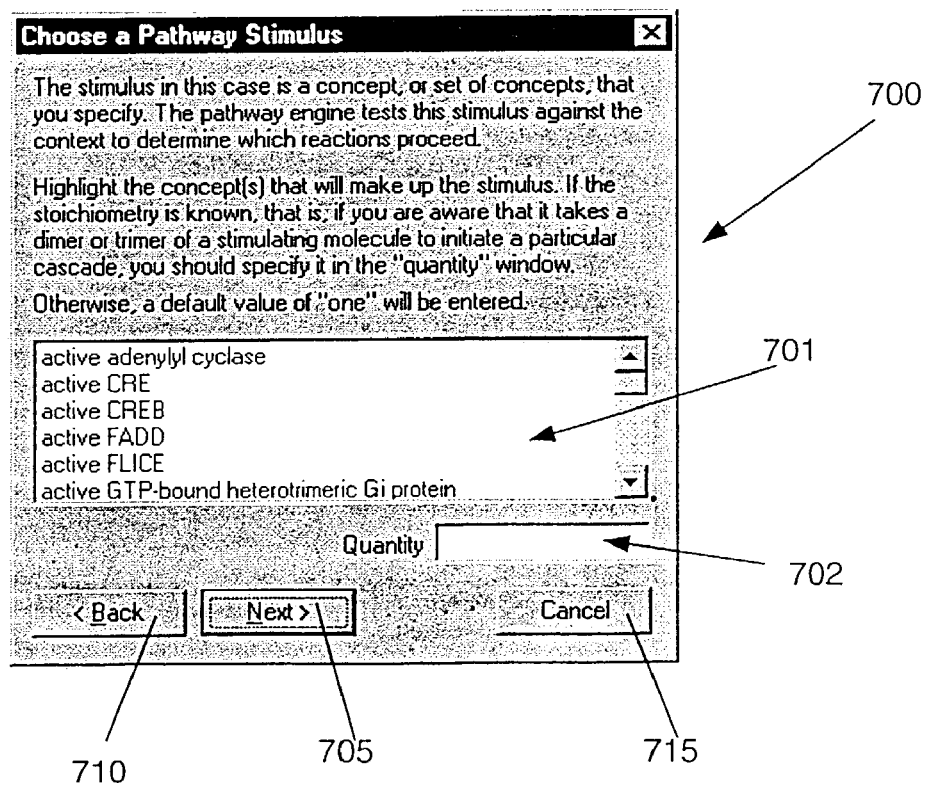

As shown in FIG. 8A, the User 20 may select a cellular context for a pathway. This may be a type of cell. Selecting a Next button 605 may bring the User 20 to a Choose a Pathway Stimulus screen 700, an example of which is shown in FIG. 8B. The Choose a Pathway Stimulus screen 700 may allow the User 20 to choose one or more stimulus concepts. Stimulus concepts may be concepts that may be introduced to the cellular context selected in the Choose a Context for the Pathway screen 600 shown in FIG. 8A. The User 20 may select concepts from the List Box 701 to serve as stimuli. If more than one instance of a concept is required to generate a desired result, that number may be entered in the Quantity Box 702.

Figure 8C:
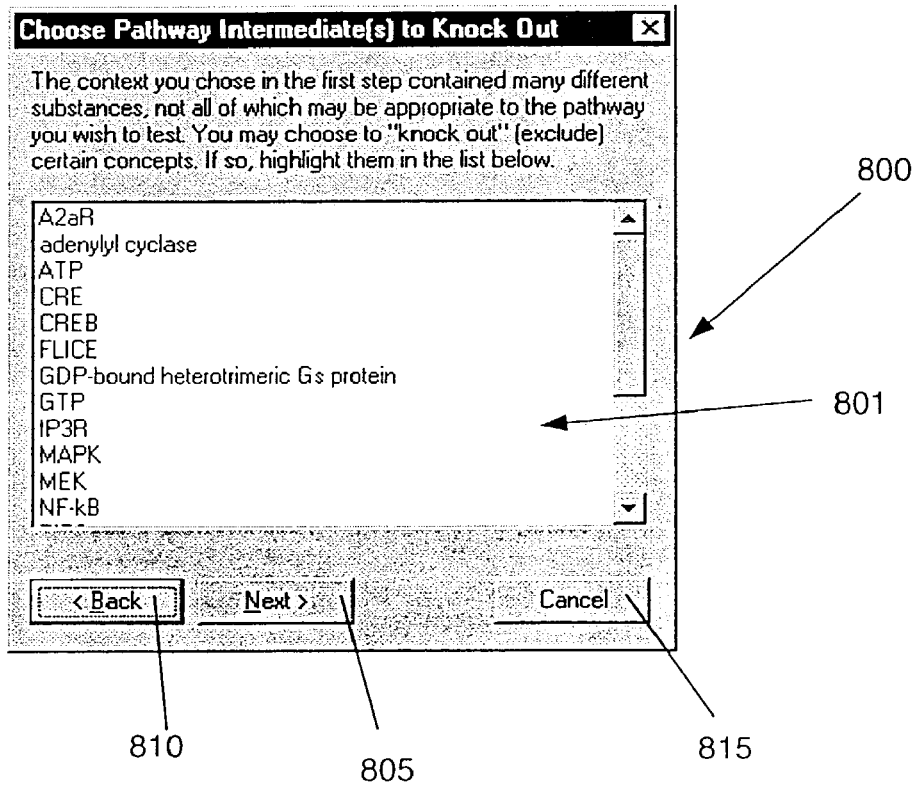

Clicking the Next button 705 may bring the User 20 to the Choose Pathway Intermediate(s) to Knock Out screen 800, an example of which is shown in FIG. 8C. If a User 20 wishes to test how a pathway is influenced by the absence of certain concepts, these concepts may be selected from in the List Box 801. The selected concepts will be removed from the cellular context. Preferably, however, the selected concepts are only removed from the immediate corresponding pathway generation. Preferably, the selected concepts are not permanently removed from the pathway generation.

Figure 8D:
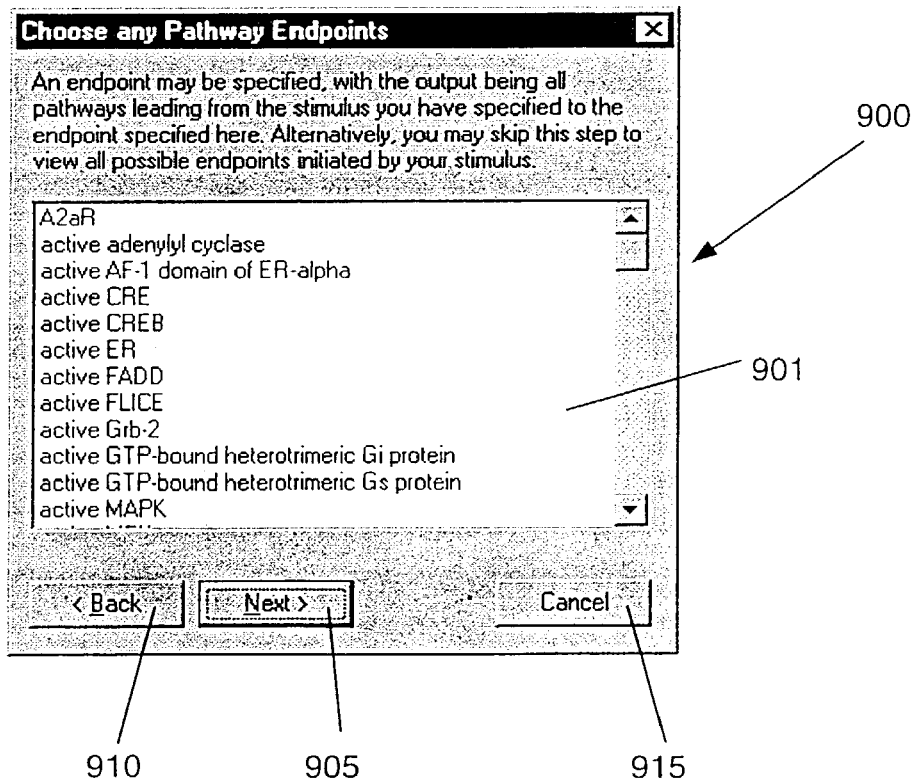

Clicking the Next button 805 brings the User 20 to the Choose any Pathway Endpoints screen 900, an example of which is shown in FIG. 8D. If the User 20 wishes the pathway to stop when a certain concept has been generated, such pathway endpoints may be selected in Selection Box 901. This is useful in determining if a pathway intermediate is produced in complex pathways.

Figure 8E:
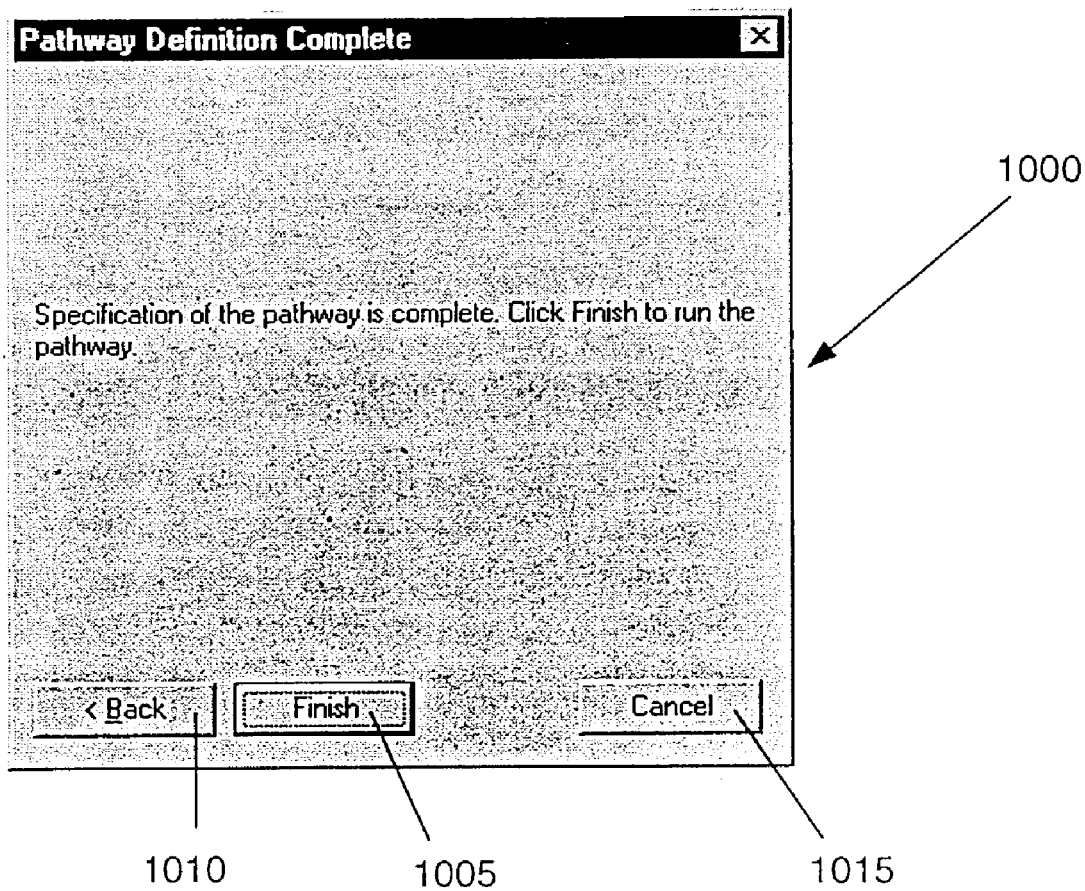

Clicking the Next button 905 brings the User 20 to the Pathway Definition Complete screen 1000, an example of which is shown in FIG. 8E. The User 20 may click the Finish button 1005 to initiate the display module, which will be explained in more detail below.

Display Module

Figure 9:
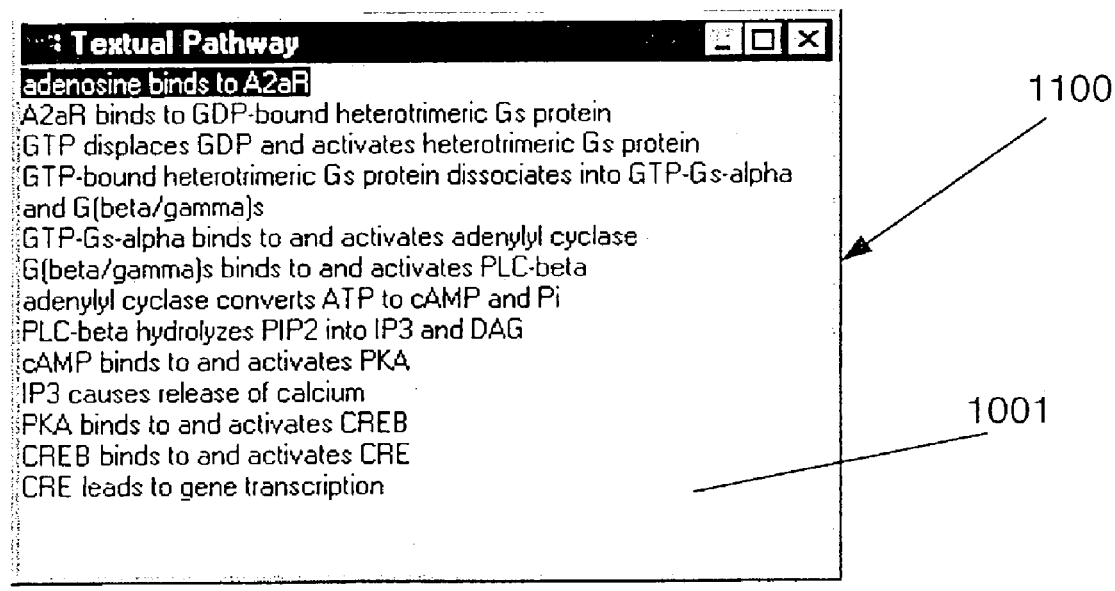

A pathway may be displayed in a textual form, as shown in FIG. 9. FIG. 9 illustrates an example of a Textual Pathway window 1100, which shows each reaction/event in the order that it was triggered. If there are more events than will fit on the Textual Pathway window 1100, a scroll bar may appear to the right to scroll the output. The event(s) that is currently being displayed in the dynamic pathway may be highlighted. The Textual Pathway window 1100 may be sized independently, and may be closed without affecting program operation. In a further embodiment, the Textual Pathway window 1100 may be ordered by pathway with a line between each pathway. In this embodiment, the User 20 has an option to order the events based upon paths or to order the events based upon a time stamp assigned to the path. Preferably, the displayed pathway may be highlighted as it occurs.

Figure 10A:
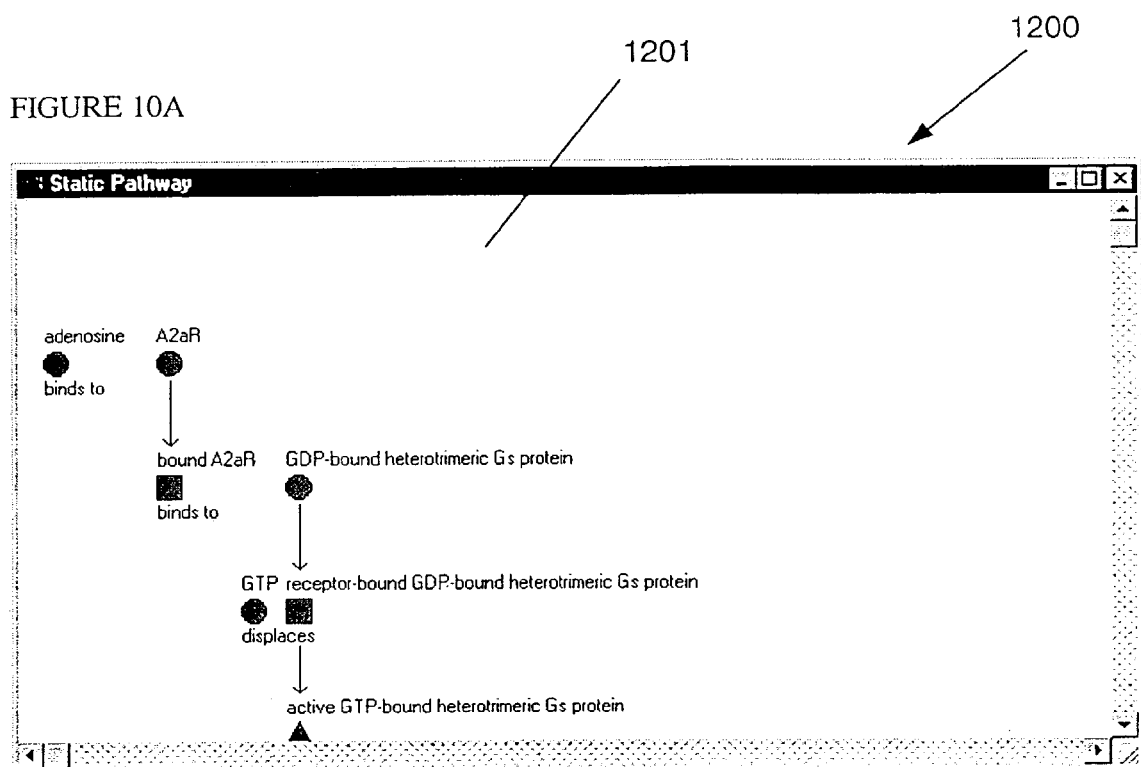

The pathway may also be displayed in a static, graphical form, as shown in FIG. 10A. FIG. 10A illustrates an example of a Static Pathway window 1200, which shows a schematic diagram of the concepts involved and the reactions that occur. If the diagram extends beyond the confines of the Static Pathway window 1200, scroll bars may appear on the bottom and right. The Static Pathway window 1200 may be sized independently, and may be closed without affecting program operation.

In one embodiment of the present invention, a pop-up menu of attributes may appear when the user clicks on a left mouse button on a concept. From the menu of attributes the User 20 may choose from attributes such as "references" or "comments". Choosing an attribute may activate a read-only version of the concept editor. The event editor may also be activated by clicking on the event arrow corresponding to an event.

Figure 10B:
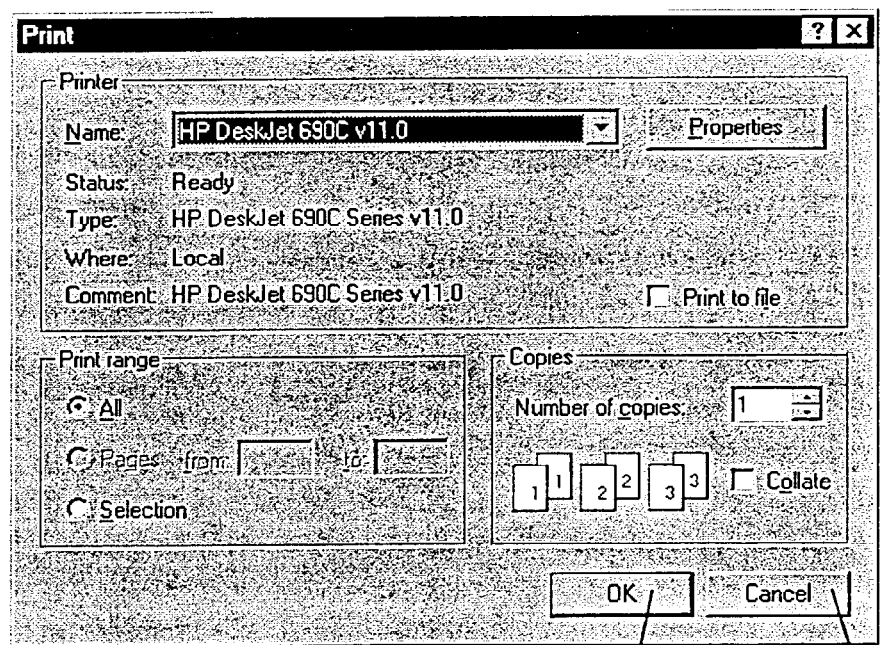

In one embodiment of the present invention, if the User 20 clicks a left mouse button outside of a concept, a pop-up menu may appear allowing the User 20 to "Cancel" the menu or "Print" the diagram. If the User 20 chooses to print, a Print window 1300 may appear, an example of which is shown in FIG. 10B. The User 20 may make any changes desired, then click the OK button 1305 to print the diagram.

Figure 11:
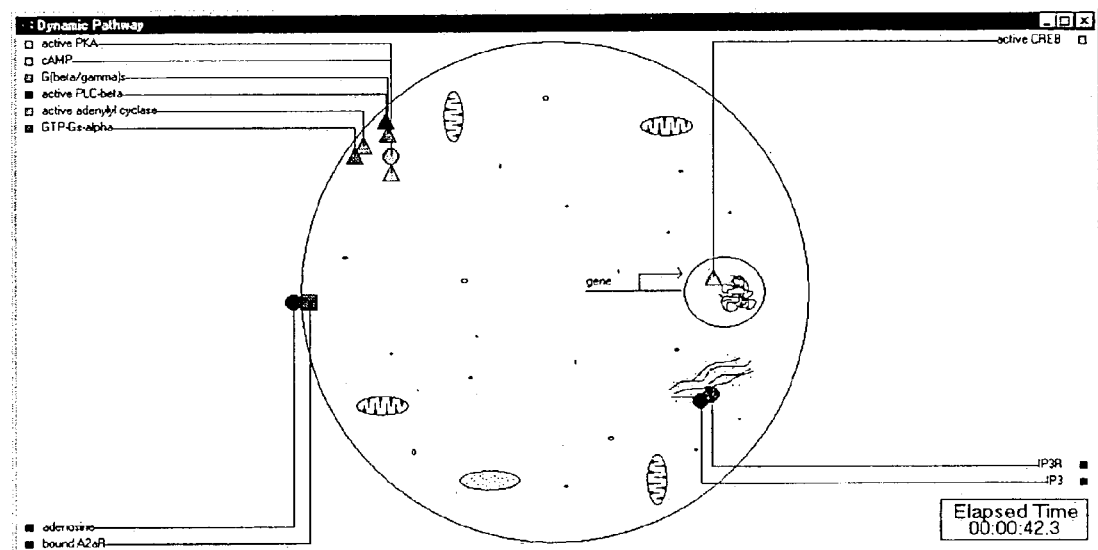

The pathway may also be displayed as a dynamic animation, an example of which is shown in FIG. 11. FIG. 11 illustrates a Dynamic Pathway window 1400, which shows an animation of the pathway against the backdrop of a "standard" cell. A shape represents each concept. The names of each concept are preferably displayed on the sides, with lines preferably drawn from the names to the concept shapes. The current elapsed time of the pathway may be displayed on the bottom right. The Dynamic Pathway window 1400 may be sized independently, and may be closed without affecting program operation.

If the pathway proceeds towards proliferation, apoptosis, differentiation, or other pre-determined events, the display may display the event name on the static display. Gene transcriptions may be represented by a standard symbol to the left of the nucleus, displaying the name of the gene or "gene" id, if it is not known.

As each event is reached in the animation, it may be highlighted in the Textual Pathway window 1100 (FIG. 9).

Figure 12:
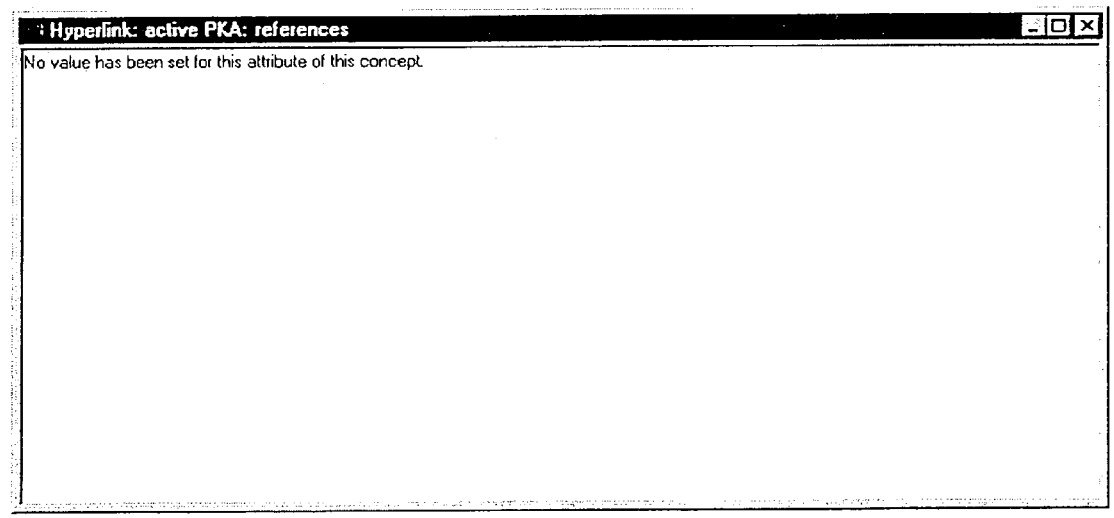

In one embodiment of the present invention, if the User 20 clicks the left mouse button on a concept, a pop-up menu of attributes may appear (such as "references", "comments") that the User 20 can choose from. Choosing an attribute may brings up a hyperlink window (FIG. 12). Choosing an attribute may also activate a read-only version of the concept editor. The event editor may also be activated by clicking on the event arrow corresponding to an event.

In one embodiment of the present invention, if the User 20 clicks the left mouse button outside of a concept, a pop-up menu may appear that allows the User 20 to "Cancel" the menu, "Run" the animation, "Stop" the animation, "Restart" the animation from the beginning, or change the "Speed" of the animation. The animation may be stopped and started using "Run" and "Stop", and choosing "Speed" preferably brings up another menu of speeds from 1 (slowest) to 10 (fastest). The User 20 may also choose the views desired from a pathway generator menu. For example, the User 20 may choose to display only the static and textual displays and those displays may be maximized upon activation of the system of the present invention.

Choosing an attribute may activate a read-only version of the concept editor. The event editor may also be activated by clicking on the event arrow corresponding to an event. Any text marked as a hyperlink (e.g., blue and underlined) will preferably bring up a Web browser to display information from the Internet when chosen by the user.

Figure 13:
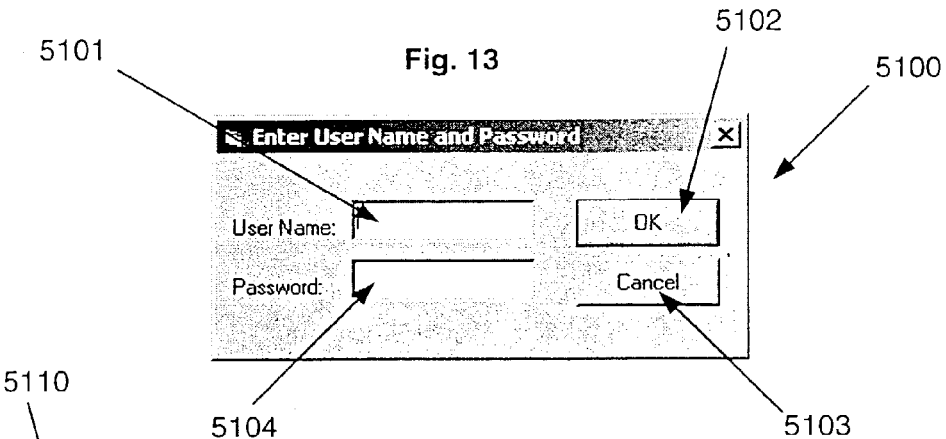

As illustrated in FIG. 13, Enter User Name and Password window 5100 is an example of a user login screen which may be used in the present invention. In this embodiment, a User 20 may be required to enter a user login ID and password. The user login ID and password may be maintained by a client. A User 20 may press the OK button 5102 to communicate the entered user login ID and password to the client. The user login ID and password may be authenticated against security information stored in a database of the client.

Figure 14:
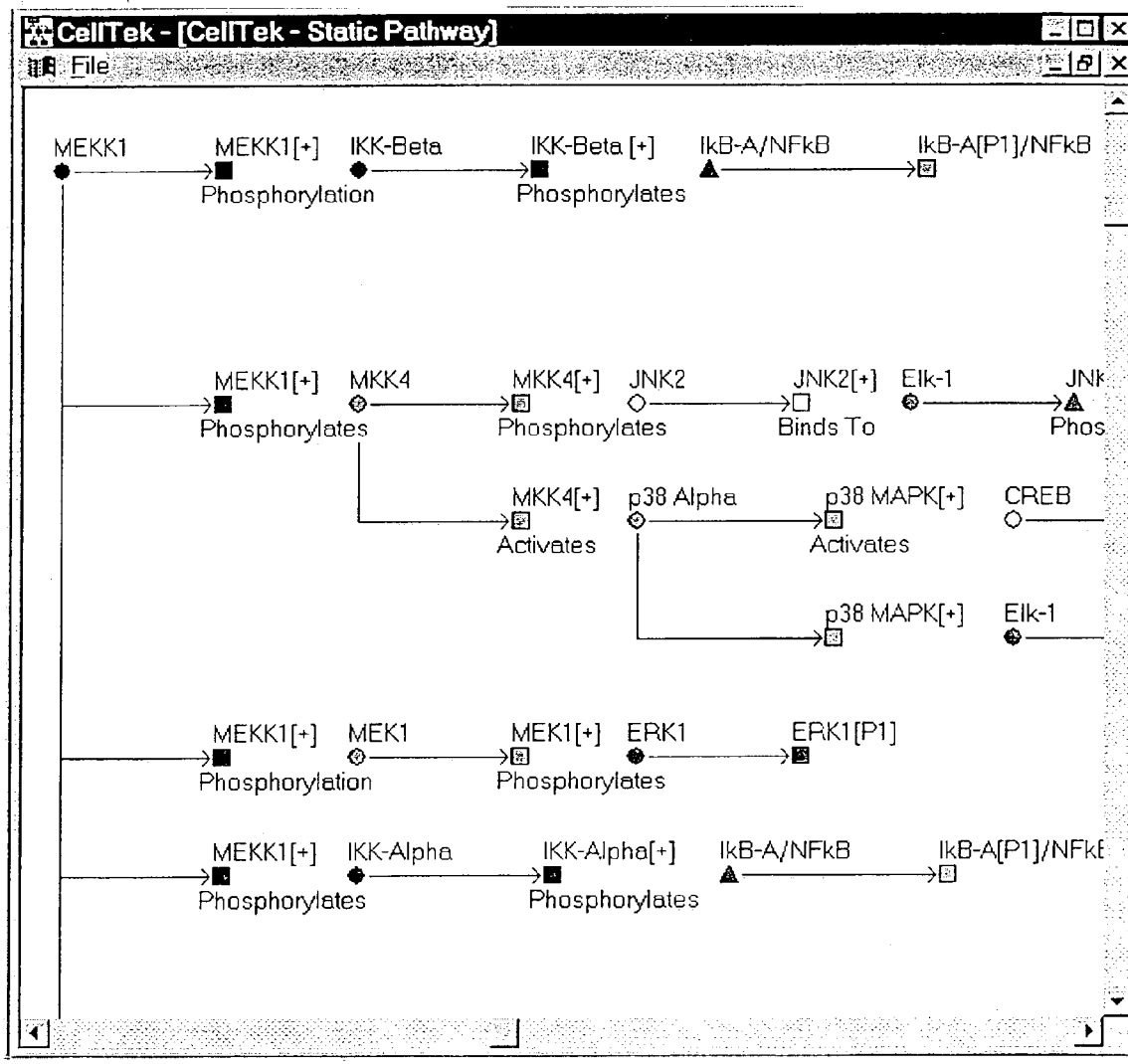

In an embodiment of the present invention, a preferred static display of pathways is as shown in window 5110 in FIG. 14. Window 5110 may show feedback loops. Feedback loops may be points in pathways in which the pathway regulates itself by feeding back to an original point in the pathway. A User 20 may print the display to a file or directly to a printer. A User 20 may select concepts or events and view all of the data associated with the selected concept or event.

Figure 15:
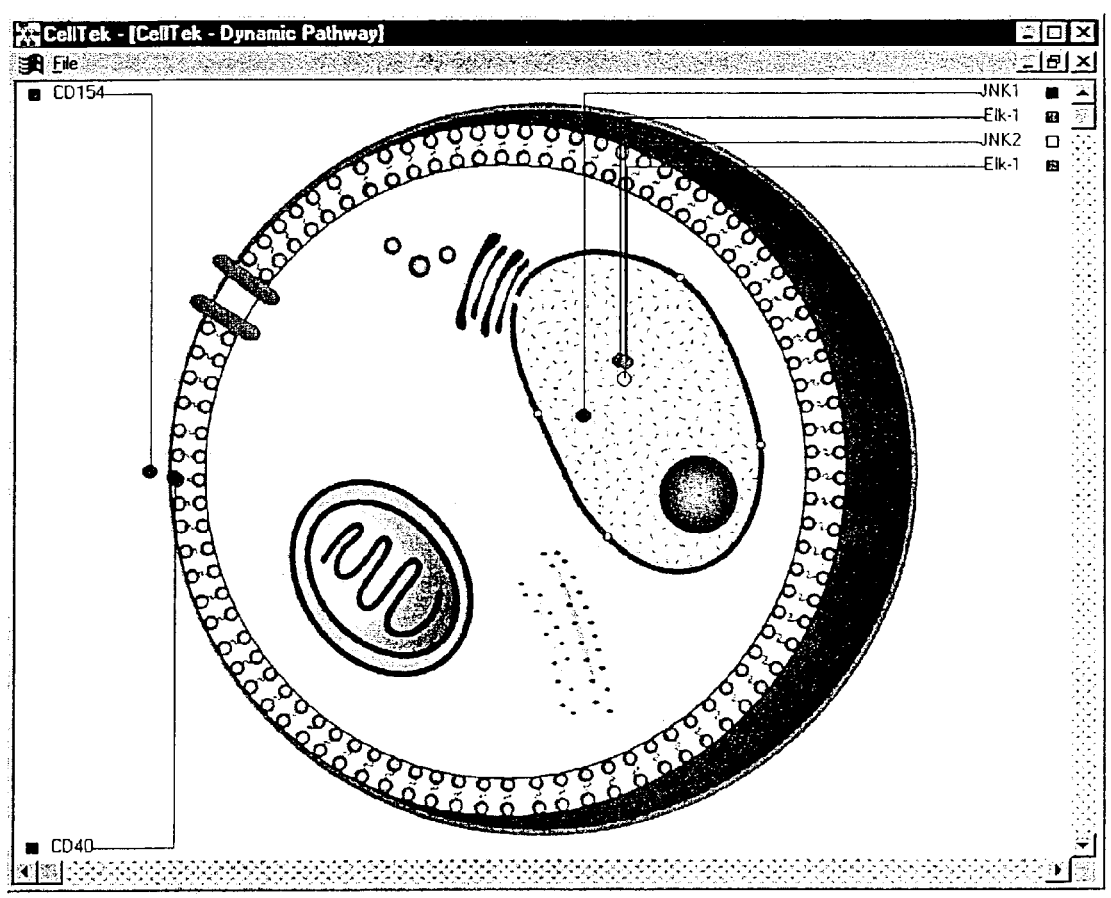

In an embodiment of the present invention, a preferred dynamic display of pathways is as shown in window 5120 in FIG. 15.

In an embodiment of the present invention, a preferred textual display is as shown in window 5140 and window 5130 in FIG. 16 and FIG. 17, respectively. As shown in windows 5130 and 5140, the textual display may display the user entered initial conditions including user name, pathway type, context, stimulus, exclusions and endpoints. The textual display may be outputted to a file and/or printed. The textual display may be organized in several different ways. For example, window 5130 shows the textual display ordered by the pathway that occurs in the static display. In contrast, window 5140 shows the textual display ordered as they occur in time steps.

Figure 18:
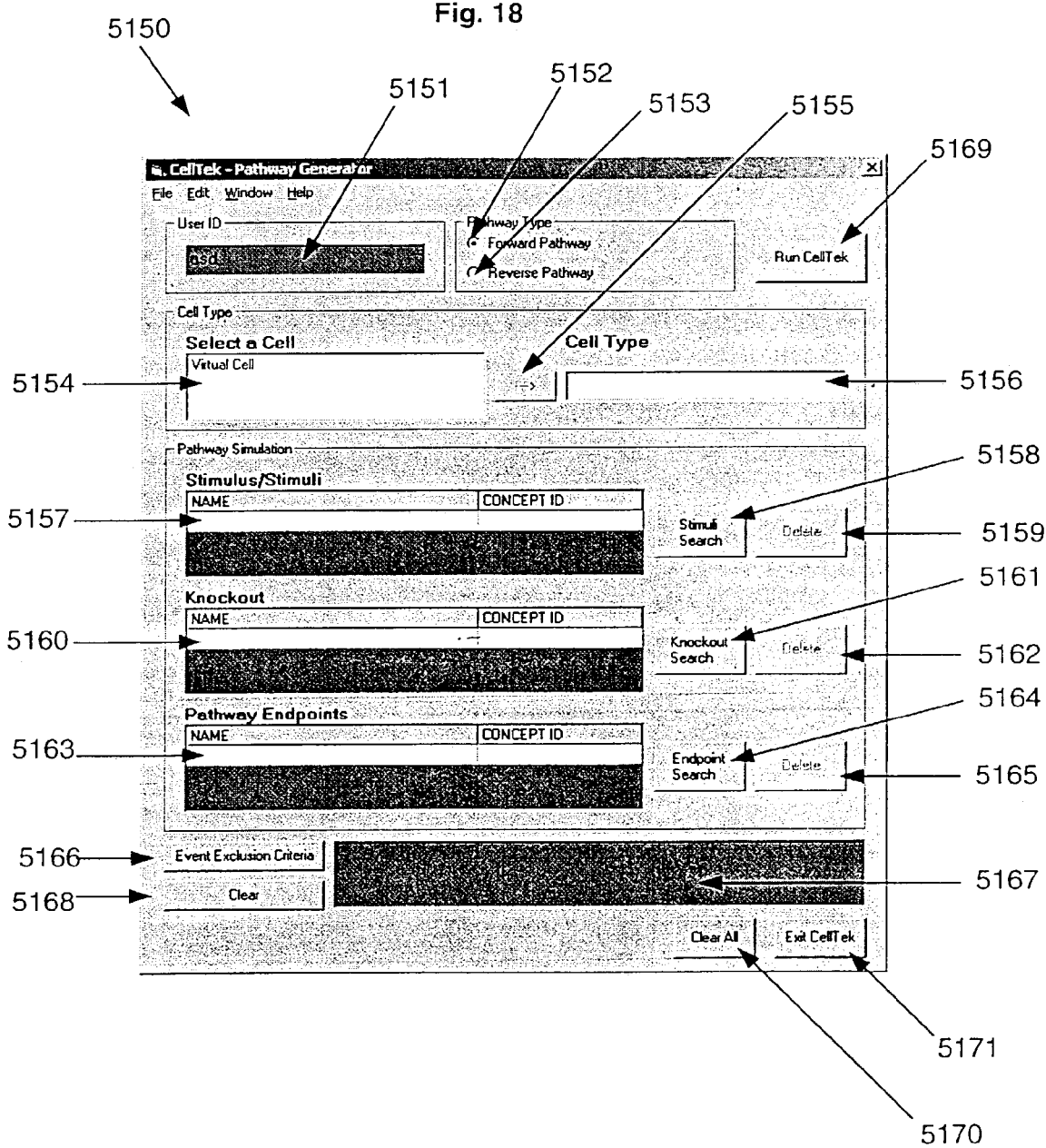

FIG. 18 illustrates a Pathway Generator window 5150 of the present invention. The Pathway Generator window 5150 may be the main window after the Enter User Name and Password window 5100. The user login ID entered in the Enter User Name and Password window 5100 may be displayed may be displayed in box 5151 of the Pathway Generator window 5150. In the Pathway Generator window 5150, a User 20 may choose from at least two pathway types. For example, a User 20 may select Forward Pathway radio button 5152 to execute a forward pathway. Alternatively, a User 20 may select Reverse Pathway radio button 5153 to execute a reverse pathway. A User 20 may select a cell from the Cell Type list box 5154 by highlighting a cell and selecting the Enable button 5155. This may load the cell into the Cell Type window 5156. In an embodiment of the present invention, a cell must be chosen and only one cell may be chosen.

A User 20 may choose a stimulus or stimuli when running the forward pathway generation and may choose a stimulus/stimuli when running the reverse pathway generation. A User 20 may choose a stimulus or stimuli by selecting the Stimuli Search button 5158. Upon selecting the Stimuli Search button 5158, a User 20 may be presented with the Search for Stimulus window 5180 shown in FIG. 19. If a User 20 selects a stimulus/stimuli, the corresponding information may be displayed in the Stimulus window 5157. A User 20 may choose-to delete a given stimulus by selecting a stimulus in the Stimulus window 5157 and subsequently selecting the Delete button 5159.

A User 20 may choose a concept knockout when running the forward pathway generation or reverse pathway generation. A User 20 may choose to search all available concept knockouts by selecting the Knockout Search button 5161. Upon selecting the Knockout Search button 5161, a User 20 may be presented with the Search for Concepts window 5190 shown in FIG. 20. If a User 20 selects a knockout concept, the corresponding information may be displayed in the Concept knockout window 5160. A User 20 may choose to delete a given concept knockout by selecting a concept knockout in the Concept Knockout window 5160 and subsequently selecting the Delete button 5162.

A User 20 may choose a pathway endpoint when running the forward pathway generation or reverse pathway generation. A User 20 may choose to search all available pathway endpoints by selecting the Endpoint Search button 5164. Upon selecting the Knockout Search button 5164, a User 20 may be presented with the Search for Pathway Endpoints window 5200 shown in FIG. 21. If a User 20 selects a pathway endpoint, the corresponding information may be displayed in the Pathway Endpoints window 5163. A User 20 may choose to delete a given pathway endpoint by selecting a pathway endpoint in the Pathway Endpoints window 5163 and subsequently selecting the Delete button 5165.

Figure 22:
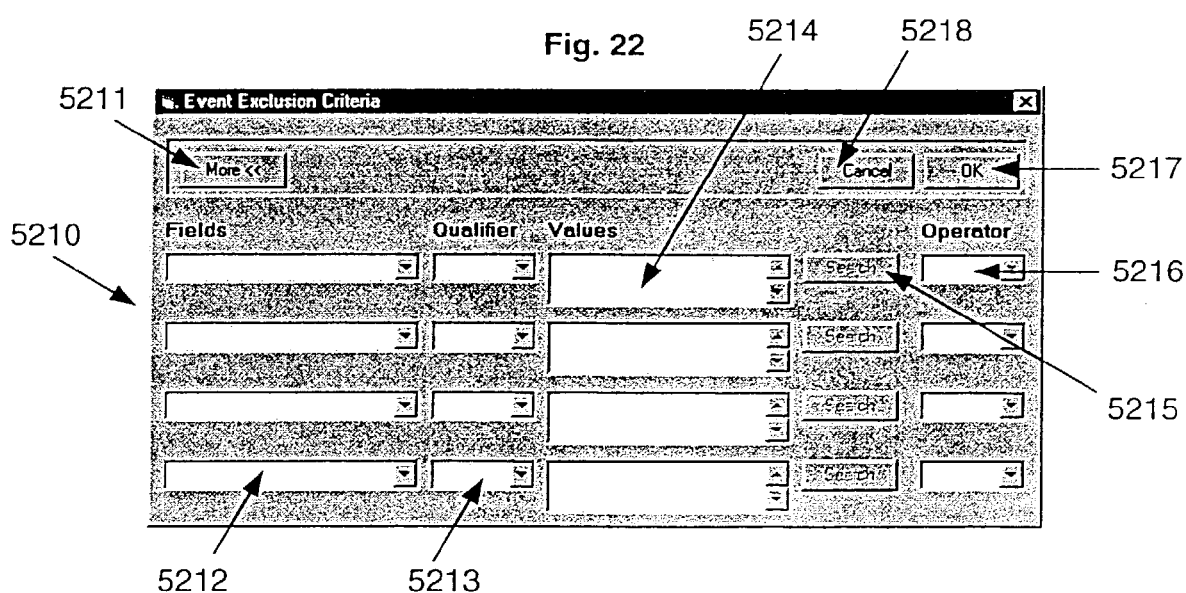

A User 20 may choose to exclude certain information from the pathway generation by selecting the Event Exclusion Criteria button 5166. If a User 20 selects the Event Exclusion Criteria button 5166, an Event Exclusion Criteria window 5210 may be presented as shown in FIG. 22. Any criteria entered by a User 20 in the Event Exclusion Criteria window 5210 may be displayed in the Event Exclusion Criteria box 5167. A User 20 may clear the Event Exclusion Criteria box 5167 by selecting the Clear button 5168. A User 20 may execute the pathway based on the selected information by selecting the Run CellTek button 5169. A User 20 may clear all information in the Pathway Generator window 5150 by selecting the Clear All button 5170. A User 20 may exit the Pathway Generator window 5150 by selecting the Exit CellTek button 5171. In a preferred embodiment, a User 20 may save the pathway conditions from a given pathway to a file. A User 20 may also open information previously saved in the Pathway Generator window 5150.

Figure 19:
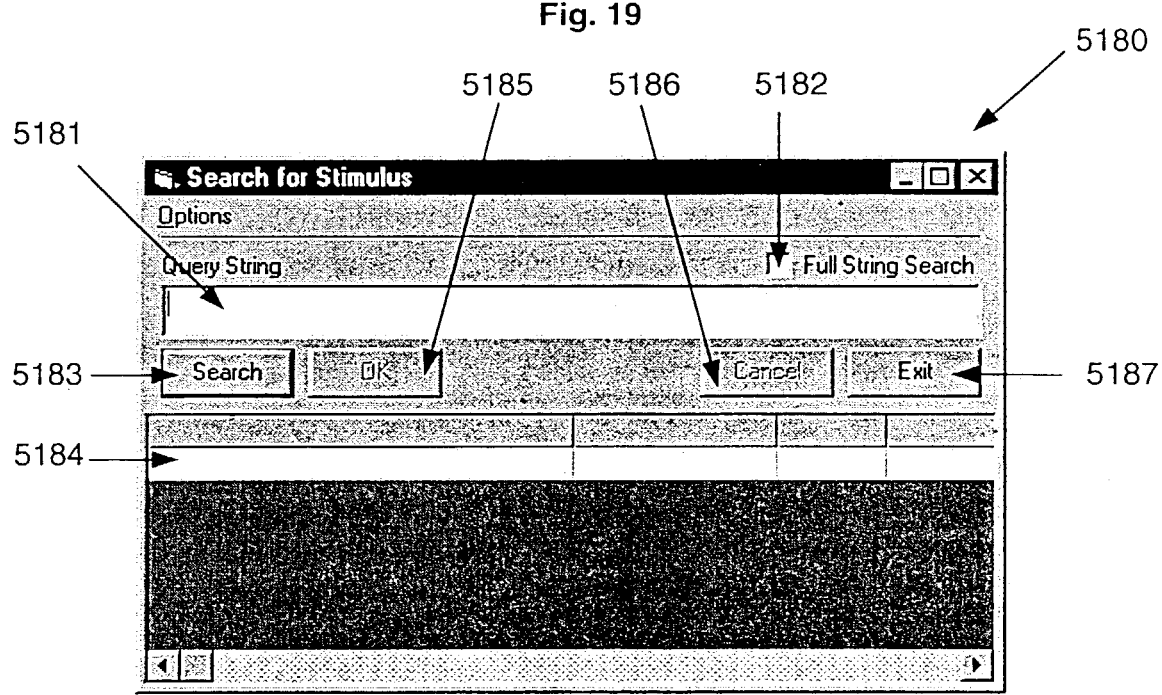

As shown in FIG. 19, a User 20 may enter a full text search for information by entering the full text into the Query String field 5181, selecting the Full String Search check box 5182, and subsequently selecting the Search button 5183. A User 20 may also enter partial string searches by deselecting the Full String Search check box 5182, entering the partial search information into the Query String field 5181, and subsequently selecting the Search button 5183. Upon selection of the Search button 5183, the results of the search are displayed in the Result box 5184. A User 20 may choose to use the searched information by selecting the given information in the Result box 5184 and subsequently selecting the OK button 5185. The selected information will then be moved to a corresponding location in the Pathway Generator window 5150. A User 20 may also select the Cancel button 5186 to return to the Pathway Generator window 5150. When a User 20 is finished using the Search for Stimulus window 5180, a User 20 may select the Exit button 5187 to return to the Pathway Generator window 5150.

FIG. 22 illustrates an Event Exclusion Criteria window 5210. A User 20 may expand the Event Exclusion Criteria window 5210 by selecting the More button 5211. Expansion of the Event Exclusion Criteria window 5210 allows the User 20 to enter more information. A User 20 may select a pre-defined field to exclude data by selecting from a list in the Field list 5212. The pre-defined fields may include references, experiment temperature, assays and species. A User 20 may also choose a selection in the Qualifier list 5213. The Qualifier list 5213 may include equal to, not equal to, less than, greater than, less than or equal to, or greater than or equal to. The options presented in the Values box 5214 may be dependent upon the selection made in the Field list 5212. A User 20 may search for values in the Database 80 using the Search button 5215. The Operator button 5216 may be a link between multiple rows of event exclusion criteria and may include AND or OR. A User 20 may enter information by selecting the OK button 5217. Upon selecting the OK button 5217, the Event Exclusion Criteria window 5210 may close and entered information may be transferred to the Pathway Generator window 5150. Alternatively, a User 20 may close the Event Exclusion Criteria window 5210 without transferring the information by selecting the Cancel button 5218.

Figure 20:
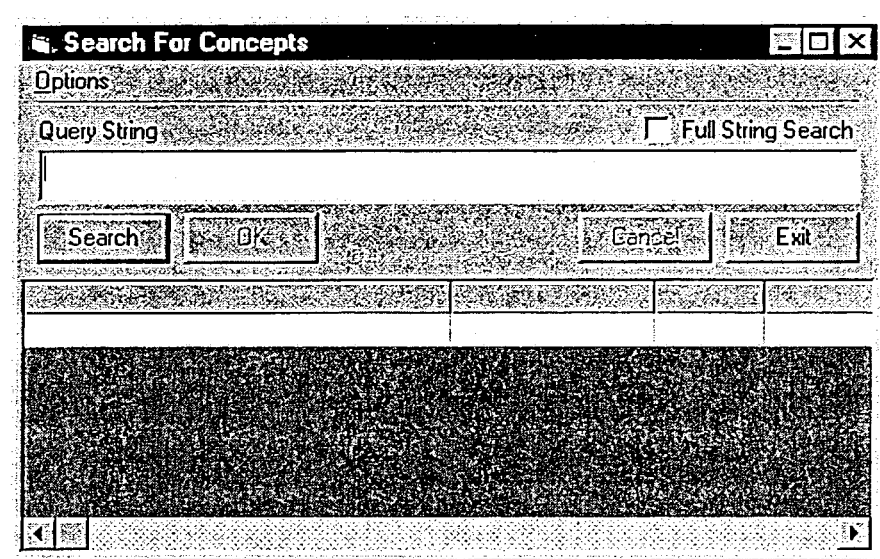
Figure 23:
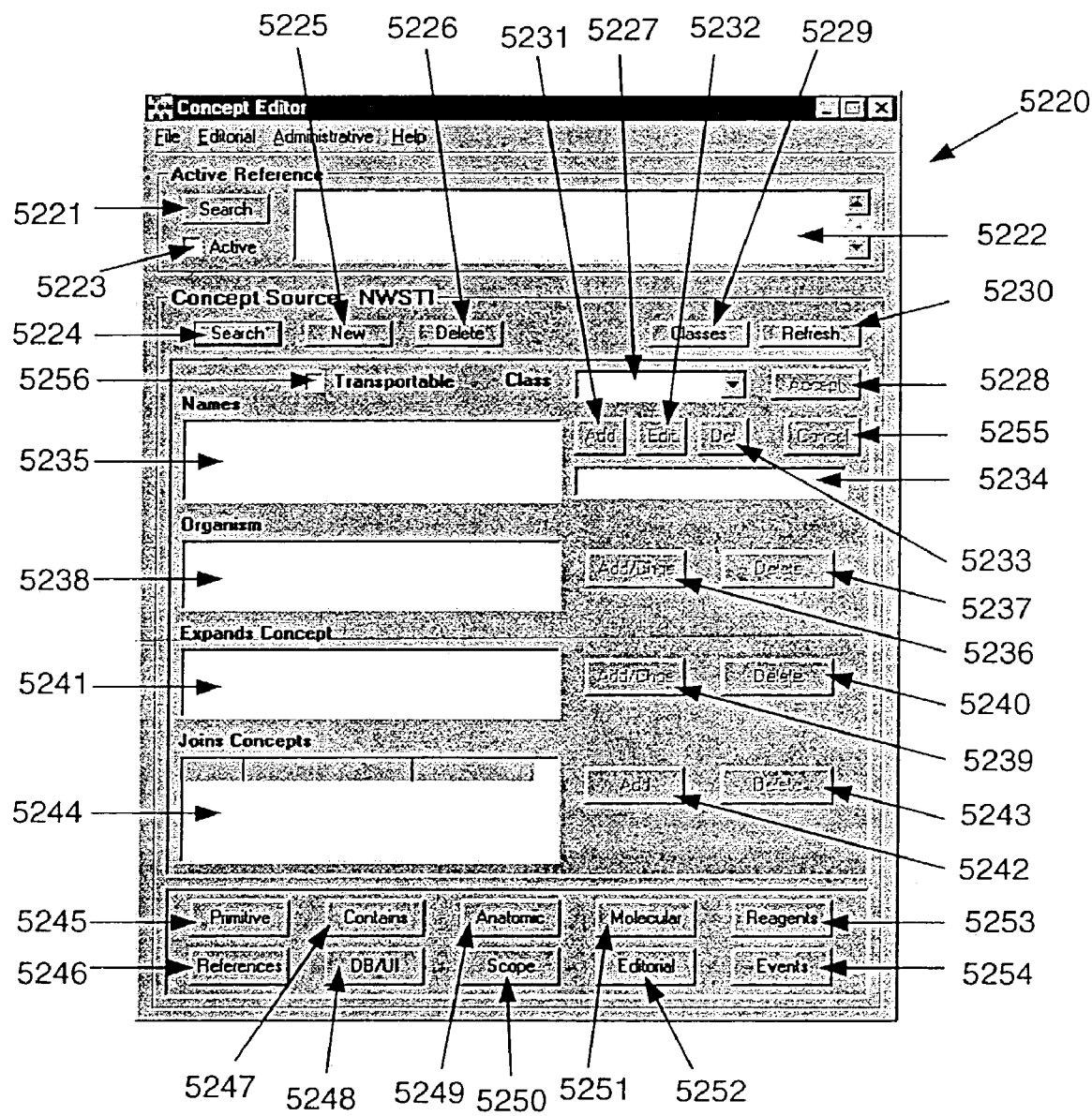

FIG. 23 illustrates a Concept Editor window 5220. The Concept Editor window 5220 may be displayed when a User 20 edits concept information or view information from a static display as a read-only display. A User 20 may search for a reference by selecting a Search button 5221. The Search button 5221 may open a Search for Reference window 5260. Upon selection of a reference, the reference information may be displayed in an Active Reference box 5222. If a reference is active (e.g., the reference is relevant to all entered information), the reference may be indicated with a check mark in the Active check box 5223. In an embodiment of the present invention, User 20 must have an active reference to enter information into the Database 80. A User 20 may search for concepts by selecting the Search button 5270. The Search button 5270 may present the Search for Concepts window 5190 (FIG. 20). Alternatively, a User 20 may enter a new concept by selecting a New button 5225. Upon selection of the New button 5225, the New Concept Name window 5280 may be presented. A User 20 may delete a concept by selecting a Delete button 5226. A User 20 may indicate if the concept is transportable by enabling the Transportable check box 5256. A User 20 may select a class for a given concept by entering the class from a list of classes presented in Class box 5227.

Figure 27:
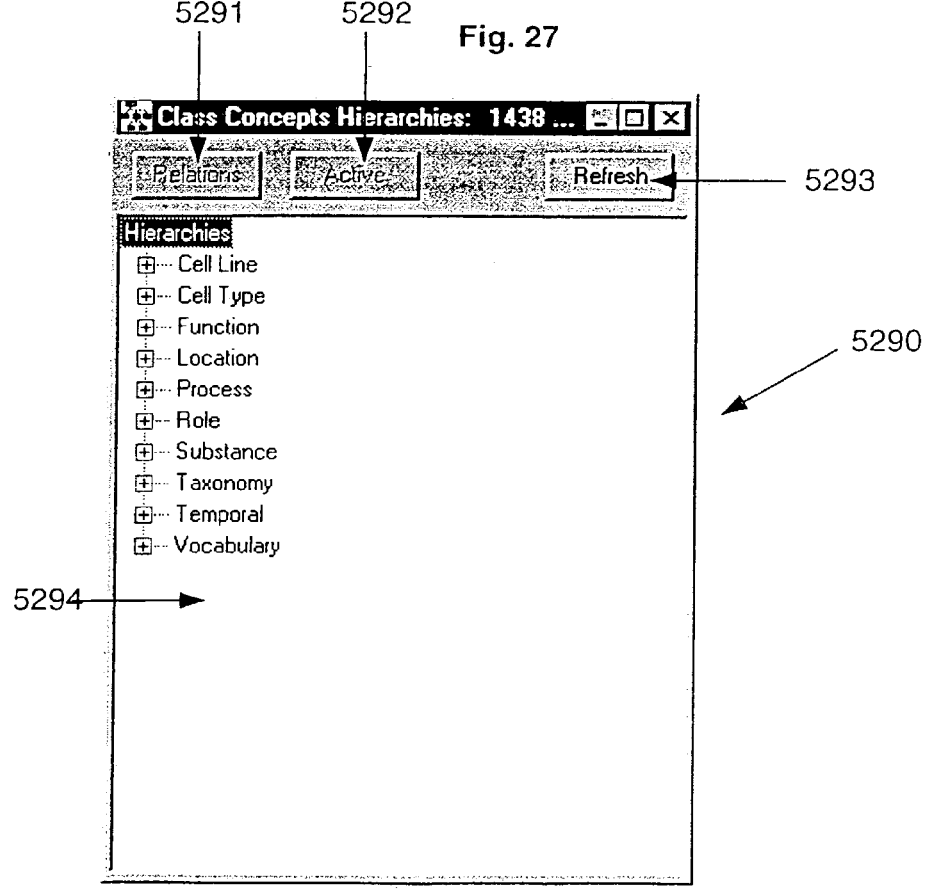

A User 20 may accept the selected class by selecting the Accept button 5228. A User 20 may also view a detailed listing of all class information by selecting a Class button 5229. Upon selection of the Class button 5229, a Class Concepts Hierarchies window 5290 may be presented. As shown in FIG. 27, the Class Concepts Hierarchies window 5290 may show all of the class information. A User 20 may refresh the Concept Editor window 5220 by selecting the Refresh button 5230. A User 20 may also Add, Edit, or Delete names by selecting button 5231, 5232, or 5233, respectively, subsequent to selecting a given name in the Names window 5235. Upon selection of a name in the Names window 5235, the selected name may be displayed in the Name Text box 5234 and a drop down list may be displayed with the name type below the Name Text box 5234.

A User 20 may cancel the active name by selecting the Cancel button 5255. A User 20 may choose to associate a concept with an organism by selecting the Add/Change button 5236, if an active relationship exists. Corresponding organism information may be displayed in the Organism window 5238. A User 20 may delete information by selecting the information in the Organism window 5238 and subsequently selecting the Delete button 5237. A User 20 may expand the concept from another concept by selecting the Add/Change button 5239, if an active relationship exists. The expanded information may be displayed in the Expands Concept window 5241. A User 20 may delete information by selecting given information in the Expands Concept window 5241 and subsequently selecting the Delete button 5241. A User 20 may join a concept with another concept by selecting the Add/Change button 5242, if an active relationship exists. The joined information may be displayed in the Joins Concept window 5244. A User 20 may delete information by selecting the given information in the Joins Concept window 5244 and subsequently selecting the Delete button 5243.

Figure 28:
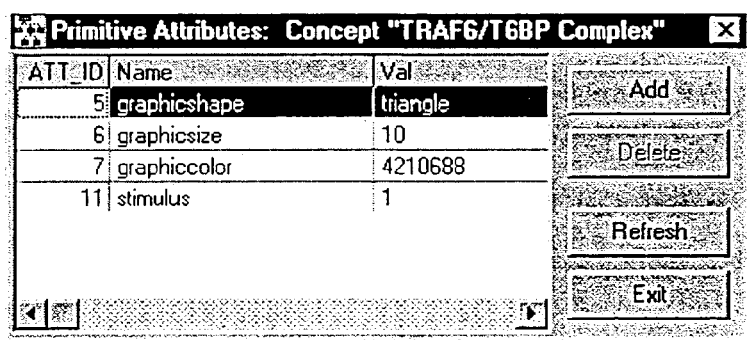
Figure 29:
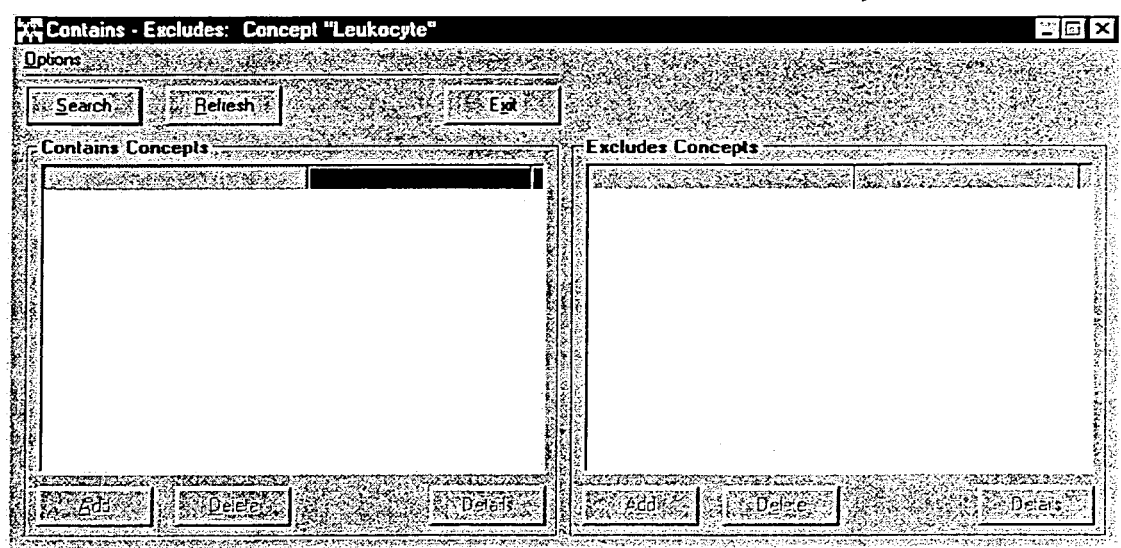
Figure 32:
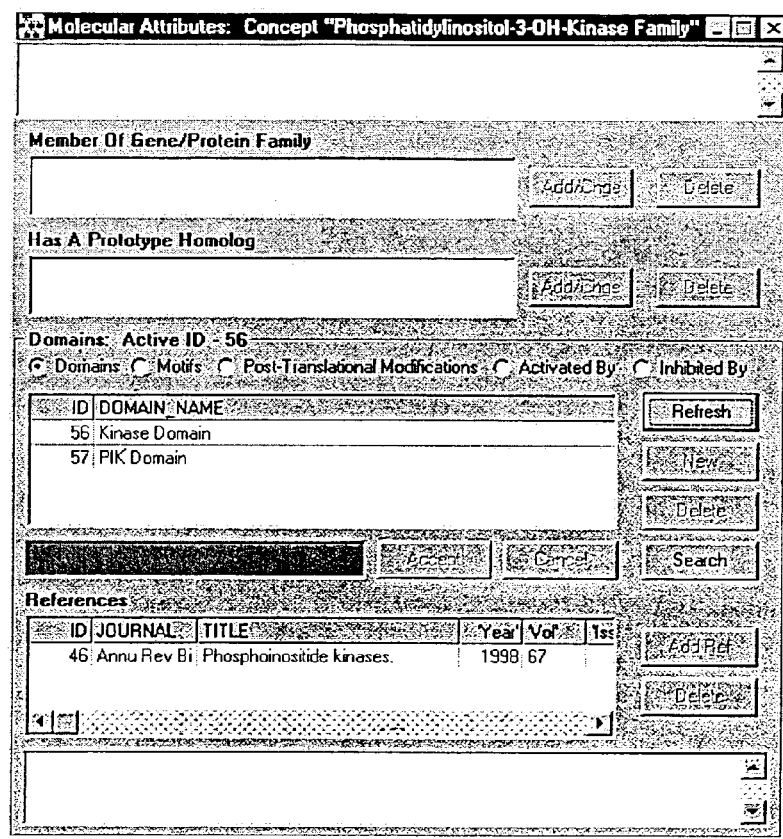
Figure 33:
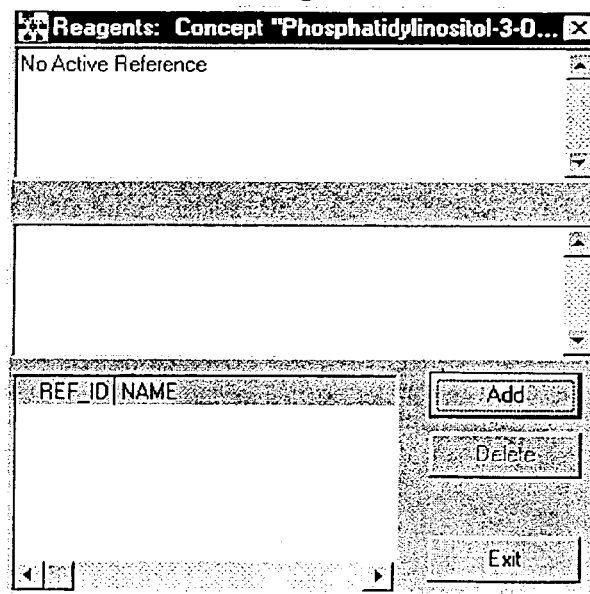
Figure 34:
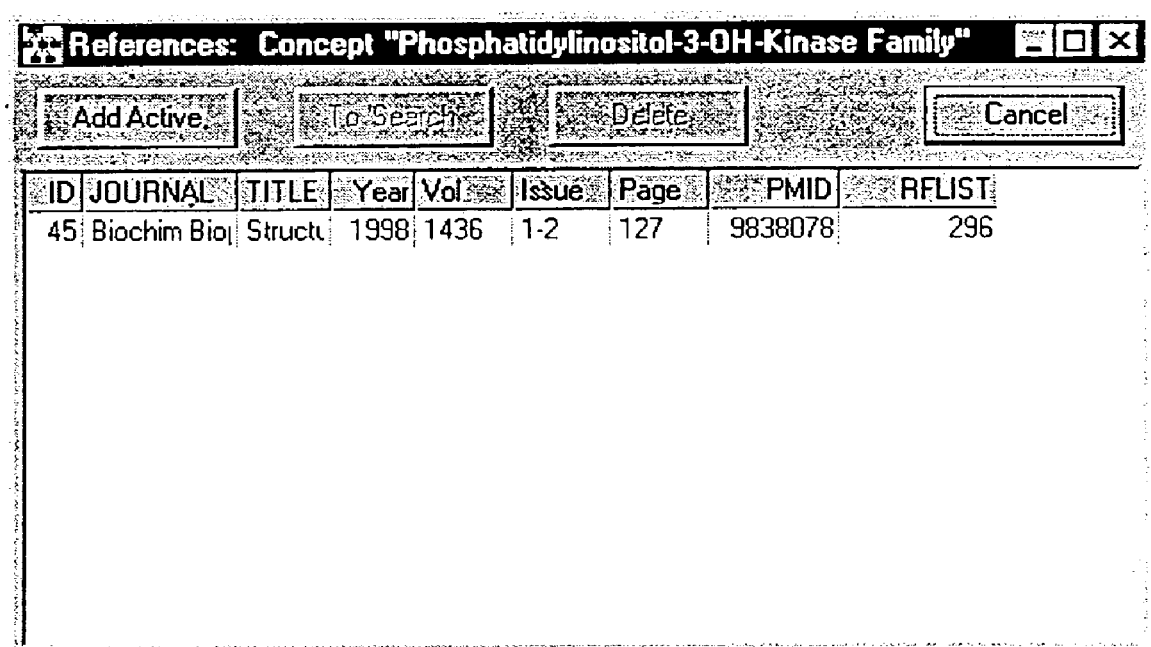
Figure 35:
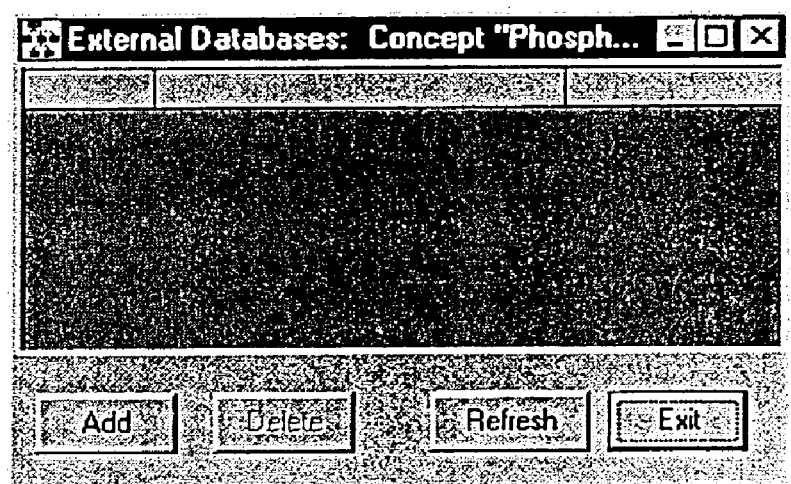
Figure 36:
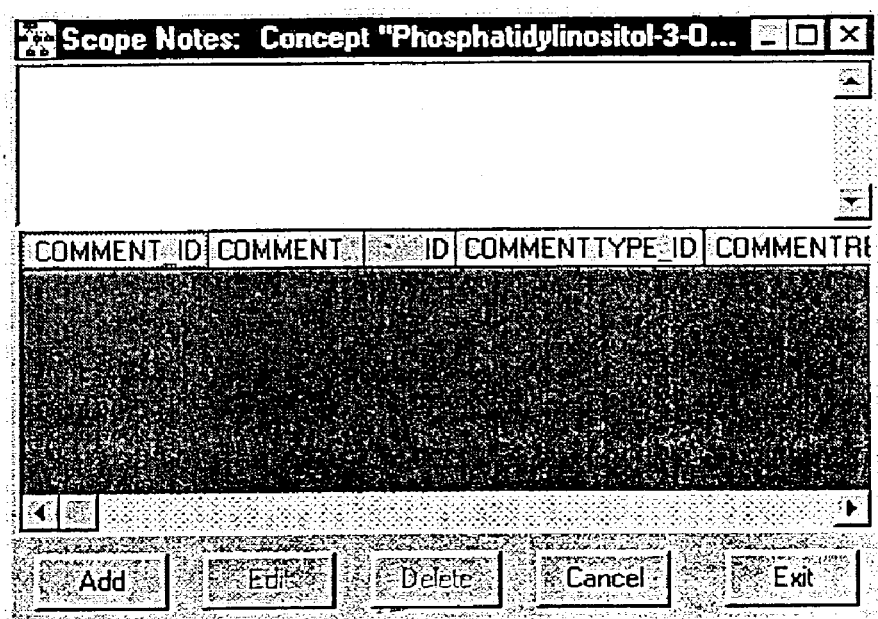
Figure 37:
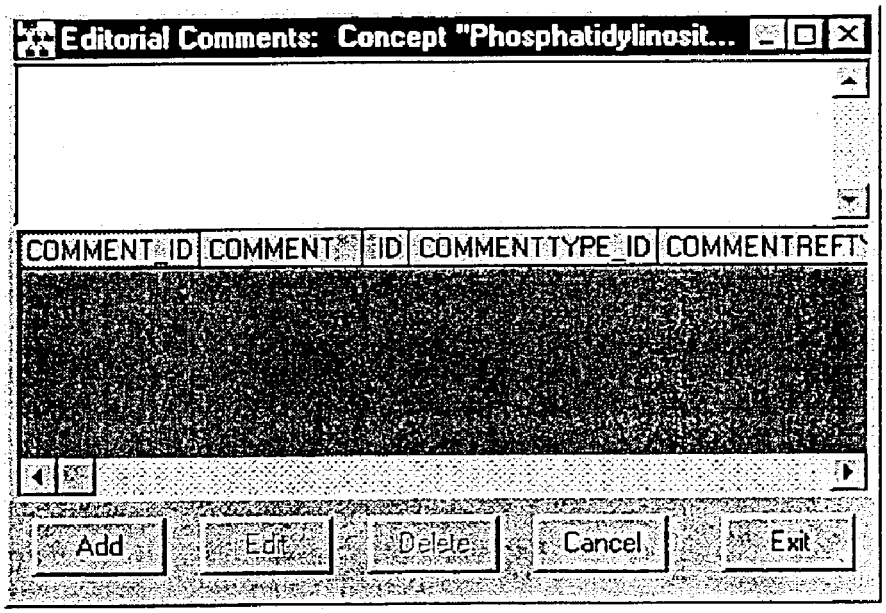
Figure 38:
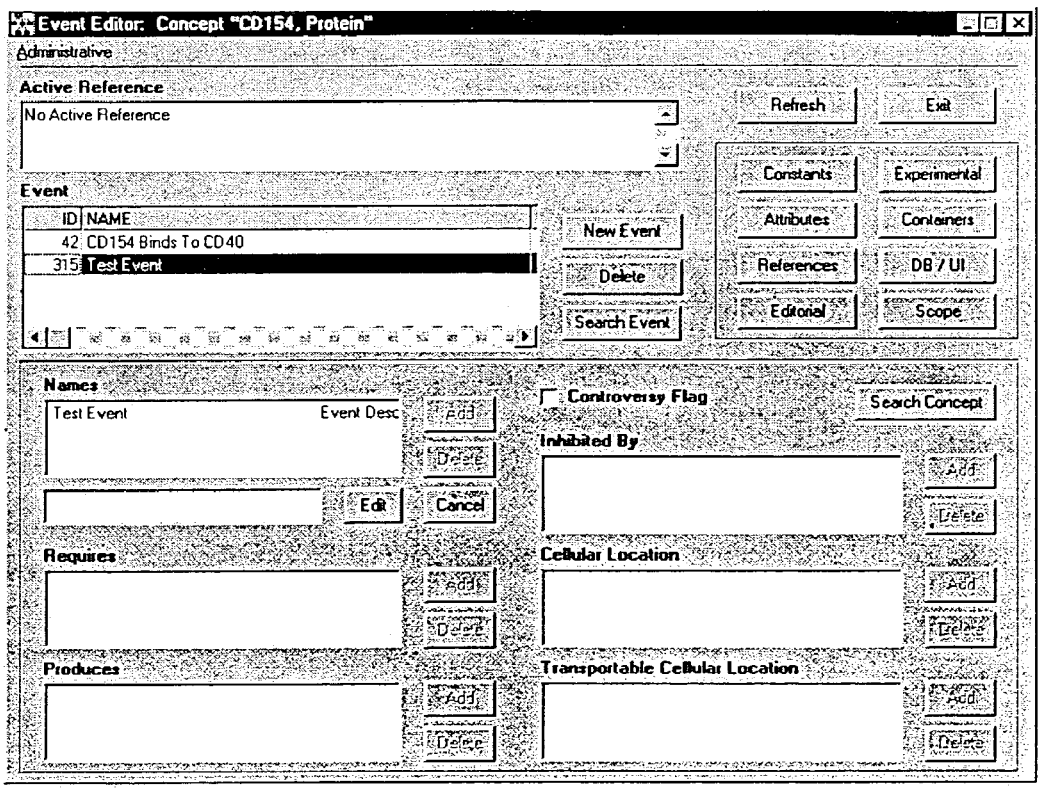

A User 20 may add primitive attributes to a concept by selecting the Primitive button 5245. Upon selection of the Primitive button 5245, a Primitive Attributes window 5300 may be presented, as shown in FIG. 28. A User 20 may choose to search references by selecting the References button 5246. Upon selection of the References button 5246, a References window 5360 may be presented, as shown in FIG. 34. A User 20 may choose to add contains information to a concept (e.g., a container) by selecting the Contains button 5247. Upon selection of the Contains button 5247, the Contains window 5310 may be presented, as shown in FIG. 29. A User 20 may choose to add database information to a concept by selecting the DB/UI button 5248. Upon selection of the DB/UI button 5248, the External Databases window 5370 may be presented, as shown in FIG. 35. A User 20 may choose to add anatomic attributes to a concept by selecting the Anatomic button 5249. Upon selection of the Anatomic button 5249, an Anatomic Attributes window 5330 may be presented, as shown in FIG. 31. A User 20 may choose to add scope notes to a concept by selecting the Scope button 5250. Upon selection of the Scope button 5250, a Scope Notes window 5380 may be presented, as shown in FIG. 36. A User 20 may choose to add molecular attributes to a concept by selecting the Molecular button 5251. Upon selection of the Molecular button 5251, a Molecular Attributes window 5340 may be presented, as shown in FIG. 32. A User 20, may choose to add editorial notes to a concept by selecting the Editorial button 5252. Upon selection of the Editorial button 5252, an Editorial Comments window 5390 may be presented, as shown in FIG. 37. A User 20 may choose to add reagents to a concept by selecting the Reagents button 5253. Upon selection of the Reagents button 5253, a Reagents window 5350 may be presented, as shown in FIG. 33. A User 20 may choose to associate the active concept with an event by selecting the Events button 5254. Upon selection of the Events button 5254, an Events Editor window 5400 may be presented, as shown in FIG. 38.

Figure 24:
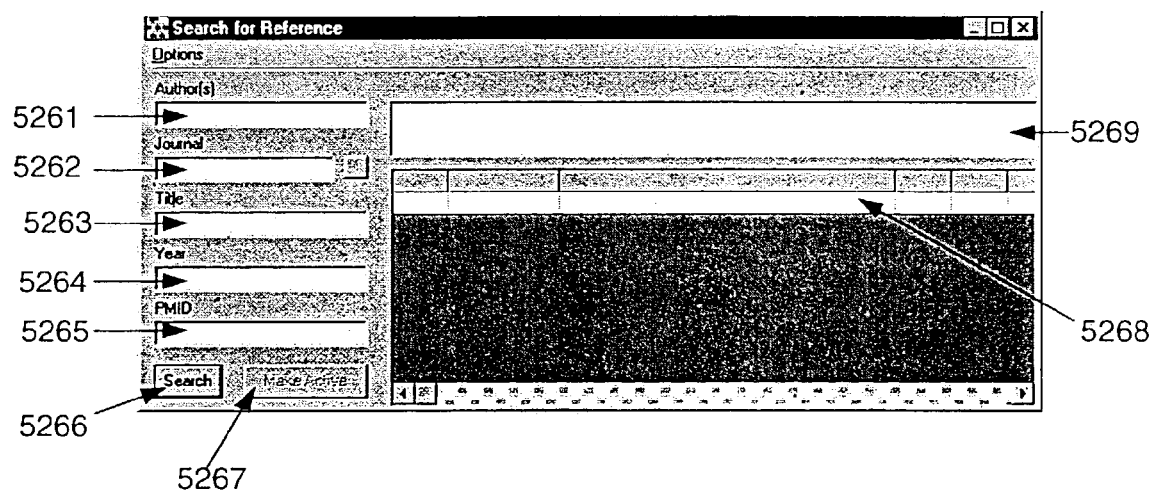

FIG. 24 illustrates a Search for Reference window 5260. The Search for Reference window 5260 may allow a User 20 to perform partial searches on reference information. A User 20 may enter author information in the Author text box 5262. A User 20 may enter reference titles in the Title text box 5263. A User 20 may enter publication year in the Year text box 5264. A User 20 may enter the distinct reference PMID in the PMID text box 5265. A User 20 may select the Search button 5266 to search based on the entered information. All information queried from the Database 80 corresponding to the given criteria may be displayed in the Results window 5268. A User 20 may select a reference in the Results window 5268. Upon selection of a reference in the Results window 5268, the full reference information may appear in the Full Reference Information window 5269. A User 20 may choose to make a reference active by selecting the Make Active button 5267.

Figure 21:
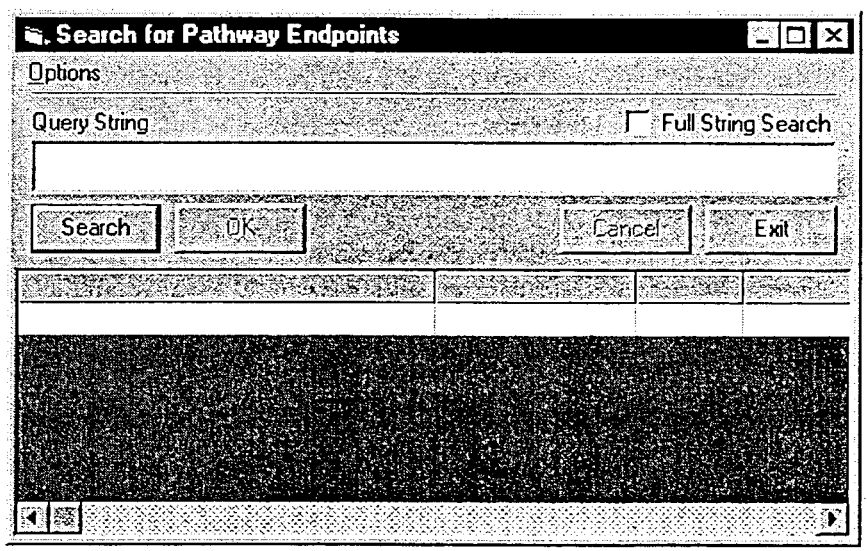
Figure 25:
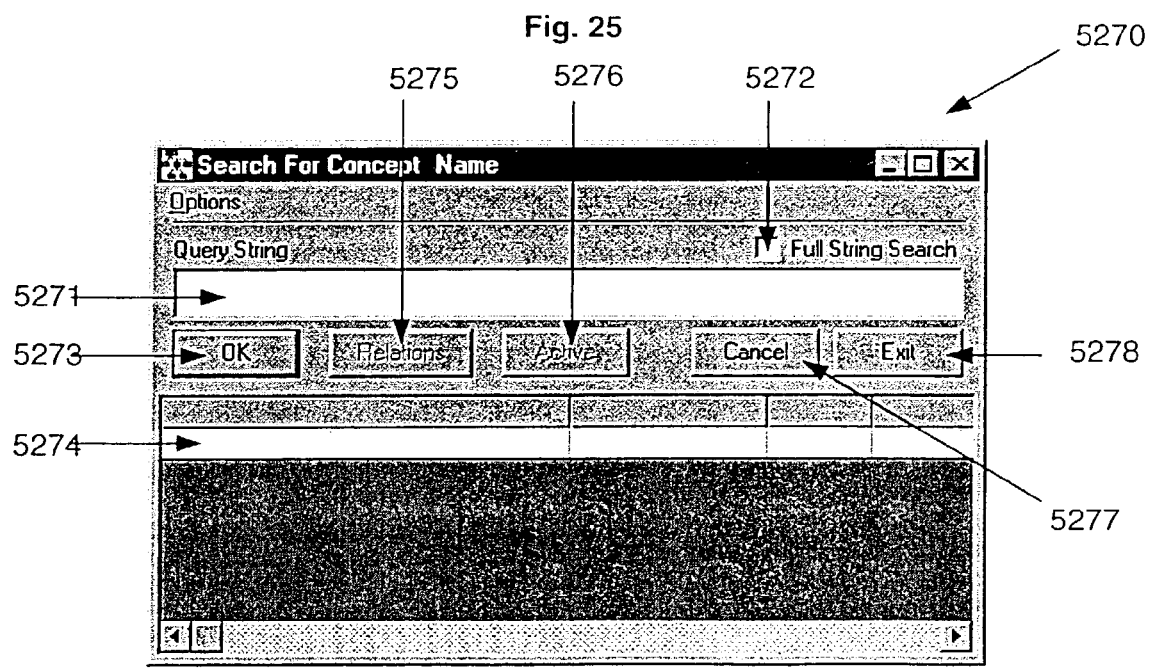

FIG. 25 illustrates a Search for Concept Name window 5270. The Search for Concept Name window 5270 may operate in a manner similar to the Search for Stimulus window 5180 (FIG. 19), the Search for Concepts window 5190 (FIG. 20), or the Search for Pathway Endpoints window 5200 (FIG. 21).

Figure 26:
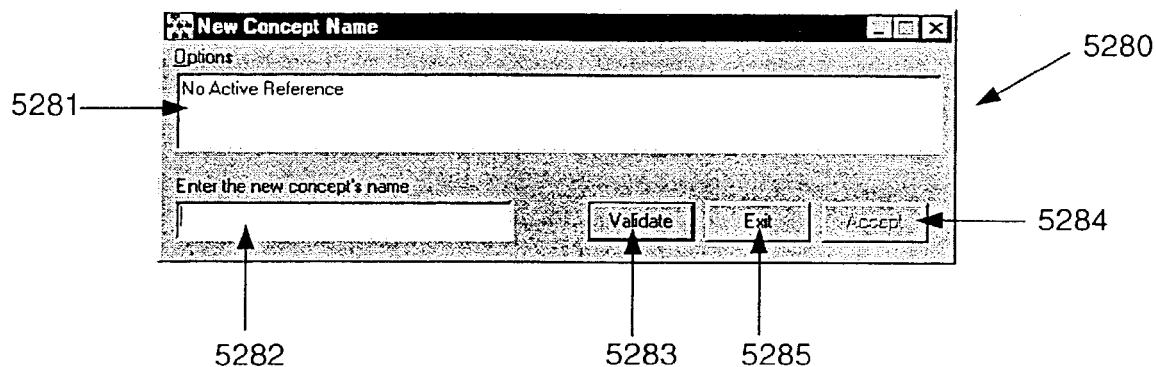

FIG. 26 illustrates a New Concept Name window 5280. The New Concept Name window 5280 may be used to enter a new concept. An active concept may be displayed in the Concept window 5281. A User 20 may enter a new concept name in the Concept box 5282. A User 20 may search for duplicate names by pressing the Validate button 5283. If a name is not a duplicate, the Validate button 5283 may not be selected by a User 20. If a name is a duplicate, an error message may be displayed to the User 20. A User 20 may accept the new name by selecting the Accept button 5284. A User 20 may exit the New Concept Name window 5280 by selecting the Exit button 5285.

FIG. 27 illustrates a Class Concepts Hierarchies window 5290. The Class Concepts Hierarchies window 5290 may be used to establish a class relationship to a concept. A User 20 may view the various class by browsing through the hierarchies in the Hierarchies window 5294. A User 20 may choose a relation by selecting the Relations button 5291. A User 20 may make the relationship active by selecting the Active button 5292. A User 20 may refresh the Hierarchies window 5294 by selecting the Refresh button 5293.

FIG. 28 illustrates a Primitive Attributes window 5300. The Primitive Attributes window 5300 may be used to assign primitive attributes to a concept. For example, a User 20 may assign values for display to a concept. A User 20 may also indicate whether a concept is a stimulus. A User 20 may add the entered primitive attributes to the concept by selecting the Add button 5301. A User 20 may refresh the Primitive Display box 5305 by selecting the Refresh button 5303.

FIG. 29 illustrates a Contains window 5310. The Contains windows 5310 may be used for showing containment of concepts in cellular context (e.g., cells, cell structures, etc.). A User 20 may search for concepts to add to a cellular context. A User 20 may initiate a search by selecting the Search button 5311. Upon selecting the Search button 5311, a User 20 may be presented with a search dialog and/or search results. Concept search results may be selected by a User 20 for containment in the cellular context. Such selected concepts may be displayed in the Contains Concept box 5316. Similarly, a User 20 may select concepts to exclude from the cellular context. Such concepts may be displayed in the Excludes Concepts box 5319. A User 20 may also locate concepts to contain in or exclude from the cellular contexts by utilizing a batch query as discussed in reference to FIG. 30.

Figure 30:
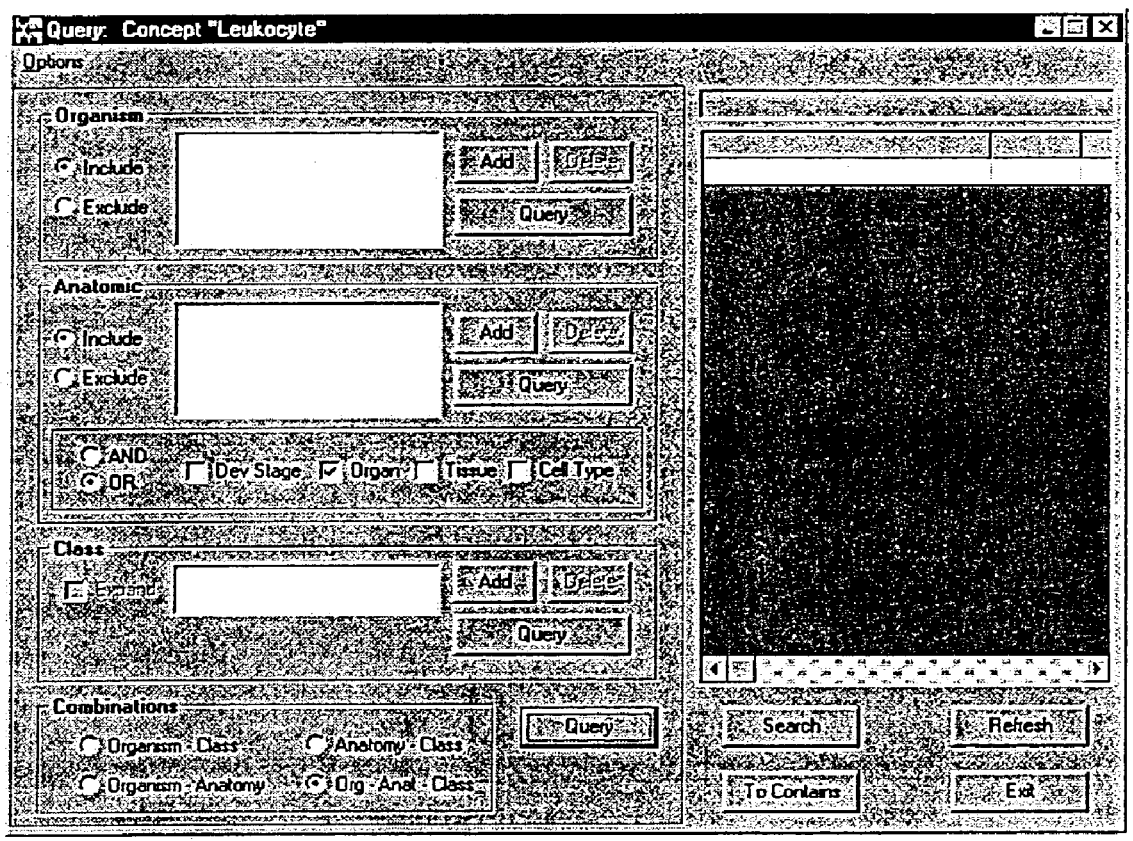

FIG. 30 illustrates a Query window 5320. A User 20 may utilize the Query window 5320 to execute a batch import of concepts in the Contains Concept box 5316 or the Excludes Concepts box 5319. A User 20 may choose to include or exclude an organism by selecting Include button 5321 or Exclude button 5322, respectively. A User 20 may choose to include or exclude an anatomic by selecting Include button 5323 or Exclude button 5324, respectively. After selecting the appropriate include or exclude radio button, a User 20 may choose organism specific information by selecting the Query button 5325, selecting the desired concepts, and selecting the Add button 5326. Similarly, a User 20 may choose anatomic information by setting up a search by selecting the desired contextual limitations (e.g., developmental stage, organ, tissue, cell type, etc.) and search term connectors (e.g., AND, OR, etc.). A User 20 may execute the search by selecting the Query button 5327. A User 20 may select class information by selecting the Query button 5328 to find concepts, selecting the desired concepts and then selecting the Add button 5329. If a User 20 wishes a class to be displayed with all sub-classes or inherited classes, a User 20 may select the Expand check box 5321*a*. A User 20 may execute individual queries for an organism, anatomic or class by selecting the corresponding query button. A User 20 user may execute a combination query for an organism, anatomic and/or class by selecting the Combination Query button 5321*b*. The Display box 5321*c* may display all information resulting from any searches or queries. A User 20 may send information displayed in the Display box 5321*c* to the Contains Concept box 5316 or the Excludes Concepts box 5319 by selecting the information and selecting the To Contains button 5321*e*. A User 20 may search for general concepts by selecting the Search button 5321*d*.

FIG. 31 illustrates an Anatomic Attributes window 5330. A User 20 may use the Anatomic Attributes window 5330 to associate anatomic information (e.g., organ, tissue, cell line, etc.) with a concept. The Top Display window 5331 displays information regarding an active reference. An active reference is a reference associated with a given concept. When new information is added to a concept, a new reference may be added. New reference information may be displayed in an Active ID Reference box 5333. Line item information for a new reference may be displayed in the Line Item Display box 5332. The Add/Change buttons 5334, 5336, 5338 and 5335 may be used to add and/or change information regarding developmental stage, organ, tissue and/or cell type. When a User 20 selects the Accept button 5339, information entered through the Anatomic Attributes window 5330 is validated and entered into the Database 80.

FIG. 32 illustrates a Molecular Attributes window 5340. A User 20 may use the Molecular Attributes window 5340 to associate molecular information with a concept. The Top Display window 5341 may display information regarding an active reference. The Member of Gene/Protein Family window 5342 displays information regarding membership of a reference or concept in a gene or protein family. The Has a Prototype Homolog window 5343 displays information regarding prototype homologs a reference or concept may have. A User 20 may select Domains radio button 5344, Motifs radio button 5345, Post-Translational Modifications radio button 5346, Activated By radio button 5347 or Inhibited By radio button 5348 to display corresponding Active ID information in Active ID Display box 5349. The References box 5349*e* may display more detailed reference information regarding the Active ID information corresponding to select Domains radio button 5344, Motifs radio button 5345, Post-Translational Modifications radio button 5346, Activated By radio button 5347 or Inhibited By radio button 5348.

FIG. 33 illustrates a Reagents window 5350. Top Display window 5351 may display information regarding an active reference. When a User 20 selects the Add button 5355, the User 20 may be prompted to enter a reagent name. Upon entering a reagent name, the reagent name may be displayed in Middle Display window 5352. A User 20 may add references associated with each reagent in Bottom Display window 5353 by selecting a given reference displayed in Bottom Display window 5353 and subsequently selecting the Add button 5355.

FIG. 34 illustrates a References window 5360. The References window 5360 may display references associated with a given concept. A User 20 may choose to activate a reference by selecting a reference from a list of references and subsequently selecting an Add Active button 5364. In the embodiment illustrated in FIG. 34, a User 20 may select a To 'Search' button 5363 to jump to the Search for Reference window 260 (FIG. 24).

FIG. 35 illustrates an External Databases window 5370. A User 20 may utilize the External Databases window 5370 to identify external databases for use by the Inference Engine 14. These external databases may be utilized by the Inference Engine 14 in conjunction with the Database 80. A User 20 may also utilize the External Databases window 5370 to identify unique identifiers associated with a concept.

FIG. 36 illustrates a Scope Notes window 5380. A User 20 may associate scope notes with a concept by entering the scope notes and selecting the Add button 5386. When a User 20 enters scope notes, selects the Add button 5386 and selects the Exit button 5382, the entered scope notes may be displayed in the Upper Display window 5387. Line item information may be displayed in Lower Display window 5381. A User 20 may select a line item in Lower Display window 5381. Subsequently, a User 20 may select an Edit button 5385 to edit the selected line item. A User 20 may also select a Delete button 5384 to delete the selected line item.

FIG. 37 illustrates an Editorial Comments window 5390. A User 20 may associate editorial comments with a concept by entering the editorial comments and selecting the Add button 5396. When a User 20 enters editorial comments, selects the Add button 5396 and selects the Exit button 5392, the entered editorial comments may be displayed in the Upper Display window 5397. Line item information may be displayed in Lower Display window 5391. A User 20 may select a line item in Lower Display window 5391. Subsequently, a User 20 may select an Edit button 5395 to edit the selected line item. A User 20 may also select a Delete button 5394 to delete the selected line item.

FIG. 38 illustrates an Event Editor window 5400. A User 20 may utilize the Event Editor window 5400 to enter information associated with events. Active Reference window 5401 may display an active reference. Event window 5402 may display the list of events associated with the active reference. A User 20 may add an event by selecting the New Event button 5400a. A User 20 may search for an event by selecting Search Event button 5408. Upon selection of the Search Event button 5408, the Search for Event Name window 5405 may be presented. Names window 5403 may display names and types of events. A User 20 may add or edit the names in Names window 5403 by entering information into Text window 5404. In an embodiment of the present invention, a User 20 must enter relevant information into the Requires window 5405 and the Produces window 5406. A User 20 may associate an event with a controversy flag by selecting the Controversy Flag check box 5407. A User 20 may select concepts by which the event is inhibited by selecting the Add button 5400b. A User 20 may also select where an event occurs by adding location information to a Cellular Location window 5400c. A User 20 may select a variety of different attributes to be associated with the event by selecting Constants button 5400d, Attributes button 5400e, References button 5400f, Editorial button 5400g, Experimental button 5400h, Containers button 5400i, DB/UI button 5400j, or Scope button 5400k.

Figure 40:
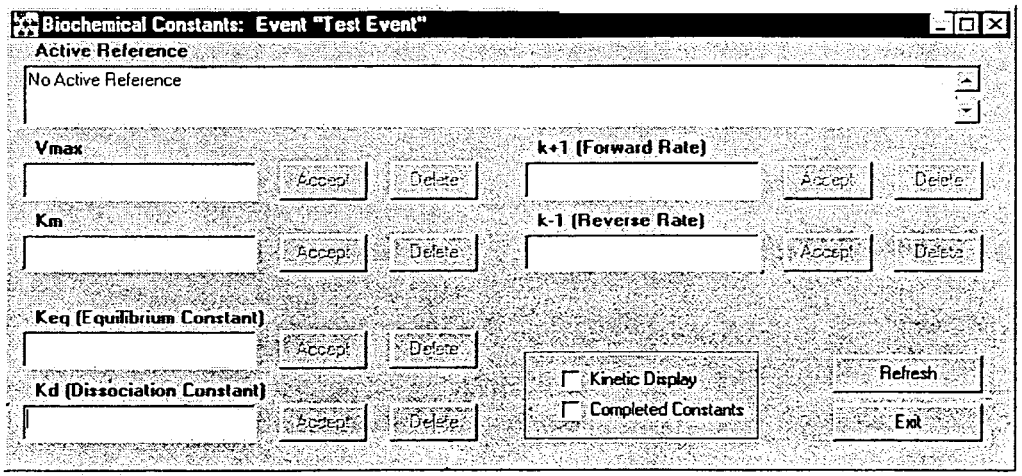
Figure 41:
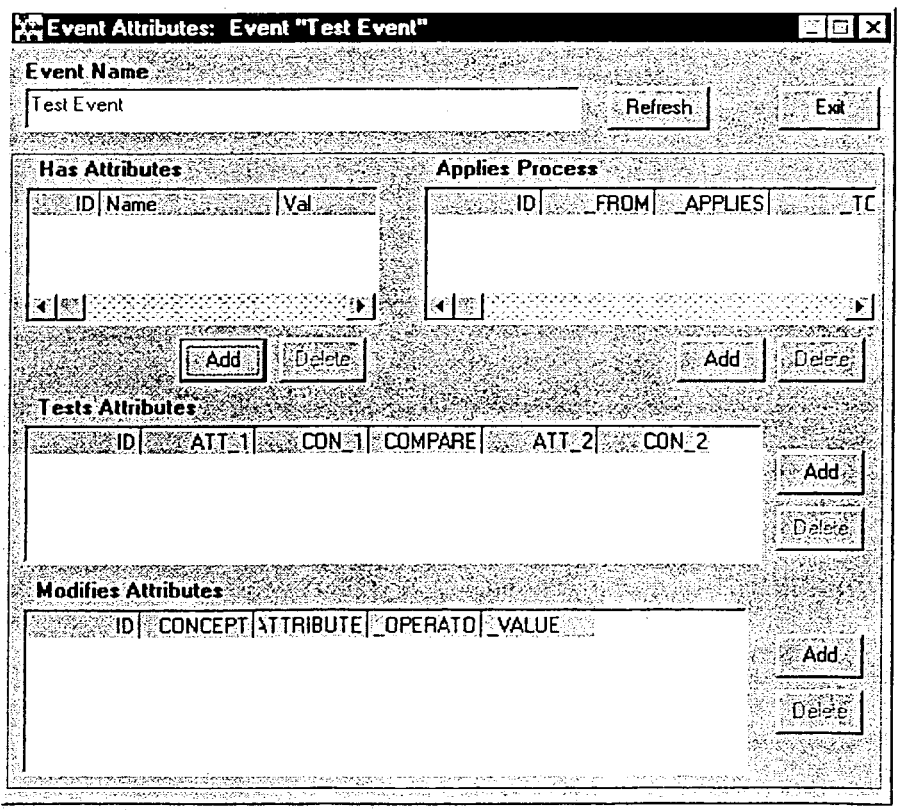
Figure 42:
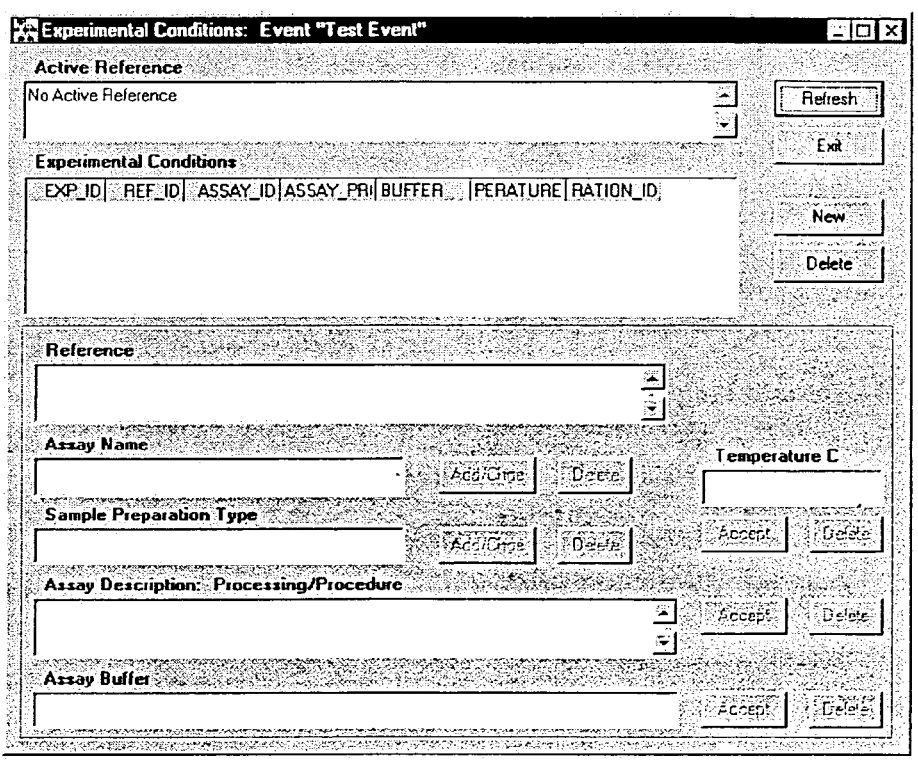

Upon selecting Constants button 5400d, a User 20 may be presented with Biochemical Constants window 5410 (FIG. 40). Upon selecting Attributes button 5400e, a User 20 may be presented with Event Attributes window 5420 (FIG. 41). Upon selecting Experimental button 5400h, a User 20 may be presented with Experimental Conditions window 5430 (FIG. 42). Upon selecting References button 5400f, a User 20 may be presented with References window 5360 (FIG. 34). Upon selecting Editorial button 5400g, a User 20 may be presented with Editorial Comments window 5390 (FIG. 37). Upon selecting DB/UI button 5400j, a User 20 may be presented with External Databases window 5370 (FIG. 35). Upon selecting Scope button 5400k, a User 20 may be presented with Scope Notes window 5380 (FIG. 36). Upon selecting Search Concepts button 54001, a User 20 may be presented with Search for Concept Name window 270 (FIG. 25).

Figure 39:
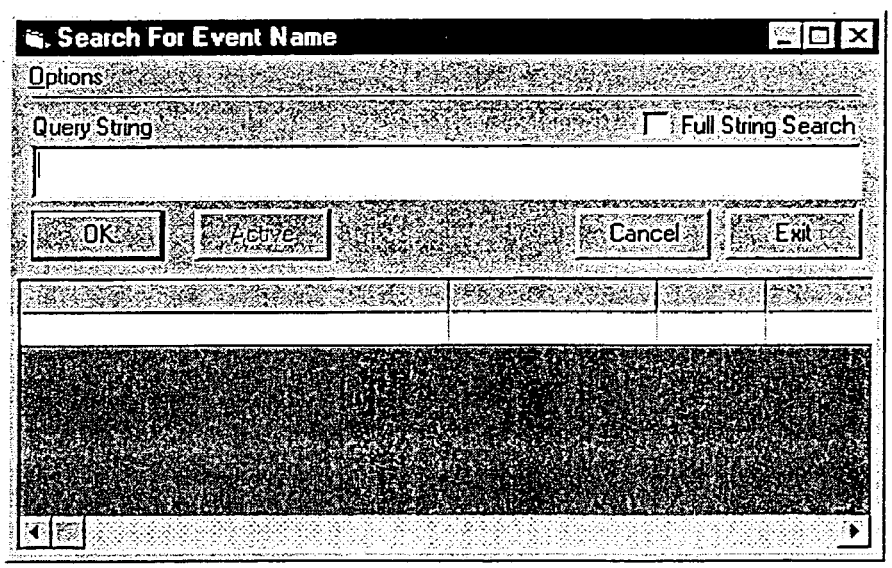

FIG. 39 illustrates a Search for Event Name window 5405. The Search for Concept Name window 5405 may operate and be utilized in a manner similar to the Search for Stimulus window 5180 (FIG. 19), the Search for Concepts window 5190 (FIG. 20), or the Search for Pathway Endpoints window 5200 (FIG. 21).

FIG. 40 illustrates a Biochemical Constants window 5410. Active Reference window 5411 may display an active reference. A User 20 may enter a maximum velocity in Vmax window 5412. A User 20 may enter a Michaelis constant in Km window 5413. A User 20 may enter an equilibrium constant in Keq window 5414. A User 20 may enter a dissociation constant in Kd window 5415. A User 20 may indicate that all constants are known by selecting Completed Constants check box 5416. Kinetic Display check box 5417 may be selected to indicate that the forward and reverse kinetic constants are known. A User 20 may enter a reverse kinetic constant in Reverse Rate window 5418. A User 20 may enter a forward kinetic constant in Forward Rate window 5419. Upon selection of Accept button 5410a, information entered in Biochemical Constants window 5410 may be validated and entered in Database 80.

FIG. 41 illustrates an Event Attribute window 5420. An event name may be displayed in Event Name window 5421. A User 20 may add attributes to the event in the Has Attributes window 5422. A User 20 may add test attribute conditions to the event by selecting Add button 5420a. A User 20 may add information that modifies an attribute of an event by selecting the Add button 5420b. A User 20 may add information that applies to an event by selecting the Add button 5420c associated with the Applies Process window 5420d.

FIG. 42 illustrates an Experimental Conditions window 5430. Active Reference window 5431 may display an active reference. Line items for all of the experimental condition information and associated reference IDs may be displayed in Experimental Conditions Display window 5432. When a User 20 selects a line item in Experimental Conditions Display window 5432, appropriate reference information may be displayed in Reference window 5433. When a User 20 searches for an assay using Add/Change button 5430b, a corresponding assay name may be displayed in Assay Name window 5434. When a User 20 searches for a preparation type using Add/Change button 5430c, a corresponding event preparation type may be displayed in Sample Preparation Type window 5435. Assay Description window 5436 may display an assay description. Assay Buffer window 5437 may display assay buffer information. Temperature window 5438 may display the experimental temperature. The information entered into the Experimental Conditions window 5430 may be verified and entered into the Database 80 by selecting the Accept button 5430a.

Figure 43:
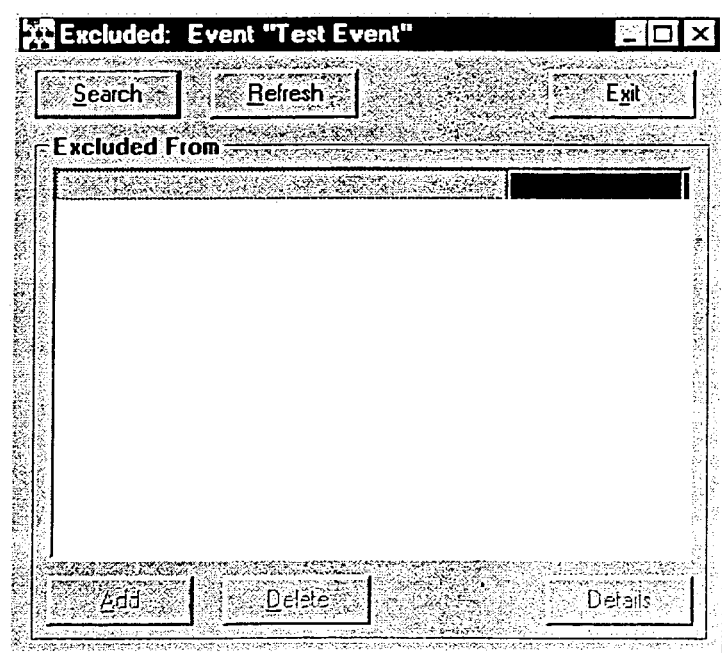

FIG. 43 illustrates an Excluded window 5440. The Excluded window 5440 may be displayed upon selection of the Containers button 5400i (FIG. 38). A User 20 may utilize the Excluded window 5440 to select containers from which the event is excluded. A User 20 may search for a given container upon selecting Search button 5440a. A User 20 may add a given container by selecting the Add button 5440b.

STL Shell

Examples are now presented for demonstration of grammar and representation only. Statements may have no basis in scientific fact.

Attributes: Attributes are used to annotate concepts and events. They are placeholders that represent information that can be assigned to a concept or an event. The mass of an object, the color of a protein on the screen, and all of the parameters that define how an object will move are all described by attributes.

The formal specification for defining an attribute is as follows:

ATTRIBUTE <attribute name> IS [ANY] [INTEGER|REAL|TEXT|OF] [<value list>] [FROM [EXACTLY] <number> TO [EXACTLY] <number>] [INCLUSIVE].

The grammar in square brackets [ ] is optional.

Some specific examples of definitions (with explanations):

Attribute "mass" is any real.

This statement defines an attribute called "mass" that can equal any real (decimal) number.

Attribute "abstract" is any text.

This statement defines an attribute called "abstract" that can equal any text.

Attribute "location" is any of "membrane-bound", "extracellular", "cytoplasmic".

This statement defines an attribute called "location" that can have any one of the values "membrane-bound", "extracellular" or "cytoplasmic".

Attribute "color" is any integer from 1 to 10 inclusive.

This statement defines an attribute called "color" that can have any integral value greater then or equal to 1, and less than or equal to 10. The "inclusive" keyword means that both the from-value and the to-value can be equal to their limits—a shorthand way of stating from exactly 1 to exactly 10.

Attribute "weight" is any real from 0.3.

This statement defines an attribute called "weight" that can have any real value greater than 0.3.

Attribute "height" is any real to exactly 14.3.

This statement defines an attribute called "height" that can have any real value less than or equal to 14.3.

Some of the attributes will be used by the Simulation Module 10 to determine whether or not a reaction will proceed. Most attributes will be used by the dynamic graphic display of the Simulation Module 10 to determine how the events will be represented on the screen. Attributes can also be used to store information about the concepts for hyperlinks and other data displays:

The following is a list of attributes that may be directly used by the system and method of the present invention.

Attribute Name, Purpose

Substance: Any concept that has this attribute will be listed as a substance in certain lists in the Concept, Event and Pathway wizards. Does not require any particular value to be assigned.

Process: Any concept that has this attribute will be listed as a process in the Process list in the Event wizard. Does not require any particular value to be assigned.

Structure: Any concept that has this attribute will be listed as a "structure" (cell or cellular component) in certain lists in the Concept, Event and Pathway wizards. Does not require any particular value to be assigned.

Duration: Assigned to an event, determines the length of time in seconds the event requires to proceed. May be a decimal number.

Graphicshape: Assigned to a concept, determines the shape of the concept in graphical presentation. Enumerated list with the following elements: none, triangle, square, circle.

Graphicsize: Assigned to a concept, determines the relative size of the concept in graphical presentation. Number from 1 to 100.

Graphiccolor: Assigned to a concept, determines the color of the concept in graphical presentation. Long integer in RGB format.

Location: Assigned to a concept, determines the starting cellular location of the concept in the dynamic graphical presentation. Enumerated list with the following elements: MB (membrane bound), Cyt (cytoplasmic), Comp (complexed), Nuc (nuclear), EC (extracellular) and ER (endoplasmic recticulum).

Mobile: Assigned to an event, determines which reactant(s) in the event will move in the dynamic graphical presentation. Consists of a string of 'Y' or 'N' characters, 'Y' means will move and 'N' means won't move. The characters are given in the order that the reactants are listed.

Postevent: Assigned to an event, determines which reactant(s) in the event will remain visible after the event is over in the dynamic graphical presentation. Consists of a string of 'Y' or 'N' characters, 'Y' means will be visible and 'N' means won't be visible. The characters are given in the order that the reactants are listed.

Stimulus: Any concept that has this attribute will be listed as a stimulus in the Stimulus list in the Pathway wizard. Does not require any particular value to be assigned.

Every substance or process is represented by a concept. Concepts can be defined as special types of other concepts, and can contain other concepts. Concepts can be assigned attributes, and may assign values to their attributes.

Concepts: The formal specification for defining a concept is as follows:

CONCEPT <concept name> [EXPANDS <base concept>[;]] [CONTAINS <concept list>[;]] [EXCLUDES <concept list>[;]] [JOINS <concept list>[;]] [HAS <attribute list>[;]] [SETS <attribute assignment list>].

The grammar in square brackets [ ] is optional.

Some specific examples of definitions (with explanations):

Concept "object" has "mass", "size".

This statement defines a concept called "object" to which the attributes "mass" and "size" have been assigned.

Concept "protein" expands "object".

This statement defines a concept called "protein" as a specific type of "object". The "protein" concept inherits the attributes of "object", therefore it has attributes "mass" and "size" associated with it automatically.

Concept "TNFR" expands "protein"; has "abstract"; sets "mass"=30, "abstract"="abstract of TNFR".

This statement defines a concept called "TNFR" as a specific type of "protein". It inherits the attributes of a "protein", and therefore automatically has "mass" and "size" attributes. It gives itself an "abstract" attribute (documentation of the protein). It sets its "mass" attribute to 30 (for the time being, we will use normalized values for physical attributes), and its "abstract" to the text "abstract of TNFR".

Concept "generic cell" expands "object"; contains "nucleus", "mitochondria", "cell membrane"; excludes "RAF"; sets "size"=40.

This statement defines a concept called "generic cell" as a specific type of "object". It inherits "mass" and "size" attributes from "object". It defines itself as a wrapper around the concepts "nucleus", "mitochondria", and "cell membrane", and sets its "size" to 40. It prevents the inheritance of the "RAF" concept from any of its child concepts. Concepts that contain other concepts do not inherit attributes from the concepts they contain.

Concept "Active FADD" expands "protein"; joins "active", FADD".

This statement defines a concept called "Active FADD" as a specific type of protein. It inherits the attributes of a protein, and joins together the concepts "active" and "FADD". Concepts that represent conjoined concepts inherit attributes from the concepts they contain. Conjoined concepts currently have little utility in the present invention; activated proteins are represented as inheriting from the inactivated forms:

Concept "active FADD" expands "FADD".

The events determine which concepts react, what concepts are produced as a result, the processes that occur within the reaction, and what determines whether or not the reaction will proceed.

Events: The formal specification for an event is as follows:
EVENT <event name> REQUIRES <concept list>[;] [TESTS <attribute> OF <concept> {EQUAL TO|LESS THAN|GREATER THAN} <attribute> OF <concept> [;]] [APPLIES <concept> FROM <concept> TO <concept> [;]] [PRODUCES <concept list> [;]] [INHIBITED BY <concept list>[;]] [PRESENT IN <concept list>[;]] [ABSENT IN <concept list>[;]] [HAS <attribute list>[;]] [SETS <attribute assignment list>].

The grammar in square brackets [ ] is optional.

Some examples of definitions (with explanations):

Event "Three molecules of TNF binds to and trimerizes TNFR" Requires "TNF", "TNF", TNF", "TNFR", "TNFR", "TNFR";
Applies "binds to" from "TNF" to "TNFR";
Applies "trimerizes" from "TNF" to "TNFR";
Produces "Trimer of TNFR";
Has "duration";
Sets "duration"=10.

This statement defines an event that requires three instances of the "TNFR" concept and three instances of the "TNF" concept to proceed. It produces the concept "Trimer of TNFR", and requires a "duration" of 10 to do so. It performs the reaction by applying the "binds to" and "trimerizes" concepts from "TNF" to "TNFR". (The purpose of the 'applies' clause is to break the reaction into pieces to describe the process to the static presentation engine.)

Event "GTP displaces GDP and activates heterotrimeric Gs protein"
Requires "GTP", "GDP-bound heterotrimeric Gs protein";
Tests "concentration" of "GTP" greater than "concentration" of "GDP";
Produces "active heterotrimeric Gs protein", "GDP".

This statement defines an event that requires "GTP" and "GDP-bound heterotrimeric Gs protein" to proceed. It produces the concepts "GDP" and "active heterotrimeric Gs protein". It tests that the attribute "concentration" of concept "GTP" is numerically greater than the attribute "concentration" of concept "GDP", and if so, permits the reaction to take place. No processes are specified, so if this event occurs it will not be fully animated. No duration is specified, so the animation engine will assign it a default reaction time of 5 seconds.

Event "Adenylyl cyclase converts ATP to cAMP and Pi"
Requires "Adenylyl cyclase", "ATP";
Applies "converts ATP to" from "adenylyl cyclase" to "ATP";
Present In "generic cell";
Produces "cAMP", "Pi".

This statement defines an event that requires "adenylyl cyclase" and "ATP" to proceed. It produces the concepts "cAMP" and "Pi". It will only occur in a "generic cell" context. It performs the reaction by applying the "converts ATP to" concept from "adenylyl cyclase" to "ATP". (This may be an area of some contention as to which concept "performs" the action and which concept it is "performed on". Naturally, the most scientifically appropriate definition of the process should be used if it is known.)

Event "TRADD binds to and activates TRAF2"
Requires "active TRADD", "TRAF2";
Inhibited by "FADD";
Absent In "liver cell";
Applies "binds to" from "TRADD" to "TRAF2";
Applies "activates" from "TRADD" to "TRAF2";
Produces "active TRAF2".

This statement defines an event that requires "active TRADD" and "TRAF2" to proceed. It produces that concept "active TRAF2". It performs the reaction by applying "binds to" and "activates" from "TRADD" to "TRAF2". The reaction will not occur if the concept "FADD" is present. The reaction will not occur in a liver cell (but will occur in every other type of cell).

The following tables may be used by the system and method of the present invention. They are preferably stored in structure form in memory. They are preferably read from and written to a structured storage document.

Data Tables:

The ANYVALUE structure is a VARIANT-like type that provides a transparent means of storing information of different types.

| Name | Type | Description |
|---|---|---|
| Lnum | long | Part of an anonymous union, stores a long integer value. |
| Fnum | double | Part of an anonymous union, stores a double floating point value. |
| Index | long | Part of an anonymous union, stores an index into a string table or enumerated value table. |
| Error | long | Part of an anonymous union, stores an error code. |
| Hasvalue | bool | Indicates whether the union contains a valid value. |
| Type | char | Indicates the type of the data contained within the union. |

The ANATOMIC table holds the anatomical information.

| Name | Type | Description |
|---|---|---|
| Anatomic_Id | long | Primary key for this table. Anatomic identifier. |
| Tissue | long | Identifies the tissue associated with the concept. |
| Reference_Id | long | Identifies the reference. |

-continued

| Name | Type | Description |
|---|---|---|
| CellType | long | Identifies the cell type. |
| MoleculesPerCell | double | Identifies the molecules per cell. |
| CellLine | text | Identifies the cell line |
| DevelopmentalStage | long | Identifies the developmental stage. |
| Organ | long | Identifies the organ |
| AnatExpression_Id | long | Identifies the anatomical expression. |

The ANATOMICEXPRESSION table holds the types of anatomical expression information.

| Name | Type | Description |
|---|---|---|
| AnatExpression_ID | long | Primary key for this table. Anatomic identifier. |
| Tissue | text | Identifies the anatomical expression type (e.g. Protein, RNA, etc.) |

The APPLIES table holds the applies process information.

| Name | Type | Description |
|---|---|---|
| Apply_Id | long | Primary key for this table. Identifier for the table. |
| Apply_Concept | long | Identifies the concept that is applied. |
| From_Concept | long | Identifies the concept that the relationship comes from. |
| To_Concept | long | Identifies the concept the relationship points to. |

The ASSAYNAME table holds the names of the assays used in the generation of the events.

| Name | Type | Description |
|---|---|---|
| Assay_Id | long | Primary key for this table. Applies identifier. |
| Name | Text | Identifies the name of the assay. |

The ATTRIBUTEENUMVALUE table holds all possible enumerated values for all enumerated list attributes. The offset within this table identifies which element of the enumerated list an enumerated list attribute represents.

| Name | Type | Description |
|---|---|---|
| AttributeENum_Id | long | Composite key for this table with Name. Attribute type identifier. |
| Name | text | Composite key for this table with AttributeENum_Id. Name of the attribute (e.g. shape, cellular location, etc.) |

The ATTRIBUTES table holds the attribute definitions.

| Name | Type | Description |
|---|---|---|
| Attribute_Id | long | Primary key for this table. Attribute identifier. |
| Name | text | Name of the attribute. |
| Type | long | Identifies the type of the attribute. (e.g. integer, real, enumerated list, etc.) |
| Bounds | char | Identifies the boundary limits of the attribute, if it is a number. |

| Name | Type | Description |
|---|---|---|
| Upperbound | long | Stores the upper bound of the attribute if it is numerical. |
| Lowerbound | long | Stores the lower bound of the attribute if it is numerical. |
| Upperexact | long | Indicates whether the upper bound is inclusive if the attribute is numerical. |
| Lowerexact | long | Indicates whether the lower bound is inclusive if the attribute is numerical. |

The AUTHORLINK table holds the links between authors and references.

| Name | Type | Description |
|---|---|---|
| AuthorLink_Id | long | Primary key for this table. Author link identifier. |
| Author_Id | long | Identifies the author. |
| Reference_Id | long | Identifies the reference. |

The AUTHORS table holds the author information.

| Name | Type | Description |
|---|---|---|
| Author_Id | long | Primary key for this table. Author identifier. |
| Name | Text | Identifies the name of the author. |

The CLASSES table holds the hierarchical relationships between concepts.

| Name | Type | Description |
|---|---|---|
| Concept_Id | long | Primary key for this table. Concept identifier. |
| Parent | long | Parent of the concept. |
| ClassType_Id | long | Class type identifier. |

The CLASSTYPE table holds the hierarchical relationship types.

| Name | Type | Description |
|---|---|---|
| ClassType_Id | long | Primary key for this table. Class type identifier. |
| Description | long | Describes the class type. |

The COMMENT table holds the comment information provided by the editors.

| Name | Type | Description |
|---|---|---|
| Comment_Id | long | Primary key for this table. Comment identifier. |
| CommentType_Id | long | Identifies the type of comment. (e.g. editor comments, scope notes, user notes, etc . . . ) |
| CommentRefType_Id | long | Identifies the comment reference type as "concept" or "event". |
| Id | long | Identifies the concept or event Id that is associated with the given comment. |
| Comment | text | Editor comments. |

The COMMENTREFTYPE table holds the comment reference type information.

| Name | Type | Description |
| --- | --- | --- |
| CommentRefType_Id | long | Primary key for this table. Comment reference type identifier. |
| Name | text | Name of the comment reference type. (Concept or Event) |

The COMMENTTYPE table holds the comment type information.

| Name | Type | Description |
| --- | --- | --- |
| CommentType_Id | long | Primary key for this table. Comment reference type identifier. (e.g. editor comments, scope notes, user notes, etc . . . ) |
| Name | text | Name of the comment type. |

The COMPAREENUM table holds the enumerated list values for attribute comparison.

| Name | Type | Description |
| --- | --- | --- |
| Compare_Id | Long | Primary key for this table. Comparison identifier. (e.g. equal to, less than, not greater than, etc . . . ) |
| Name | Text | Name of the comparison type. |

The CONCEPTATTRIBUTE table holds the concept attribute information.

| Name | Type | Description |
| --- | --- | --- |
| Concept_Id | long | Composite key for this table with Attribute_Id. Concept identifier. |
| Attribute_Id | long | Composite key for this table with Concept_Id. Attribute identifier. |
| StoredValue | text | Identifies the value of the concept's attribute. |
| HasValue | bool | Concept attribute indicator. |
| Type | long | Identifies the attribute type. |

The CONCEPTS table holds the concept definitions.

| Name | Type | Description |
| --- | --- | --- |
| Concept_Id | long | Composite key for this table. Concept identifier. |
| User_Id | long | Composite key for this table. User identifier. |

| Name | Type | Description |
| --- | --- | --- |
| Expands | long | Indicates another concept that the concept is based on. |
| Version_Id | long | Indicates the version of the concept for documentation purposes. |
| Organism | long | Indicates the organism the concept was present in. |
| Transportable | bool | Indicates whether the concept has the transportable feature. |
| Homolog_Of | long | Indicates what homolog(s) the concept may have. |
| GeneProteinFamily | long | Indicates concept membership in a gene or protein family. |
| Homolog_Flag | long | Indicates whether the concept is a homolog of another concept. |

The DBUI table holds the reference information for outside databases and unique identifiers.

| Name | Type | Description |
| --- | --- | --- |
| DBUI_Id | long | Primary key for this table. DBUI identifier. |
| DBUIType | long | Identifies the type of DBUI. |
| DB | long | Identifies the database type |
| UI | text | Identifies the UI type. |

The DBUITYPE table holds the enumerated type values for the DBUI.

| Name | Type | Description |
| --- | --- | --- |
| DBUIType_Id | Long | Primary key for this table. DBUI type identifier. |
| Name | Text | Name of the DBUI type. (e.g. string, numeric) |

The EVENTATTRIBUTE table holds the relationships between the events and the event attributes.

| Name | Type | Description |
| --- | --- | --- |
| Event_Id | long | Composite key for this table with Apply_Id. Event identifier. |
| Attribute_Id | long | Composite key for this table with Event_Id. Attribute identifier. |
| StoredValue | text | Actual value of the event attribute. |
| HasValue | bool | Event attribute indicator. |
| Type | long | Identifies attribute type. |

The EVENTS table holds the event definitions.

| Name | Type | Description |
| --- | --- | --- |
| Event_Id | long | Composite key for this table. Event identifier. |
| User_Id | Long | Composite key for this table. User identifier. |
| Controversy | long | Name or description of the event. |
| CellularLocation | long | Indicates whether this event has one or more Applies clauses (that define the processes in the event). |

-continued

| Name | Type | Description |
|---|---|---|
| Version_Id | long | Indicates whether this event has one or more Tests clauses. |
| TransportLocation | long | Indicates whether this event has one or more attributes. |
| EquilibriumConstantEQ | long | Equilibrium constant. |
| DissociationConstantKD | long | Dissociation constant. |
| ForwardKineticRateConstantK1 | long | Forward kinetic rate constant. |
| ReverseKineticRateConstantK1 | long | Reverse kinetic rate constant. |
| MichaelKM | long | Michaelis-Menten constant |
| EnzymaticVMax | long | Enzymatic maximum velocity. |
| KineticDisplay | bool | Kinetic display indicator. |
| CompletedConstants | bool | Completed constant indicator. |

The EVENTSPECIES table holds the event identifiers and the reference identifiers.

| Name | Type | Description |
|---|---|---|
| Event_Id | long | Primary key for this table. Event identifier. |
| Organism | long | Organism identifier. |

The EXPCONDITIONS table holds the experimental conditions in which the event was described.

| Name | Type | Description |
|---|---|---|
| ExpCondition_Id | long | Primary key for this table. Experimental condition identifier. |
| Reference_Id | long | Identifier for references. |
| Assay | long | Identifier for assay. |
| Preparation_Type | long | Identifier for preparation type. |
| AssayProcess | text | Assay process description. |
| AssayBuffer | text | Assay buffer description. |
| TemperatureC. | long | Temperature in degrees celcius. |

The EXTERNALDB table holds the DB identifier and the associated database name.

| Name | Type | Description |
|---|---|---|
| DB_Id | long | Primary key for this table. Database identifier. |
| Name | long | Name of the database. |

The GENCONCEPT table holds the generic concept details.

| Name | Type | Description |
|---|---|---|
| GenConcept_Id | long | Primary key for this table. Generic concept identifier. |
| GenConcept | long | Identifier for generic concepts. |
| Concept_Id | long | Identifier for concepts. |
| Type_Id | long | Identifier for type. |
| Value | text | Generic concept value |

The GENCONCEPTTYPES table holds the generic concept types.

| Name | Type | Description |
|---|---|---|
| Type_Id | long | Primary key for this table. Generic concept type identifier. |
| Name | text | Name of the generic concept types (e.g. inhibitors, activators, motifs, domains, modifications etc.) |

The JOURNAL_SOURCE_REF table holds the journal source information.

| Name | Type | Description |
|---|---|---|
| Journal_Id | long | Primary key for this table. Journal identifier. |
| Name | Text | Name of the journal. |
| Tier | Long | Journal quality tier as classified by New World. (e.g. Tier One, Tier Two, etc.) |

The MODIFIESATTRIBUTE table holds the attribute modification information.

| Name | Type | Description |
|---|---|---|
| Modification_Id | long | Primary key for this table. Attribute modification identifier. |
| Concept_Id | long | Identifier for concepts. |
| Operator_Id | long | Identifier for operator. |
| Attribute_Id | long | Identifier for attribute. |
| StoredValue | text | Value of attribute modification. |
| Type | text | Attribute type |

The NAMES table holds the name information.

| Name | Type | Description |
|---|---|---|
| Name_Id | long | Primary key for this table. Name identifier. |
| Name | text | Value of the name. |
| Type_Id | long | Name type |

The NAMETYPE table holds the name type definitions.

| Name | Type | Description |
|---|---|---|
| Type_Id | long | Primary key for this table. Name type identifier. |
| Name | text | Value of the name type (e.g. preferred name, synonym, official name, etc.) |

The OPERATOR table holds the operator definitions.

| Name | Type | Description |
|---|---|---|
| Operator_Id | long | Primary key for this table. Operator identifier. |
| Name | text | Value of the operator name (e.g. multiply, set, increment, etc.) |

The PACKAGES table holds the client package information.

| Name | Type | Description |
|---|---|---|
| Package_Id | long | Primary key for this table. Package identifier. |
| User_Id | long | Identifier for the user. |
| Name | text | Package name. |
| Description | text | Package description |

The PREPARATIONNAME table holds the information preparations.

| Name | Type | Description |
|---|---|---|
| Preparation_Id | long | Primary key for this table. Preparation identifier. |
| Name | text | The name of the preparation. |

The REACTIONS table holds the reaction relationship information.

| Name | Type | Description |
|---|---|---|
| Reaction_Id | long | Primary key for this table. Reaction identifier. |
| Event_Id | long | Identifier for events. |
| Concept_Id | long | Identifier for concepts. |
| Type_Id | long | Identifier for reaction type. |
| Stoichiometry_Data | long | Reaction stoichiometry. |

The REACTIONTYPE table holds the reaction types.

| Name | Type | Description |
|---|---|---|
| Type_Id | long | Primary key for this table. Reaction identifier. |
| Name | text | The name of the reaction. (e.g. requires, inhibited by, produces, excluded from, present in, etc.) |

The REAGENTS table holds the event reagent information.

| Name | Type | Description |
|---|---|---|
| Concept_Id | long | Primary key for this table. Concept identifier. |
| Reference_Id | long | Identifier for references. |
| Name | long | Reagent name. |

The REFERENCE table holds the reference information.

| Name | Type | Description |
|---|---|---|
| Reference_Id | long | Primary key for this table. Reaction identifier. |
| Journal | long | Identifier for journal. |
| Title | text | Reference title. |
| Year | long | Reference year. |
| Volume | text | Referene volume. |
| Issue | text | Reference issue. |
| Page_Start | text | Reference start page. |
| Page_End | text | Reference end page. |
| PMID | long | Reference PMID. |
| Review | bool | Reference review indicator. |

The RELATIONSHIPTYPE table holds the relationship type definitions.

| Name | Type | Description |
|---|---|---|
| Type_Id | long | Primary key for this table. Relationship type identifier. |
| Name | long | Relationship type name. |

The SECURITY table holds the concept and event security relationships.

| Name | Type | Description |
|---|---|---|
| Type | long | Composite key for this table with Event_Id and Concept_Id. Security type. |
| Event_Id | long | Composite key for this table with Type and Concept_Id. Event identifier. |
| Concept_Id | long | Composite key for this table with Type and Event_Id. Concept identifier. |
| Package_Id | long | Security package identifier. |

The TESTSATTRIBUTE table holds the attribute information for the tests functionality.

| Name | Type | Description |
|---|---|---|
| Test_Id | long | Primary key for this table. Test identifier. |
| Concept1 | long | First concept identifier for the test functionality. |
| Compare | long | Comparison identifier. |
| Attribute1 | long | First attribute identifier for the test functionality. |
| Attribute2 | long | Second attribute identifier for the test functionality. |
| Concept2 | long | Second concept identifier for the test functionality. |

The TIER table holds the reference tier definitions.

| Name | Type | Description |
| --- | --- | --- |
| Tier_Id | long | Primary key for this table. Tier identifier. |
| Description | text | The description of the tier. (e.g. Tier One, Tier Two, etc.) |

The USERS table holds the user security information information.

| Name | Type | Description |
| --- | --- | --- |
| User_Id | long | Primary key for this table. User identifier. |
| Password | text | User password. |
| Login | text | Login information for the user. |
| Full_Name | text | User full name. |

The VERSION table holds the user edit trail for data edited in the database.

| Name | Type | Description |
| --- | --- | --- |
| Version_Id | long | Primary key for this table. User identifier. |
| Name | text | User password. |
| VersionDate | text | Login information for the user. |
| ActionType | text | Edit action type. (e.g. Creation, Editing, Deletion, etc.) |

The VERSIONJUNCTION table holds the version information for concepts and events.

| Name | Type | Description |
| --- | --- | --- |
| Version_Id | long | Primary key for this table. Version identifier. |
| Concept_Id | long | Concept identifier. |
| Event_Id | long | Event identifier. |

In another embodiment of the present invention, the aforementioned information may be enhanced to model the three dimensional conformation of identified regions (in a protein under study) that might mediate protein-protein interactions. In a further embodiment of the present invention, reference links at key program sites provide the User 20 rapid access to more detailed published information. Hyperlinks are also provided at suitable locations pointing to organism-specific databases.

In another embodiment of the present invention, a User 20 may examine more closely the molecular details of any component in the proposed pathway. This ability has the advantage of allowing the User 20 to effectively zoom in and out on any pathway element for a closer (molecular) or broader (sub-cellular or cellular) look. For example, a a User 20 may take a closer look at the three dimensional conformation of a binding site and its interaction with the target site. The effect of sequence alterations or covalent modification of binding site subunits (e.g., by phosphorylation) may also be examined more closely. This information is advantageous in drug design studies; prediction of toxicity and side effects, and susceptibility issues due to genetic variation among diverse populations.

Although the present invention has been described in terms of particularly preferred embodiments, it is not limited to these embodiments. Alternative embodiments and modifications which would still be encompassed by the invention may be made by those skilled in the art, particularly in light of the foregoing teachings. For example, although the present invention has been described in connection with the simulation of biochemical pathways, it could be used for other applications. For example, the Inference Engine 14 of the Simulation Module 10 may be adapted to process information to predict automotive or computer network traffic. For this type of application, the Database 80 may contain known traffic concepts (e.g., cars, trucks, different types of weather, accidents, etc.) and known traffic events. These concepts and events may then be processed by the Inference Engine 14 of the Simulation Module 10 to predict traffic effects given a traffic stimulus.

Accordingly, this invention is intended to cover any alternative embodiments, modifications or equivalents which may be within the spirit and scope of the invention.

We claim:

1. A computer-implemented method for dynamically displaying a animated representation of a biochemical pathway, comprising:
  (i) providing as inputs:
    (a) a set of separately defined concepts and events, wherein the concepts are capable of joining other concepts,
    (b) a physiological context of the biochemical pathway,
    (c) at least one stimulus, and
    (d) an event corresponding to the at least one stimulus;
  (ii) dynamically determining substances available to the biochemical pathway and an order in which events occur in the biochemical pathway; and
  (iii) displaying a representation of at least part of the biochemical pathway, wherein the representation is a dynamic animated graphical display.

2. The method of claim 1, wherein the separately defined concepts comprise various attributes.

3. The method of claim 2, wherein the various attributes comprise information on shape, color, size or location of a graphic.

4. The method of claim 1, wherein at least one of the defined concepts comprises a contextual structure.

5. The method of claim 1, wherein at least one of the defined concepts is a compartment within a cell, part or all of an organelle, a cellular membrane, a cytoskeletal structure, a cell, an extracellular fluid, an extracellular structure, a tissue, an organ, or a compartment within an organ.

6. The method of claim 1, wherein at least one of the defined events comprise at least one attribute.

7. The method of claim 6, wherein the at least one attribute comprises reactants, products, inhibitors, and a context within which the at least one of the defined events may occur.

8. The method of claim 6, wherein the at least one attribute comprises information that the at least one of the defined events is inhibited by at least one inhibitor or is inhibited from occurring in at least one location.

9. The method of claim 1, wherein the biochemical pathway comprises a signal transduction pathway.

10. The method of claim 1, wherein the biochemical pathway effects catabolism, anabolism, regulation of oxidative metabolism, regulation of transcription, regulation of protein synthesis, regulation of cell differentiation, or regulation of cell division.

11. The method of claim 1, wherein the biochemical pathway is characteristic of a disease.

12. The method of claim 1, wherein the representation comprises a textual description of objects and processes of at least part of the biochemical pathway, listed in an order in which the objects and processes occur in the pathway.

13. The method of claim 1, wherein the representation comprises a textual description of objects and processes of at least part of the biochemical pathway, listed in a order in which the objects and processes occur in order of time step.

14. The method of claim 1, wherein the representation comprises a graphical representation of objects and processes of at least part of the biochemical pathway, wherein at least one of the objects is represented by a graphic symbol having a combination of color, shape and size unique for the at least one object.

15. The method of claim 14, further comprising displaying at least one textual label that identifies the at least one object that is represented by the graphic symbol.

16. The method of claim 14, further comprising displaying at least one textual label that identifies at least one of the processes.

17. The method of claim 14, further comprising displaying a dynamic animated graphical representation of part or all of the biochemical pathway.

18. The method of claim 1, wherein said concepts are adapted to inherit from other concepts.

19. The method of claim 1, wherein said concepts contain other concepts.

20. The method of claim 1, wherein said concepts comprise attributes.

21. The method of claim 20, wherein said attributes comprise indicia of shape, color, location of a graphic, time, or species.

* * * * *